US012734128B2

(12) United States Patent
Kanasty et al.

(10) Patent No.: US 12,734,128 B2
(45) Date of Patent: Sep. 15, 2026

(54) GASTRIC RESIDENCE SYSTEMS HAVING A FILAMENT FOR IMPROVED GASTRIC RESIDENCE

(71) Applicant: Nortiva Bio, Inc., Lexington, MA (US)

(72) Inventors: Rosemary Kanasty, Cambridge, MA (US); Tyler Grant, Arlington, MA (US); Jung Hoon Yang, Watertown, MA (US); David C. Dufour, Watertown, MA (US); Erik Robert Waldemar Ryde, Watertown, MA (US)

(73) Assignee: Nortiva Bio, Inc., Lexington, MA (US)

( * ) Notice: Subject to any disclaimer, the term of this patent is extended or adjusted under 35 U.S.C. 154(b) by 1010 days.

(21) Appl. No.: 17/774,126

(22) PCT Filed: Nov. 6, 2020

(86) PCT No.: PCT/US2020/059533

§ 371 (c)(1),
(2) Date: May 3, 2022

(87) PCT Pub. No.: WO2021/092483

PCT Pub. Date: May 14, 2021

(65) Prior Publication Data

US 2022/0409528 A1 Dec. 29, 2022

Related U.S. Application Data

(60) Provisional application No. 62/992,075, filed on Mar. 19, 2020, provisional application No. 62/933,211, filed on Nov. 8, 2019.

(51) Int. Cl.

| | |
|---|---|
| ***A61K 9/00*** | (2006.01) |
| ***A61K 47/10*** | (2017.01) |
| ***A61K 47/12*** | (2006.01) |
| ***A61K 47/32*** | (2006.01) |
| ***A61K 47/38*** | (2006.01) |

(52) U.S. Cl.
CPC ............ *A61K 9/0065* (2013.01); *A61K 47/10* (2013.01); *A61K 47/12* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 3,531,368 | A | 9/1970 | Okamoto et al. |
| 3,716,614 | A | 2/1973 | Watanabe et al. |
| 4,304,767 | A | 12/1981 | Heller et al. |
| 4,812,012 | A | 3/1989 | Terada et al. |
| 5,002,772 | A | 3/1991 | Curatolo et al. |
| 5,121,329 | A | 6/1992 | Crump |
| 5,340,433 | A | 8/1994 | Crump |
| 7,276,252 | B2 | 10/2007 | Payumo |
| 9,884,022 | B2 | 2/2018 | Deshmukh et al. |
| 10,182,985 | B2 | 1/2019 | Bellinger et al. |
| 10,413,507 | B2 | 9/2019 | Zhang et al. |
| 10,517,819 | B2 | 12/2019 | Bellinger et al. |
| 10,517,820 | B2 | 12/2019 | Bellinger |
| 10,532,027 | B2 | 1/2020 | Bellinger |
| 10,596,110 | B2 | 3/2020 | Bellinger |
| 10,610,482 | B2 | 4/2020 | Bellinger |
| 10,716,751 | B2 | 7/2020 | Bellinger et al. |
| 10,716,752 | B2 | 7/2020 | Bellinger et al. |
| 10,849,853 | B2 | 12/2020 | Bellinger et al. |
| 10,953,208 | B2 | 3/2021 | Zhang et al. |
| 11,077,056 | B2 | 8/2021 | Bellinger et al. |
| 11,083,690 | B2 | 8/2021 | Zhang et al. |
| 11,246,829 | B2 | 2/2022 | Bellinger et al. |
| 11,357,723 | B2 | 6/2022 | Bellinger et al. |
| 11,389,399 | B2 | 7/2022 | Bellinger et al. |
| 11,576,859 | B2 | 2/2023 | Kanasty et al. |
| 11,576,866 | B2 | 2/2023 | Bellinger et al. |
| 11,793,751 | B2 | 10/2023 | Grant et al. |
| 11,992,552 | B2 | 5/2024 | Bellinger |
| 12,023,406 | B2 | 7/2024 | Kanasty |
| 12,109,305 | B2 | 10/2024 | Bellinger |
| 12,142,158 | B2 | 11/2024 | Kanasty |
| 2005/0249798 | A1 | 11/2005 | Mohammad |
| 2007/0037792 | A1 | 2/2007 | Lang |

(Continued)

FOREIGN PATENT DOCUMENTS

| | | |
|---|---|---|
| CN | 101400363 A | 4/2009 |
| CN | 106573999 A | 4/2017 |

(Continued)

OTHER PUBLICATIONS

Verma, S., et al., International Journal of Biological Macromolecules 64: 347-352 (Year: 2014).*
Burt, H.M. et al. (1999). "Development of Copolymers of Poly(D,L-lactide) and Methoxypolyethylene Glycol as Micellar Carriers of Paclitaxel," Colloids and Surfaces B: Biointerfaces 16(1-4):161-171.
European Examination Report, dated Jul. 15, 2025, for European Patent Application No. 20885040.4,6 pages.
Extended European Search Report, dated Jan. 17, 2024, for European Patent Application No. 20884024.9, 7 pages.
Extended European Search Report, dated Jan. 31, 2024, for European Patent Application No. 20885040.4, 13 pages.
Extended European Search Report, dated Jan. 9, 2024, for European Patent Application No. 20885272.3, 7 pages. Felix Lanao, R.P. et al. (Aug. 2013, E-pub Mar. 1, 2013). "Physicochemical Properties and Applications of Poly (Lactic-Co-Glycolic Acid) for Use in Bone Regeneration," Tissue Eng Part B Rev. 19(4):380-390.

(Continued)

*Primary Examiner* — David J Blanchard
*Assistant Examiner* — Daniel F Coughlin
(74) *Attorney, Agent, or Firm* — MORRISON & FOERSTER LLP

(57) ABSTRACT

Provided are gastric residence systems comprising: a core; a plurality of arms connected to the core at a proximal end through a plurality of linker components, one linker component of the plurality of linker components corresponding to each arm of the plurality of arms, and the plurality of arms extending radially from the proximal end, and a filament circumferentially connecting each arm of the plurality of arms.

20 Claims, 14 Drawing Sheets

(56) References Cited

U.S. PATENT DOCUMENTS

| | | | | |
|---|---|---|---|---|
| 2007/0156248 | A1 | 7/2007 | Marco et al. | |
| 2007/0196416 | A1 | 8/2007 | Li et al. | |
| 2008/0131484 | A1 | 6/2008 | Robinson et al. | |
| 2010/0286628 | A1 | 11/2010 | Gross | |
| 2012/0269866 | A1 | 10/2012 | Ali et al. | |
| 2013/0017264 | A1 | 1/2013 | Khandare et al. | |
| 2013/0225778 | A1 | 8/2013 | Goodrich et al. | |
| 2013/0273135 | A1 | 10/2013 | Brooks et al. | |
| 2016/0317453 | A1 | 11/2016 | Richey et al. | |
| 2016/0317796 | A1 | 11/2016 | Zhang et al. | |
| 2017/0106099 | A1 | 4/2017 | Bellinger et al. | |
| 2018/0311154 | A1 | 11/2018 | Kanasty | |
| 2019/0125667 | A1 | 5/2019 | Bellinger et al. | |
| 2019/0133936 | A1 | 5/2019 | Bellinger et al. | |
| 2019/0209090 | A1 | 7/2019 | Langer et al. | |
| 2019/0231697 | A1 | 8/2019 | Bellinger et al. | |
| 2019/0254966 | A1 | 8/2019 | Bellinger et al. | |
| 2019/0262265 | A1 | 8/2019 | Bellinger et al. | |
| 2020/0281851 | A1 * | 9/2020 | Grant .................. | A61M 31/002 |
| 2021/0196627 | A1 | 7/2021 | Grant et al. | |
| 2022/0160642 | A1 | 5/2022 | Bhise et al. | |
| 2022/0192995 | A1 | 6/2022 | Kanasty et al. | |
| 2022/0387310 | A1 | 12/2022 | Altreuter et al. | |
| 2022/0387311 | A1 | 12/2022 | Kanasty et al. | |
| 2022/0387312 | A1 | 12/2022 | Kanasty et al. | |
| 2023/0039421 | A1 | 2/2023 | Bellinger et al. | |
| 2023/0190941 | A1 | 6/2023 | Montezco et al. | |
| 2024/0139102 | A1 | 5/2024 | Grant | |
| 2024/0252483 | A1 | 8/2024 | Bhise | |
| 2024/0335400 | A1 | 10/2024 | Beguin | |
| 2024/0342081 | A1 | 10/2024 | Bellinger | |
| 2024/0382418 | A1 | 11/2024 | Kanasty | |
| 2024/0390270 | A1 | 11/2024 | Kanasty | |
| 2024/0398701 | A1 | 12/2024 | Kanasty | |
| 2024/0423909 | A1 | 12/2024 | Bellinger | |

FOREIGN PATENT DOCUMENTS

| | | | |
|---|---|---|---|
| CN | 108472249 | A | 8/2018 |
| CN | 108697649 | A | 10/2018 |
| CN | 109310639 | A | 2/2019 |
| CN | 110022861 | A | 7/2019 |
| JP | 2017505817 | A | 2/2017 |
| JP | 2017524662 | A | 8/2017 |
| JP | 2018515476 | A | 6/2018 |
| JP | 2019501110 | A | 1/2019 |
| JP | 2019503347 | A | 2/2019 |
| JP | 2022553867 | A | 12/2022 |
| TW | 201902459 | A | 1/2019 |
| WO | 2015119653 | A1 | 8/2015 |
| WO | 2015191920 | A1 | 12/2015 |
| WO | 2015191925 | A1 | 12/2015 |
| WO | 2017070612 | A1 | 4/2017 |
| WO | 2017100367 | A1 | 6/2017 |
| WO | 2017205844 | A2 | 11/2017 |
| WO | 2018064630 | A1 | 4/2018 |
| WO | 2018102799 | A1 | 6/2018 |
| WO | 2018227147 | A1 | 12/2018 |
| WO | 2019060458 | A1 | 3/2019 |
| WO | 2021092484 | A1 | 5/2021 |
| WO | 2021092486 | A1 | 5/2021 |
| WO | 2021092487 | A1 | 5/2021 |
| WO | 2021092491 | A1 | 5/2021 |
| WO | 2023141524 | A2 | 7/2023 |
| WO | 2024031023 | A2 | 2/2024 |
| WO | 2024073752 | A2 | 4/2024 |

OTHER PUBLICATIONS

Makadia, H.K. et al. (2011). "Poly Lactic-co-Glycolic Acid (PLGA) as Biodegradable Controlled Drug Delivery Carrier," Polymers 3:1377-1397.

Manna, S. et al. (2018). "Improved Design and Characterization of PLGA/PLA-Coated Chitosan Based Micro-Implants for Controlled Release of Hydrophilic Drugs," International Journal of Pharmaceutics, 547(1-2):122-132.

Moroishi, H et al. (2018). "PLA- and PLA/PLGA-Emulsion Composite Biomaterial Sheets for the Controllable Sustained Release of Hydrophilic Compounds," Materials, 11(12)2588: 12 pages.

Partial Supplementary European Search Report, dated Nov. 6, 2023, for European Patent Application No. 20885040.4, 14 pages.

Poly(D, L-Lactide-co-glycolide), Poly(D, L-lactide-co-glycolide), 50:50, IV 0.40 dl/g, acid-terminated. (May 29, 2017). https://web.archive.org/web/20170529103446/https://www.polysciences.com/defau1Upoly-d-l-lactide-co-glycolide-50-50-iv-0-40-dl-g via wayback machine 2 pages.

Poly(D,L-lactic acid), IV 2.0 DUG. Poly(dl-lactic acid) i.v. 2.0-2.8dl/g I Polysciences, Inc. (2016, Aug. 24). https://web.archive.org/web/20160824222556/https://www.polysciences.com/defau1Upolydl-lactic-acid-iv-20-28dlg via wayback machine 3 pages.

Alhnan, M.A. et al. (Aug. 2016; e-published on May 18, 2016). "Emergence of 3D PrintedOpportunities and Challenges," Pharm. Res. 33(8):1817-1832, 38 pages.

CAS No. 112945-52-5 (2017). "Silicon Dioxide," 5 pages.

CAS No. 9003-11-6 (Dec. 21, 2022). "Polyethylene-Polyproylene Glycol," 2 pages.

Haslauer, C.M. et al. (Jul. 2015; e-published on Sep. 17, 2014). "Translating Textiles to Tissue Engineering: Creation and Evaluation of Microporous, Biocompatible, Degradable Scaffolds Using Industry Relevant Manufacturing Approaches and Human Adipose Derived Stem Cells," J. Biomed. Mater. Res. B Appl. Biomater. 103(5):1050-1058, 22 pages.

International Preliminary Report on Patentability, issued May 10, 2022, for PCT Application No. PCT/US/2020/059533, filed Nov. 6, 2020, 7 pages.

International Preliminary Report on Patentability, issued May 10, 2022, for PCT Application No. PCT/US/2020/059534, filed Nov. 6, 2020, 6 pages.

International Preliminary Report on Patentability, issued May 10, 2022, for PCT Application No. PCT/US/2020/059536, filed Nov. 6, 2020, 7 pages.

International Preliminary Report on Patentability, issued May 10, 2022, for PCT Application No. PCT/US/2020/059537, filed Nov. 6, 2020, 8 pages.

International Preliminary Report on Patentability, issued May 10, 2022, for PCT Application No. PCT/US/2020/059541, filed Nov. 6, 2020, 16 pages.

International Search Report and Written Opinion, mailed Feb. 2, 2021, for PCT Application No. PCT/US/2020/059534, filed Nov. 6, 2020, 8 pages.

International Search Report and Written Opinion, mailed Feb. 4, 2021, for PCT Application No. PCT/US/2020/059533, filed Nov. 6, 2020, 9 pages.

International Search Report and Written Opinion, mailed Feb. 4, 2021, for PCT Application No. PCT/US/2020/059541, filed Nov. 6, 2020, 19 pages.

International Search Report and Written Opinion, mailed Mar. 25, 2021, for PCT Application No. PCT/US/2020/059536, filed Nov. 6, 2020, 10 pages.

International Search Report and Written Opinion, mailed Mar. 25, 2021, for PCT Application No. PCT/US/2020/059537, filed Nov. 6, 2020, 11 pages.

Khaled, S.A. et al. (2014). "Desktop 3D Printing of Controlled Release Pharmaceutical Bilayer Tablets," International Journal of Pharmaceutics 17 pages.

Mukherji, G. et al. (2003). "Enteric Coating for Colonic Delivery," Chapter 18 in Modified-Release Drug Delivery Technology 126:223-232.

Singh, S.P. et al. (2011). "Measurement and Analysis of Vibration and Temperature Levels in Global Intermodal Container Shipments on Truck, Rail and Ship," Packaging Technol. Science, 12 pages.

U.S. Appl. No. 17/774,128, filed May 3, 2022, Montezco et al. br(issued by the Office on Sep. 21, 2004).

Ursan, I.D. et al. (Mar.-Apr. 2013). "Three-Dimensional Drug Printing: A Structured Review," J. Am. Pharm. Assoc. 53(2):136-144.

(56) References Cited

OTHER PUBLICATIONS

Yu, D.G. et al. (Sep. 2008). "Three-Dimensional Printing in Pharmaceutics: Promises and Problems," J. Pharm. Sci. 97(9):3666-3690.
European Examination Report dated Oct. 24, 2025, for European Patent Application No. 20884800.2, 4 pages.
Evonik Industries. (Jul. 2015). "RESOMER Product Range" Evonik Industries 2.6, 4 pages.
Martin, L.M. et al. (2014). "Applications of Polyethylene Oxide (POLYOX) in Hydrophilic Matrices," Chapter 5 in Hydrophilic Matrix Tablets for Oral Controlled Release, pp. 123-141, 22 pages.

* cited by examiner

GASTRIC RESIDENCE SYSTEMS HAVING A FILAMENT FOR IMPROVED GASTRIC RESIDENCE

CROSS-REFERENCE TO RELATED APPLICATIONS

This application is a national stage application under 35 U.S.C. § 371 of International Application No. PCT/US2020/059533, filed internationally on Nov. 6, 2020, which claims priority benefit of U.S. Provisional Patent Application No. 62/933,211 filed on Nov. 8, 2019 and U.S. Provisional Patent Application No. 62/992,075 filed on Mar. 19, 2020. The entire contents of those applications are hereby incorporated by reference herein.

FIELD OF THE INVENTION

This relates to gastric residence systems, and more particularly, to gastric residence systems having a filament for improved gastric residence.

BACKGROUND OF THE INVENTION

Gastric residence systems are delivery systems for agents which remain in the stomach for days to weeks, or even over longer periods, during which time drugs or other agents can elute from the systems for absorption in the gastrointestinal tract. Examples of such systems are described in International Patent Application Nos. WO 2015/191920, WO 2015/191925, WO 2017/070612, WO 2017/100367, and PCT/US2017/034856.

Gastric residence systems are designed to be administered to the stomach of a patient, typically in a capsule which is swallowed or introduced into the stomach by an alternate method of administration (for example, feeding tube or gastric tube). Upon dissolution of the capsule in the stomach, the systems expand or unfold to a size which remains in the stomach and resists passage through the pyloric sphincter over the desired residence period (such as three days, seven days, two weeks, etc.). This requires mechanical stability over the desired residence period. Over the period of residence, the system releases an agent or agents, such as one or more drugs, preferably with minimal burst release, which requires careful selection of the carrier material for the agent in order to provide the desired release profile. While resident in the stomach, the system should not interfere with the normal passage of food or other gastric contents. The system should pass out of the stomach at the end of the desired residence time, and be readily eliminated from the patient. If the system prematurely passes from the stomach into the small intestine, it should not cause intestinal obstruction, and again should be readily eliminated from the patient. These characteristics require careful selection of the materials from which the system is constructed, and the dimensions and arrangement of the system.

SUMMARY OF THE INVENTION

Provided are gastric residence systems comprising a filament for improved gastric residence and methods of preparing gastric residence forms having a filament. In particular, gastric residence systems having a filament described herein may help improve the gastric residence of the gastric residence system. Specifically, a filament can help provide a more consistent gastric residence time and/or a longer gastric residence time. Thus, gastric residence systems provided herein that include a filament may provide more predictable and/or controllable gastric residence times. Gastric residence systems having predictable and/or controllable gastric residence times can minimize the risk of the gastric residence system unfolding too early (e.g., in the esophagus) and causing an obstruction. Gastric residence systems having predictable and/or controllable gastric residence times can also minimize the possibility of the gastric residence system passing through the stomach and unfolding later in the gastrointestinal tract (i.e., intestine), or passing through the gastrointestinal tract without unfolding at all. In each of these possible scenarios, the therapeutic agent of the gastric residence dosage form is not delivered to the patient as intended.

In some embodiments, a gastric residence system is provided, the gastric residence system comprising: a core; a plurality of arms connected to the core at a proximal end through a plurality of linker components, one linker component of the plurality of linker components corresponding to each arm of the plurality of arms, and the plurality of arms extending radially from the proximal end; and a filament circumferentially connecting each arm of the plurality of arms.

In some embodiments of the gastric residence system, the filament circumferentially connects a distal end of each arm of the plurality of arms.

In some embodiments of the gastric residence system, the plurality of arms comprises at least three arms.

In some embodiments of the gastric residence system, the plurality of arms is configured to be loaded with an active pharmaceutical ingredient.

In some embodiments of the gastric residence system, the plurality of arms comprises 40-60% loading of an active pharmaceutical ingredient.

In some embodiments of the gastric residence system, the linker component degrades, dissolves, disassociates, or mechanically weakens in a gastric environment.

In some embodiments of the gastric residence system, the gastric residence system is configured to be folded during administration and is configured to assume an open configuration when in a patient's stomach.

In some embodiments of the gastric residence system, the core undergoes elastic deformation when the gastric residence system is in the folded configuration and recoils when the gastric residence system assumes the open configuration.

In some embodiments of the gastric residence system, the gastric residence system has a multi-armed star shape in the open configuration.

In some embodiments of the gastric residence system, the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

In some embodiments of the gastric residence system, the pullout force required to separate the filament from the distal end of a first arm of the plurality of arms is greater than 1N when measured after incubating the gastric residence system in an environment of pH 1.6 for 3 days.

In some embodiments of the gastric residence system, the pullout force required to separate the filament from the distal end of the first arm of the plurality of arms is less than 2N when measured after incubating the gastric residence system in an environment of pH 6.5 for 3 days.

In some embodiments of the gastric residence system, the distal end of each arm of the plurality of arms comprises an enteric material.

In some embodiments of the gastric residence system, the filament comprises one or more of an elastic polymer, a biosorbable polymer, and a plasticizer.

In some embodiments of the gastric residence system, the enteric material of the distal end of each arm comprises a polymer, an enteric polymer, a plasticizer, and an acid.

In some embodiments of the gastric residence system, the polymer comprises polycaprolactone or TPU.

In some embodiments of the gastric residence system, the enteric polymer comprises hydroxypropylmethylcellulose acetate succinate.

In some embodiments of the gastric residence system, the plasticizer comprises propylene glycol.

In some embodiments of the gastric residence system, the acid comprises stearic acid.

In some embodiments of the gastric residence system, the distal end of each arm comprises a notch and the filament is positioned within the notch of each distal end.

In some embodiments of the gastric residence system, the filament is secured by overlapping a first end of the filament and a second end of the filament within a first notch, and the first end and the second end are secured by enlarging the first end and the second end of the filament.

In some embodiments of the gastric residence system, each arm of the plurality of arms comprises a first segment comprising a first polymer composition and a second segment comprising a second polymer composition, wherein the first segment has a stiffness greater than a stiffness of the second segment, as measured using a 3-point bending test per ASTM D790.

In some embodiments of the gastric residence system, the force required to compress the gastric residence system into a configuration small enough to pass through an opening having a diameter of 20 mm is at least 1.2 times greater than the force required to compress a gastric residence system having arms comprising only a first polymer composition into a configuration small enough to pass through the opening, as measured using an iris testing mechanism.

In some embodiments of the gastric residence system, the first polymer composition comprises one or more of PCL, PLA, PLGA, HPMCAS, and TPU.

In some embodiments of the gastric residence system, the second polymer composition comprises one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, and a silicone.

In some embodiments of the gastric residence system, the second polymer composition comprises at least a polycaprolactone and a soluble material to form a material that softens upon exposure to an aqueous environment.

In some embodiments of the gastric residence system, the first segment is directly connected to the second segment of each arm of the plurality of arms.

In some embodiments of the gastric residence system, the first segment is connected to the second segment via a linker.

In some embodiments of the gastric residence system, the first segment comprises 20-50% of a length of at least the first arm of the plurality of arms, the length being measured from a proximal end of the first arm, the proximal end being proximate to the core, to a distal end of the first arm.

In some embodiments of the gastric residence system, the second segment comprises 50-80% of a length of at least the first arm of the plurality of arms, the length being measured from a proximal end of the first arm, the proximal end being proximate to the core, to a distal end of the first arm.

In some embodiments of the gastric residence system, a number of fatigue cycles required to break the gastric residence system is at least 25% greater than a number of fatigue cycles required to break a gastric residence system with arms comprising only a first polymer composition, as measured using a double funnel test.

In some embodiments of the gastric residence system, the gastric residence system is configured to be encapsulated with a capsule when the gastric residence system is in a folded configuration to form a gastric residence dosage form suitable for administering to a patient, and the gastric residence dosage form is configured to release the gastric residence system in a stomach of the patient, allowing the gastric residence to assume an open configuration.

In some embodiments of the gastric residence system, the gastric residence system is used to treat a patient.

In some embodiments of the gastric residence system, the patient is a human or a dog.

In some embodiments, a gastric residence system is provided, the gastric residence system comprising: a plurality of arms connected at a proximal end, the plurality of arms extending radially from the proximal end; and a filament circumferentially connecting a distal end of each arm of the plurality of arms.

In some embodiments of the gastric residence system, the gastric residence system comprises a core, wherein each arm of the plurality of arms is connected to the core at the proximal end of each arm.

In some embodiments of the gastric residence system, the plurality of arms comprises at least three arms.

In some embodiments of the gastric residence system, the plurality of arms is configured to be loaded with an active pharmaceutical ingredient.

In some embodiments of the gastric residence system, the plurality of arms comprises 40-60% loading of an active pharmaceutical ingredient.

In some embodiments of the gastric residence system, the gastric residence system comprises a plurality of linker components, wherein one linker component of the plurality of linker components connects one arm of the plurality of arms to the core.

In some embodiments of the gastric residence system, each linker component of the plurality of linker component degrades, dissolves, disassociates, or mechanically weakens in a gastric environment.

In some embodiments of the gastric residence system, the gastric residence system is configured to be folded during administration and is configured to assume an open configuration when in a patient's stomach.

In some embodiments of the gastric residence system, the core undergoes elastic deformation when the gastric residence system is in the folded configuration and recoils when the gastric residence system assumes the open configuration.

In some embodiments of the gastric residence system, the gastric residence system has a multi-armed star shape in the open configuration.

In some embodiments of the gastric residence system, the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

In some embodiments of the gastric residence system, the pullout force required to separate the filament from the distal end of a first arm of the plurality of arms is greater than 1N when measured after incubating the gastric residence system in an environment of pH 1.6 for 3 days.

In some embodiments of the gastric residence system, the pullout force required to separate the filament from the distal end of the first arm of the plurality of arms is less than 2N when measured after incubating the gastric residence system in an environment of pH 6.5 for 3 days.

In some embodiments of the gastric residence system, the distal end of each arm of the plurality of arms comprises an enteric material.

In some embodiments of the gastric residence system, the filament comprises one or more of an elastic polymer, a biosorbable polymer, and a plasticizer.

In some embodiments of the gastric residence system, the enteric material of the distal end of each arm comprises a polymer, an enteric polymer, a plasticizer, and an acid.

In some embodiments of the gastric residence system, the polymer comprises polycaprolactone or TPU.

In some embodiments of the gastric residence system, the enteric polymer comprises hydroxypropylmethylcellulose acetate succinate.

In some embodiments of the gastric residence system, the plasticizer comprises propylene glycol.

In some embodiments of the gastric residence system, the acid comprises stearic acid.

In some embodiments of the gastric residence system, the distal end of each arm comprises a notch and the filament is positioned within the notch of each distal end.

In some embodiments of the gastric residence system, the filament is secured by overlapping a first end of the filament and a second end of the filament within a first notch, and the first end and the second end are secured by one of knotting or heat flaring.

In some embodiments of the gastric residence system, each arm of the plurality of arms comprises a first segment comprising a first polymer composition and a second segment comprising a second polymer composition, wherein the first segment has a stiffness greater than a stiffness of the second segment, as measured using a 3-point bending test per ASTM D790.

In some embodiments of the gastric residence system, the force required to compress the gastric residence system into a configuration small enough to pass through an opening having a diameter of 20 mm is at least 1.2 times greater than the force required to compress a gastric residence system having arms comprising only a first polymer composition into a configuration small enough to pass through the opening, as measured using an iris testing mechanism.

In some embodiments of the gastric residence system, the first polymer composition comprises one or more of PCL, PLA, PLGA, HPMCAS, and TPU.

In some embodiments of the gastric residence system, the second polymer composition comprises one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, and a silicone.

In some embodiments of the gastric residence system, the second polymer composition comprises at least a polycaprolactone and a soluble material to form a material that softens upon exposure to an aqueous environment.

In some embodiments of the gastric residence system, the first segment is directly connected to the second segment of at least the first arm of the plurality of arms.

In some embodiments of the gastric residence system, the first segment is connected to the second segment through a linker component.

In some embodiments of the gastric residence system, the first segment comprises 20-50% of a length of at least the first arm, the length being measured from a proximal end of the first arm, the proximal end being proximate to the core, to a distal end of the first arm.

In some embodiments of the gastric residence system, the second segment comprises 50-80% of a length of the at least one arm, the length being measured from a proximal end of the at least one arm, the proximal end being proximate to the core, to a distal end of the at least one arm.

In some embodiments of the gastric residence system, a number of fatigue cycles required to break the gastric residence system is at least 25% greater than a number of fatigue cycles required to break a gastric residence system with arms comprising only a first polymer composition, as measured using a double funnel test.

In some embodiments of the gastric residence system, the gastric residence system is configured to be encapsulated with a capsule when the gastric residence system is in a folded configuration to form a gastric residence dosage form suitable for administering to a patient, and the gastric residence dosage form is configured to release the gastric residence system in a stomach of the patient, allowing the gastric residence to assume an open configuration.

In some embodiments of the gastric residence system, the gastric residence system is used to treat a patient.

In some embodiments of the gastric residence system, the patient is a human or a dog.

In some embodiments, a method of manufacturing a gastric residence system is provided, the method comprising: preparing gastric residence system comprising a plurality of arms connected to a core at a proximal end through a plurality of linker components, one linker component of the plurality of linker components corresponding to each arm of the plurality of arms, and the plurality of arms extending radially; notching each arm of the plurality of arms to form a notch in each arm; wrapping a filament circumferentially around the gastric residence system such that the filament is positioned within each notch of each arm; and closing each notch to secure the filament within each notch.

In some embodiments of the method, the filament circumferentially connects a distal end of each arm of the plurality of arms.

In some embodiments of the method, the plurality of arms comprises at least three arms.

In some embodiments of the method, the plurality of arms is configured to be loaded with an active pharmaceutical ingredient.

In some embodiments of the method, the plurality of arms comprises 40-60% loading of an active pharmaceutical ingredient.

In some embodiments of the method, the linker component degrades, dissolves, disassociates, or mechanically weakens in a gastric environment.

In some embodiments of the method, the gastric residence system is configured to be folded during administration and is configured to assume an open configuration when in a patient's stomach.

In some embodiments of the method, the core undergoes elastic deformation when the gastric residence system is in the folded configuration and recoils when the gastric residence system assumes the open configuration.

In some embodiments of the method, the gastric residence system has a multi-armed star shape in the open configuration.

In some embodiments of the method, closing each notch comprises at least one of knotting or heating.

In some embodiments of the method, the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

In some embodiments of the method, the pullout force required to separate the filament from the distal end of a first arm of the plurality of arms is greater than 1N when measured after incubating the gastric residence system in an environment of pH 1.6 for 3 days.

In some embodiments of the method, the pullout force required to separate the filament from the distal end of the first arm of the plurality of arms is less than 2N when measured after incubating the gastric residence system in an environment of pH 6.5 for 3 days.

In some embodiments of the method, the distal end of each arm of the plurality of arms comprises an enteric material.

In some embodiments of the method, the filament comprises one or more of an elastic polymer, a biosorbable polymer, and a plasticizer.

In some embodiments of the method, the enteric material of the distal end of each arm comprises a polymer, an enteric polymer, a plasticizer, and an acid.

In some embodiments of the method, the polymer comprises polycaprolactone.

In some embodiments of the method, the enteric polymer comprises hydroxypropylmethylcellulose acetate succinate.

In some embodiments of the method, the plasticizer comprises propylene glycol.

In some embodiments of the method, the acid comprises stearic acid.

In some embodiments of the method, each arm of the plurality of arms comprises a first segment comprising a first polymer composition and a second segment comprising a second polymer composition, wherein the first segment has a stiffness greater than a stiffness of the second segment, as measured using a 3-point bending test per ASTM D790.

In some embodiments of the method, the force required to compress the gastric residence system into a configuration small enough to pass through an opening having a diameter of 20 mm is at least 1.2 times greater than the force required to compress a gastric residence system having arms comprising only a first polymer composition into a configuration small enough to pass through the opening, as measured using an iris testing mechanism.

In some embodiments of the method, the first polymer composition comprises one or more of PCL, PLA, PLGA, HPMCAS, and TPU.

In some embodiments of the method, the second polymer composition comprises one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, and a silicone.

In some embodiments of the method, the second polymer composition comprises at least a polycaprolactone and a soluble material to form a material that softens upon exposure to an aqueous environment.

In some embodiments of the method, the first segment is directly connected to the second segment of the at least one arm.

In some embodiments of the method, the first segment is connected to the second segment through a linker component.

In some embodiments of the method, the first segment comprises 20-50% of a length of the at least one arm, the length being measured from a proximal end of the at least one arm, the proximal end being proximate to the core, to a distal end of the at least one arm.

In some embodiments of the method, the second segment comprises 50-80% of a length of the at least one arm, the length being measured from a proximal end of the at least one arm, the proximal end being proximate to the core, to a distal end of the at least one arm.

In some embodiments of the method, a number of fatigue cycles required to break the gastric residence system is at least 25% greater than a number of fatigue cycles required to break a gastric residence system with arms comprising only a first polymer composition, as measured using a double funnel test.

In some embodiments of the method, the gastric residence system is configured to be encapsulated with a capsule when the gastric residence system is in a folded configuration to form a gastric residence dosage form suitable for administering to a patient, and the gastric residence dosage form is configured to release the gastric residence system in a stomach of the patient, allowing the gastric residence to assume an open configuration.

In some embodiments of the method, the gastric residence system is used to treat a patient.

In some embodiments of the method, the patient is a human or a dog.

In some embodiments, a method of manufacturing a gastric residence system is provided, the method comprising: preparing a gastric residence system comprising a plurality of arms connected to a core at a proximal end through a plurality of linker components, one linker component of the plurality of the plurality of linker components corresponding to each arm of the plurality of arms, and the plurality of arms extending radially; preparing a plurality of tips and a filament, one tip for each arm of the plurality of arms, wherein the filament is attached to each tip of the plurality of tips; connecting each tip of the plurality of tips to an arm of the plurality of arms to form a gastric residence system comprising a filament.

In some embodiments of the method, preparing a plurality of tips and a filament comprises injection molding.

BRIEF DESCRIPTION OF THE DRAWINGS

The invention will now be described, by way of example only, with reference to the accompanying drawings, in which.

DETAILED DESCRIPTION OF THE INVENTION

Figure 1A:
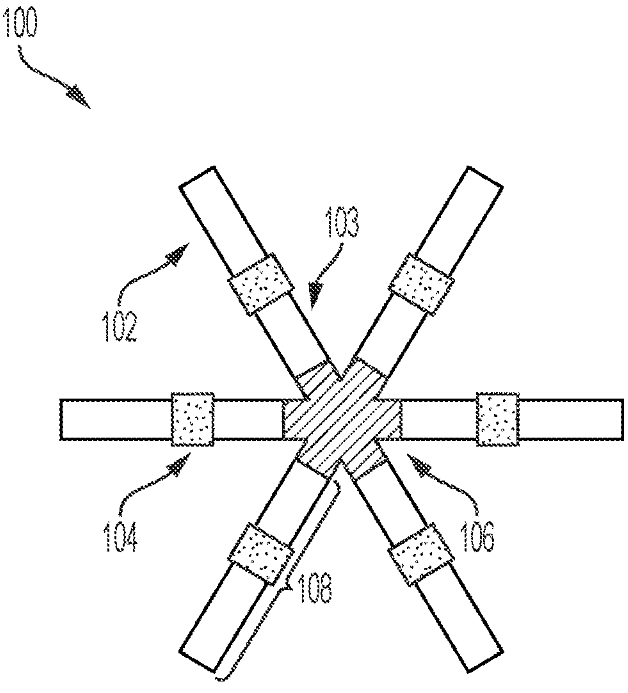
FIGS. 1A-1C show various gastric residence system configurations, according to some embodiments.

Described herein are gastric residence systems having a filament and methods of preparing gastric residence systems having a filament. As described above, gastric residence systems are designed to reside in the gastrointestinal tract for a predetermined amount of time. After a period of time (e.g., the predetermined residence time), the gastric residence system breaks down into several pieces small enough to pass through the pylorus. However, if the gastric residence system bends into a configuration small enough to prematurely pass through the pylorus of a patient, the therapeutic agent of the gastric residence system is not properly administered to the patient.

Accordingly, gastric residence systems provided herein comprise a filament connecting the distal ends of each of the arms of the gastric residence system. This filament can help prevent a gastric residence system from passing through the pylorus before the predetermined residence time has expired.

Gastric residence systems are typically administered in a folded, closed, or collapsed configuration. When the gastric residence system enters the patient's stomach, it unfolds to assume an open configuration. The physical opening or unfolding of the gastric residence system results in a dosage form with an effective size (i.e., a gastric residence system in an open configuration) that is too large to pass through the patient's pyloric valve (i.e., opening between the stomach and the small intestine). The deployed, or expanded, gastric residence system can stay in the patient's stomach for a predetermined period of time (e.g., 24 hours, 48 hours, 7 days, 10 days, etc.).

However, one challenge in particular with gastric residence systems is ensuring a consistent and accurate residence time. A gastric residence system that passes through the pylorus too early fails to administer the intended amount of therapeutic agent, compromising the efficacy and reliability of the gastric residence system.

Accordingly, gastric residence systems provided herein are designed for more consistent and accurate residence times in a patient's stomach. In particular, gastric residence systems comprising a filament provided herein are more likely to resist premature passage through the pylorus. Thus, gastric residence systems provided herein are more likely to deliver consistent and accurate residence times, improving the efficacy and reliability of the gastric residence system.

Definitions

As used herein, "gastric residence system" is a dosage form comprising a therapeutic agent and is configured to be administered to a patient in a folded configuration. A "gastric residence dosage form" comprises a folded gastric residence system and is configured to hold the gastric residence system in a folded configuration until deployment. For example, a gastric residence dosage form may comprise a capsule and/or a capsule coating according to those described in U.S. Appln. No. 62/821,352 titled "Capsules and Capsule Coatings for Gastric Residence Dosage Forms" and/or U.S. Appln. No. 62/821,361 titled "Coatings for Gastric Residence Forms."

A "carrier polymer" is a polymer suitable for blending with an agent, such as a drug, for use in the invention.

An "agent" is any substance intended for therapeutic, diagnostic, or nutritional use in a patient, individual, or subject. Agents include, but are not limited to, drugs, nutrients, vitamins, and minerals.

A "dispersant" is defined as a substance which aids in the minimization of particle size of agent and the dispersal of agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of agent particles in the carrier polymer matrix.

An "excipient" is any substance added to a formulation of an agent that is not the agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" (also referred to as a "tensile polymer") is a polymer that is capable of being deformed by an applied force from its original shape for a period of time, and which then substantially returns to its original shape once the applied force is removed.

A "coupling polymer" is a polymer suitable for coupling any other polymers together, such as coupling a first carrier polymer-agent component to a second carrier polymer-agent component. Coupling polymers typically form the linker regions between other components.

A "time-dependent polymer" or "time-dependent coupling polymer" is a polymer that degrades in a time-dependent manner when a gastric residence system is deployed in the stomach. A time-dependent polymer is typically not affected by the normal pH variations in the stomach.

"Approximately constant plasma level" refers to a plasma level that remains within a factor of two of the average plasma level (that is, between 50% and 200% of the average plasma level) measured over the period that the gastric residence system is resident in the stomach.

"Substantially constant plasma level" refers to a plasma level that remains within plus-or-minus 25% of the average plasma level measured over the period that the gastric residence system is resident in the stomach.

A "hydrophilic therapeutic agent," "hydrophilic agent," or "hydrophilic drug" is an agent which readily dissolves in water. A hydrophilic agent is defined as an agent which has a solubility in water of 1 mg/ml or greater. Alternatively, a hydrophilic agent can be defined as an agent which has a log Poct (log partition coefficient Poct, where Poct=(concentration in 1-octanol)/(concentration in $H_2O$)) in a 1-octanol/water system of less than 0.5. The pH at which solubility or log Poct is measured is 1.6, approximating the gastric environment.

A "hydrophobic therapeutic agent," "hydrophobic agent," or "hydrophobic drug" is an agent which does not readily dissolve in water. A hydrophobic agent is defined as an agent which has a solubility in water of less than 1 mg/ml. Alternatively, a hydrophobic agent can be defined as an agent which has a log Poct (log partition coefficient) in a 1-octanol/water system of greater than 1. Alternatively, a hydrophobic therapeutic agent can be defined as an agent which has a higher solubility in ethanol than in water. Alternatively, a hydrophobic therapeutic agent can be defined as an agent which has a higher solubility in 40% ethanol/60% simulated gastric fluid than in 100% simulated gastric fluid.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

A "patient," "individual," or "subject" refers to a mammal, preferably a human or a domestic animal such as a dog or cat. In a most preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods of the invention can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent, such as a drug, is an amount of the agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of an agent is an amount of the agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

A "flexural modulus" of a material is an intrinsic property of a material computed as the ratio of stress to strain in flexural deformation of the material as measured by a 3-point bending test. Although the linkers are described herein as being components of the gastric residence system, the flexural modulus of the material of the polymeric material may be measured in isolation. For example, the polymeric linker in the gastric residence system may be too short to measure the flexural modulus, but a longer sample of the same material may be used to accurately determine the flexural modulus. The longer sample used to measure the flexural modulus should have the same cross-sectional dimensions (shape and size) as the polymeric linker used in the gastric residence system. The flexural modulus is measured using a 3-point bending test in accordance with the ASTM standard 3-point bending test (ASTM D790) using a 10 mm distance between supports and further modified to accommodate materials with non-rectangular cross-sections. The longest line of symmetry for the cross section of the polymeric linker should be positioned vertically, and the flexural modulus should be measured by applying force downward. If the longest line of symmetry for the cross section of the polymeric linker is perpendicular to a single flat edge, the single flat edge should be positioned upward. If the cross-section of the polymeric linker is triangular, the apex of the triangle should be faced downward. As force is applied downward, force and displacement are measured, and the slope at the linear region is obtained to calculate the flexural modulus.

As used herein, the singular forms "a", "an", and "the" include plural references unless indicated otherwise or the context clearly dictates otherwise.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component may be combined with any disclosed lower limit for that component to provide a range (provided that the upper limit is greater than the lower limit with which it is to be combined). Each of these combinations of disclosed upper and lower limits are explicitly envisaged herein. For example, if ranges for the amount of a particular component are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Partitioning behavior of an agent can be measured between a polycaprolactone phase (PCL phase) and a simulated gastric fluid phase (SGF phase), to give the partition coefficient PPCL-SGF between the two phases for the agent. Log PPCL-SGF can also be calculated. A 5:1 mixture of polycaprolactone diol (MW 530):ethyl acetate can be used as the PCL phase, and fasted-state simulated gastric fluid (FaSSGF) can be used as the SGF phase, such that PPCL-SGF=(concentration in polycaprolactone diol)/(concentration in FaSSGF)).

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

In addition to the embodiments and methods disclosed here, additional embodiments of gastric residence systems, and methods of making and using such systems, are disclosed in International Patent Application Nos. WO 2015/191920, WO 2015/191925, WO 2017/070612, WO 2017/100367, and PCT/US2017/034856, which are incorporated by reference herein in their entirety.

Gastric Residence Systems

Provided herein are arms of gastric residence systems and segments for use in gastric residence systems, which can include a filament to help prevent early passage of the gastric residence system through the pylorus. Following is a description of an overall gastric residence system configuration and a detailed description of each of the three main components of a gastric residence system: an elastomer (i.e., central elastomer or core), arms (i.e., elongate members, carrier polymers, or carrier polymer-agent components), and coupling polymers (i.e., linker, linker region, or linker component). More specifically, described herein is: Overall system configuration; System dimensions; Residence time; Evaluation of release characteristics; Gastric Delivery Pharmacokinetics for Gastric Residence Systems; Dissolution Profile, Bioavailability, and Pharmacokinetics for Gastric Residence System; Elastomers; Carrier polymers for segments and arms (carrier polymer-agent component); Carrier polymer-agent/agent salt combinations with excipients and other additives; Agents for use in gastric residence systems; High agent loading of arms and segments; Dispersants for modulation of agent release and stability of polymer blend; Stabilizers for use in gastric residence systems; Coupling polymers; Filaments for Improved Gastric Residence; Gastric residence systems comprising arms of controlled stiffness; and System polymeric composition.

Gastric residence dosage forms can be designed to be administered to the stomach of a patient by swallowing, by feeding tube, by gastric tube, etc. Once a gastric residence dosage form is in place in the stomach, it can remain in the stomach for a desired residence time (e.g., three days, seven days, two weeks, etc.). A gastric residence dosage form that is properly in place in a stomach will resist passage through the pyloric valve, which separates the stomach from the small intestine. Gastric residence dosage forms can release a therapeutic agent (i.e., API or drug) over the period of residence with controlled release. While residing in the stomach, the dosage form may not interfere with the normal passage of food or other gastric contents. Once the desired residence time has expired, the dosage form passes out of the stomach (i.e., through the pyloric valve) and is readily eliminated from the patient.

To administer a gastric residence system to a patient, the gastric residence system can be folded into a form small enough to be swallowed or otherwise administered. In some embodiments, the folded gastric residence system is retained in a capsule or other container which can be swallowed by the patient. In some cases, the gastric residence system may be delivered to a patient via gastrostomy tube, feeding tube, gastric tube, or other route of administration to the stomach. Specific examples of gastric residence systems may be found in PCT/US2018/051816, WO 2015/191920, WO 2017/070612, WO 2017/100367, WO 2018/064630, WO 2017/205844, WO 2018/227147, each of which is incorporated herein in its entirety.

Once the gastric residence system reaches the stomach of a patient, it may assume an open configuration. The dimensions of an open gastric residence system are, when left unaltered, suitable to prevent passage of the device through the pyloric valve for the period of time during which the device is intended to reside in the stomach. In some embodiments, the folded gastric residence system can also be secured by a dissolvable retaining band or sleeve that can prevent premature deployment of the gastric residence system in case of a failure of the capsule. A gastric residence system folded and retained in a folded configuration with a sleeve or band may be encapsulated by a capsule. In some embodiments of the gastric residence dosage form, the sleeve comprises at least one of gelatin, hydroxypropyl methylcellulose, or pullulan. In some embodiments of the gastric residence dosage form, the capsule comprises at least one of gelatin, hydroxypropyl methylcellulose, or pullulan. Thus, in one embodiment, a gastric residence system comprises a core; a plurality of arms connected to the core at a proximal end through a plurality of linker components, one linker component of the plurality of linker components corresponding to each arm of the plurality of arms, and the plurality of arms extending radially from the proximal end; and a filament circumferentially connecting each arm of the plurality of arms. The gastric residence system can further comprise a sleeve, wherein the sleeve surrounds at least a portion of the gastric residence system in the folded configuration. The gastric residence system can further comprise a capsule encapsulating the gastric residence system in the folded configuration. The gastric residence system can further comprise a sleeve, wherein the sleeve surrounds at least a portion of the gastric residence system in the folded configuration, and can further comprise a capsule encapsulating the gastric residence system in the folded configuration. In any of these embodiments, the sleeve can comprise at least one of gelatin, hydroxypropyl methylcellulose, or pullulan. In any of these embodiments, the capsule can comprise at least one of gelatin, hydroxypropyl methylcellulose, or pullulan. In any of these embodiments, the sleeve can comprise at least one of gelatin, hydroxypropyl methylcellulose, or pullulan, and the capsule can comprise at least one of gelatin, hydroxypropyl methylcellulose, or pullulan.

While in the stomach, the gastric residence system is compatible with digestion and other normal functioning of the stomach or gastrointestinal tract. The gastric residence system does not interfere with or impede the passage of chyme (partially digested food) or other gastric contents which exit the stomach through the pyloric valve into the duodenum.

Once released from the capsule into the stomach, the therapeutic agent of the gastric residence system begins to take effect. In some embodiments, the gastric residence system comprises a plurality of carrier polymer-agent components. The carrier polymer-agent components may comprise a carrier polymer, a pore former, and a therapeutic agent (or a salt thereof). The plurality of carrier polymer-agent components are linked together by one or more coupling polymer components. The therapeutic agent may be eluted from the carrier polymer-agent components into the gastric fluid of the patient over the desired residence time of the system. Release of the therapeutic agent is controlled by appropriate formulation of the carrier polymer-agent components, including by the use of the dispersant in formulation of the carrier polymer-agent components, and by milling of the therapeutic agent to particles of desired size prior to blending the agent with the carrier polymer and dispersant.

Additionally, coatings can be applied to outer surfaces of the gastric residence system. The coatings can include additional therapeutic agents or agents that can affect the release of therapeutic agents or the residence duration of the gastric residence system.

Once the desired residence time has expired, the gastric residence system passes out of the stomach. To do so, various components of the gastric delivery system are designed to weaken and degrade. The specific dimensions of the system are also taken into consideration. In its intact, open configuration, the gastric residence system is designed to resist passage through the pyloric valve. However, coupling polymer components of the gastric residence system are chosen such that they gradually degrade over the specified residence period in the stomach. When the coupling polymer components are sufficiently weakened by degradation, the gastric residence system loses critical resilience to compression or size reduction and can break apart into smaller pieces. The reduced-size dosage form and any smaller pieces are designed to pass through the pyloric valve. The system then passes through the intestines and is eliminated from the patient. In some embodiments, a gastric residence system may be designed to weaken at specific locations such that the gastric residence system can pass through a pyloric valve intact once the residence time expires without degrading into numerous smaller pieces.

Overall System Configuration

Figure 1B:
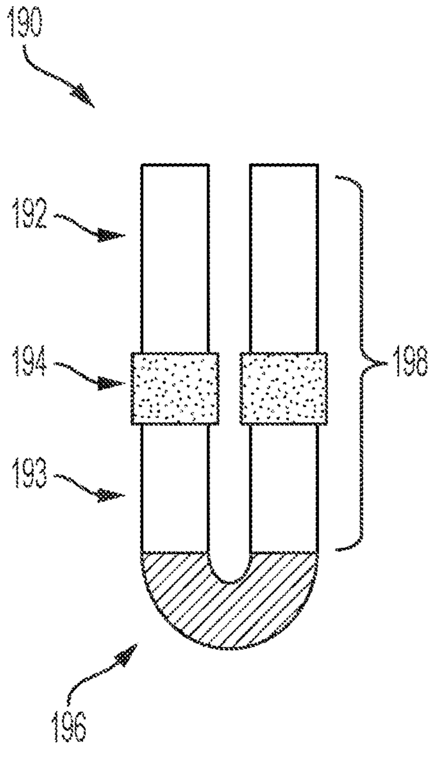

Gastric residence systems can be prepared in different configurations. The "stellate" configuration of a gastric residence system is also known as a "star" (or "asterisk") configuration. An example of a stellate system 100 is shown schematically in FIG. 1A. Multiple arms (only one such arm, 108, is labeled for clarity), are affixed to disk-shaped central elastomer 106. The arms depicted in FIG. 1A are comprised of segments 102 and 103, joined by a coupling polymer or linker region 104 (again, the components are only labeled in one arm for clarity) which serves as a linker region. This configuration permits the system to be folded or compacted at the central elastomer. FIG. 1B shows a folded configuration 190 of the gastric residence system of FIG. 1A (for clarity, only two arms are illustrated in FIG. 1B). Segments 192 and 193, linker region 194, elastomer 196, and arm 198 of FIG. 1B correspond to segments 102 and 103, linker region 104, elastomer 106, and arm 108 of FIG. 1A, respectively. When folded, the overall length of the system is reduced by approximately a factor of two, and the system can be conveniently placed in a container such as a capsule or other container suitable for oral administration. When the capsule reaches the stomach, the capsule dissolves, releasing the gastric residence system. The gastric residence system then unfolds into its uncompacted state, which is retained in the stomach for the desired residence period.

While the linker regions 104 are shown as slightly larger in diameter than the segments 102 and 103 in FIG. 1A, they can be the same diameter as the segments, so that the entire arm 102-104-103 has a smooth outer surface.

In some embodiments, the stellate system may have an arm composed of only one segment, which is attached to the central elastomer by a linker region. This corresponds to FIG. 1A with the segments 103 omitted. The single-segment arms comprising segments 102 are then directly attached to central elastomer 106 via the linkers 104. The linkers can comprise a coupling polymer or a disintegrating matrix.

A stellate system can be described as a gastric residence system for administration to the stomach of a patient, comprising an elastomer component, and a plurality of at least three carrier polymer-agent components comprising a carrier polymer and an agent or a salt thereof, attached to the elastomer component, wherein each of the plurality of carrier polymer-agent components is an arm comprising a proximal end, a distal end, and an outer surface therebetween; wherein the proximal end of each arm is attached to the elastomer component and projects radially from the elastomer component, each arm having its distal end not attached to the elastomer component and located at a larger radial distance from the elastomer component than the proximal end; wherein each arm independently comprises one or more segments, each segment comprising a proximal end, a distal end, and an outer surface therebetween. In some embodiments, when two or more segments are present in an arm, each segment is attached to an adjacent segment via a linker region. In some embodiments, when two or more segments are present in an arm, one segment is directly attached to the other segment, without using a linker region. The linker region can be a coupling polymer or a disintegrating matrix. The arms can be attached to the central elastomer via a coupling polymer or a disintegrating matrix, and can have intervening portions of interfacing polymers. For the plurality of at least three arms, or for a plurality of arms, a preferred number of arms is six, but three, four, five, seven, eight, nine, or ten arms can be used. The arms should be equally spaced around the central elastomer; if there are N arms, there will be an angle of about 360/N degrees between neighboring arms.

Figure 1C:
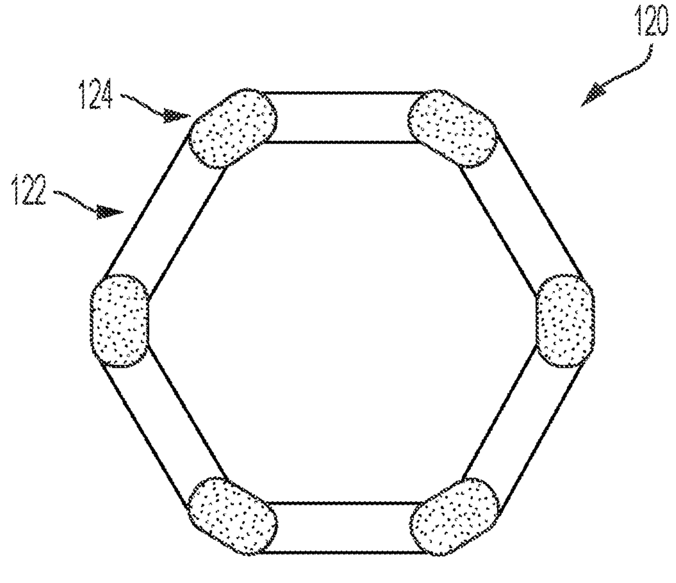

FIG. 1C shows another possible overall configuration 120 for a gastric residence system, which is a ring configuration. Segments 122 are joined by coupling polymer or linker region 124 (only one segment and one coupling linkage are labeled for clarity). The coupling polymer/linker region in this design must also function as an elastomer, to enable the ring to be twisted into a compacted state for placement in a container, such as a capsule.

In one embodiment of the stellate configuration, the segments 102 and 103 comprise a carrier polymer blended with an agent or drug. In one embodiment of the ring configuration, the segments 122 comprise a carrier polymer blended with an agent or drug.

The coupling polymers of the gastric residence system, which serve as linker regions, are designed to break down gradually in a controlled manner during the residence period of the system in the stomach. If the gastric residence system passes prematurely into the small intestine in an intact form, the system is designed to break down much more rapidly to avoid intestinal obstruction. This is readily accomplished by using enteric polymers as coupling polymers. Enteric polymers are relatively resistant to the acidic pH levels encountered in the stomach, but dissolve rapidly at the higher pH levels found in the duodenum. Use of enteric coupling polymers as safety elements protects against undesired passage of the intact gastric residence system into the small intestine. The use of enteric coupling polymers also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient. In the system shown in FIG. 1A, at least the coupling polymer used for the couplings 104 are made from such enteric polymers.

In additional embodiments, a time-dependent coupling polymer or linker can be used. Such a time-dependent coupling polymer or linker degrades in a predictable, time-dependent manner. In some embodiments, the degradation of the time-dependent coupling polymer or linker may not be affected by the varying pH of the gastrointestinal system.

In additional embodiments, different types of linkers can be used in the gastric residence systems. That is, both enteric linkers (or enteric coupling polymers) and time-dependent linkers (or time-dependent coupling polymers) can be used. In some embodiments, a single mutli-segment arm of a stellate system can use both an enteric linker at some linker regions between segments, and a time-dependent linker at other linker regions between segments.

Linker regions are typically about 100 microns to about 2 millimeter in width, such as about 200 um to about 2000 um, about 300 um to about 2000 um, about 400 um to about 2000 um, about 500 um to about 2000 um, about 600 um to about 2000 um, about 700 um to about 2000 um, about 800 um to about 2000 um, about 900 um to about 2000 um, about 1000 um to about 2000 um, about 1100 um to about 2000 um, about 1200 um to about 2000 um, about 1300 um to about 2000 um, about 1400 um to about 2000 um, about 1500 um to about 2000 um, about 1600 um to about 2000 um, about 1700 um to about 2000 um, about 1800 um to about 2000 um, or about 1900 um to about 2000 um; or about 100 um to about 1900 um, about 100 um to about 1800 um, about 100 um to about 1700 um, about 100 um to about 1600 um, about 100 um to about 1500 um, about 100 um to about 1400 um, about 100 to about 1300 um, about 100 um to about 1200 um, about 100 um to about 1100 um, about 100 um to about 1000 um, about 100 um to about 900 um, about 100 um to about 800 um, about 100 um to about 700 um, about 100 um to about 600 um, about 100 um to about 500 um, about 100 um to about 400 um, about 100 um to about 300 um, or about 100 um to about 200 um. Linker regions can be about 100 um, about 200 um, about 300 um, about 400 um, about 500 um, about 600 um, about 700 um, about 800 um, about 900 um, about 1000 um, about 1100 um, about 1200 um, about 1300 um, about 1400 um, about 1500 um, about 1600 um, about 1700 um, about 1800 um, about 1900 um, or about 200o um in width, where each value can be plus or minus 50 um (±50 um).

The central elastomeric polymer of a stellate system is typically not an enteric polymer; however, the central elastomeric polymer can also be made from such an enteric polymer where desirable and practical.

The central elastomer should have a specific durometer and compression set. The durometer is important because it determines the folding force of the dosage form and whether it will remain in the stomach; a preferred range is from about 60 to about 90 A. The compression set should be as low as possible to avoid having permanent deformation of the gastric residence system when stored in the capsule in its compacted configuration. A preferred range is about 10% to about 20% range. Materials that fit these requirements are the QP1 range of liquid silicone rubbers from Dow Corning. In any embodiment with a central elastomer, the QP1-270 (70 A durometer) liquid silicone rubber can be used. In some embodiments, the central elastomer may comprise a 50 A or 60 A durometer liquid silicone rubber (Shin Etsu).

Segments and arms of the gastric residence systems can have cross-sections in the shape of a circle (in which case the segments are cylindrical), a polygon (such as segments with a triangular cross-section, rectangular cross-section, or square cross-section), or a pie-shaped cross-section (in which case the segments are cylindrical sections). Segments with polygon-shaped or pie-shaped cross-sections, and ends of cylindrically-shaped sections which will come into contact with gastric tissue, can have their sharp edges rounded off to provide rounded corners and edges, for enhanced safety in vivo. That is, instead of having a sharp transition between intersecting edges or planes, an arc is used to transition from one edge or plane to another edge or plane. Thus, a "triangular cross-section" includes cross-sections with an approximately triangular shape, such as a triangle with rounded corners. An arm with a triangular cross-section includes an arm where the edges are rounded, and the corners at the end of the arm are rounded. Rounded corners and edges are also referred to as fillet corners, filleted corners, fillet edges, or filleted edges.

However, it has been demonstrated that gastric residence systems of a stellate shape can bend into a configuration that allows for premature passage through the pylorus of a patient. Gastric residence systems that prematurely pass through the pylorus fail to deliver the therapeutic agent of the gastric residence system to the patient. Further, premature passage causes inconsistency, causes unreliability, and compromises the efficacy of the gastric residence system.

Figure 2:
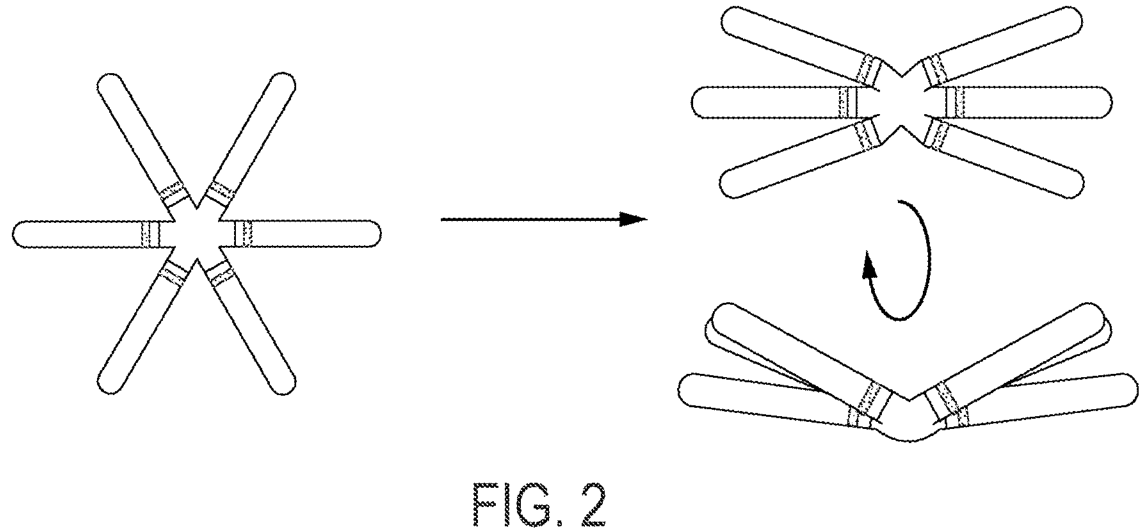
FIG. 2 shows a gastric residence system comprising a plurality of arms and the bent geometry a gastric residence can assume most easily when compressed by forces such as gastric contractions, according to some embodiments.

FIG. 2 shows a stellate-shaped gastric residence system having a plurality of arms. One example of a bended configuration is shown on the right side of the Figure. Due to forces in the stomach (e.g., peristaltic forces), gastric residence systems may bend into configurations, such as that shown in FIG. 2, that can allow for premature passage through the pylorus.

Figures 3A, 3B, 3C:
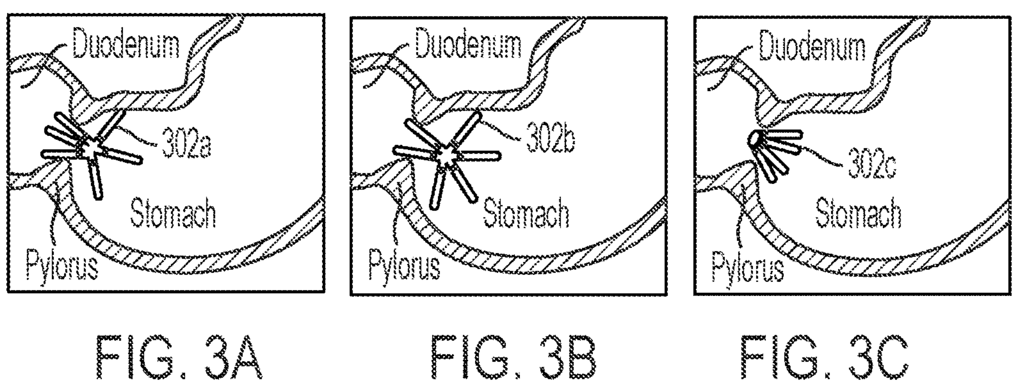
FIG. 3A-3C show various methods by which a gastric residence system may pass through a pylorus prior to dissolving, according to some embodiments.

Other possible bended configurations are shown in FIGS. 3A-3C. Specifically, FIGS. 3A-3C show three different configurations that a gastric residence system may assume that can allow for premature passage through the pylorus. As shown in each Figure, the relatively stiff arms of the gastric residence system remain straight. However, because the core of each of the gastric residence systems has a higher flexibility than the arms, the core can bend. The bending of the core can allow gastric residence systems having relatively stiff arms to prematurely pass through the pylorus of a patient.

As shown in FIG. 3A, gastric residence system 302*a* is shown in a bended configuration having three arms leading through the pyloric opening. FIG. 3B shows gastric residence system 302*b* in a bended configuration having two arms leading through the pyloric opening. FIG. 3C shows gastric residence system 302*c* in a bended configuration analogous to the shape of a shuttlecock and having the core leading through the pyloric opening.

Accordingly, described herein are gastric residence systems comprising a filament. A filament wrapped circumferentially around a gastric residence system and connecting the arms of the gastric residence system, for example, can help prevent premature passage through a patient's pylorus. Filaments and gastric residence systems comprising filaments are described in more detail with respect to the arms and coupling polymers of a gastric residence system.

System Dimensions

The system must be able to adopt a compacted state with dimensions that enable the patient to swallow the system (or for the system to be introduced into the stomach by alternate means, such as a feeding tube or gastrostomy tube). Typically, the system is held in the compacted state by a container such as a capsule. Upon entry into the stomach, the system is then released from the container and adopts an uncompacted state, that is, an expanded conformation, with dimensions that prevent passage of the system through the pyloric sphincter, thus permitting retention of the system in the stomach.

Accordingly, the system should be capable of being placed inside a standard-sized capsule of the type commonly used in pharmacy. Standard capsule sizes in use in the United States are provided below in the Capsule Table below (see "Draft Guidance for Industry on Size, Shape, and Other Physical Attributes of Generic Tablets and Capsules" at URL www.regulations.gov/#!documentDetail;D=FDA-2013-N-1434-0002). As these are the outer dimensions of the capsule, and as dimensions will vary slightly between capsule manufacturers, the system should be capable of adopting a configuration which is about 0.5 to 1 mm smaller than the outer diameter shown, and about 1 to 2 mm shorter than the length shown in the Capsule Table.

Capsule Table

| Capsule Size | Outer Diameter (mm) | Length (mm) |
|---|---|---|
| 000 | 9.9 | 26.1 |
| 00 | 8.5 | 23.3 |
| 0 | 7.6 | 21.7 |
| 1 | 6.9 | 19.4 |
| 2 | 6.3 | 18.0 |
| 3 | 5.8 | 15.9 |
| 4 | 5.3 | 14.3 |
| 5 | 4.9 | 11.1 |

Capsules can be made of materials well-known in the art, such as gelatin or hydroxypropyl methylcellulose. In one embodiment, the capsule is made of a material that dissolves in the gastric environment, but not in the oral or esophageal environment, which prevents premature release of the system prior to reaching the stomach.

In one embodiment, the system will be folded or compressed into a compacted state in order to fit into the capsule, for example, in a manner such as that shown in FIG. 1B. Once the capsule dissolves in the stomach, the system will adopt a configuration suitable for gastric retention, for example, in a manner such as that shown in FIG. 1A. Preferred capsule sizes are 00 and 00e1 (a 00e1-size capsule has the approximate length of a 000 capsule and the approximate width of a 00 capsule), which then places constraints on the length and diameter of the folded system.

Once released from the container, the system adopts an uncompacted state with dimensions suitable to prevent passage of the gastric residence system through the pyloric sphincter. In one embodiment, the system has at least two perpendicular dimensions, each of at least 2 cm in length; that is, the gastric residence system measures at least about 2 cm in length over at least two perpendicular directions. In another embodiment, the perimeter of the system in its uncompacted state, when projected onto a plane, has two perpendicular dimensions, each of at least 2 cm in length. The two perpendicular dimensions can independently have lengths of from about 2 cm to about 7 cm, about 2 cm to about 6 cm, about 2 cm to about 5 cm, about 2 cm to about 4 cm, about 2 cm to about 3 cm, about 3 cm to about 7 cm, about 3 cm to about 6 cm, about 3 cm to about 5 cm, about 3 cm to about 4 cm, about 4 cm to about 7 cm, about 4 cm to about 6 cm, about 4 cm to about 5 cm, or about 4 cm to about 4 cm. These dimensions prevent passage of the gastric residence system through the pyloric sphincter. For star-shaped polymers with N arms (where N is greater than or equal to three, such as N=6), the arms can have dimensions such that the system has at least two perpendicular dimensions, each of length as noted above. These two perpendicular dimensions are chosen as noted above in order to promote retention of the gastric residence system.

The system is designed to eventually break apart in the stomach at the end of the desired residence time (residence period), at which point the remaining components of the system are of dimensions that permit passage of the system through the pyloric sphincter, small intestine, and large intestine. Finally, the system is eliminated from the body by defecation, or by eventual complete dissolution of the system in the small and large intestines. Thus, coupling polymers or disintegrating matrices are placed in the gastric residence systems of the invention in a configuration such that, at the end of the desired residence period when the coupling polymers or disintegrating matrices break or dissolve, the uncoupled components of the gastric residence system have dimensions suitable for passage through the pyloric sphincter and elimination from the digestive tract.

Residence Time

The residence time of the gastric residence system is defined as the time between administration of the system to the stomach and exit of the system from the stomach. In one embodiment, the gastric residence system has a residence time of about 24 hours, or up to about 24 hours. In one embodiment, the gastric residence system has a residence time of about 48 hours, or up to about 48 hours. In one embodiment, the gastric residence system has a residence time of about 72 hours, or up to about 72 hours. In one embodiment, the gastric residence system has a residence time of about 96 hours, or up to about 96 hours. In one embodiment, the gastric residence system has a residence time of about 5 days, or up to about 5 days. In one embodiment, the gastric residence system has a residence time of about 6 days, or up to about 6 days. In one embodiment, the gastric residence system has a residence time of about 7 days (about one week), or up to about 7 days (about one week). In one embodiment, the gastric residence system has a residence time of about 10 days, or up to about 10 days. In one embodiment, the gastric residence system has a residence time of about 14 days (about two weeks), or up to about 14 days (about two weeks).

In one embodiment, the gastric residence system has a residence time between about 24 hours and about 7 days. In one embodiment, the gastric residence system has a residence time between about 48 hours and about 7 days. In one embodiment, the gastric residence system has a residence time between about 72 hours and about 7 days. In one embodiment, the gastric residence system has a residence time between about 96 hours and about 7 days. In one embodiment, the gastric residence system has a residence time between about 5 days and about 7 days. In one embodiment, the gastric residence system has a residence time between about 6 days and about 7 days.

In one embodiment, the gastric residence system has a residence time between about 24 hours and about 10 days. In one embodiment, the gastric residence system has a residence time between about 48 hours and about 10 days. In one embodiment, the gastric residence system has a residence time between about 72 hours and about 10 days. In one embodiment, the gastric residence system has a residence time between about 96 hours and about 10 days. In one embodiment, the gastric residence system has a residence time between about 5 days and about 10 days. In one embodiment, the gastric residence system has a residence time between about 6 days and about 10 days. In one embodiment, the gastric residence system has a residence time between about 7 days and about 10 days.

In one embodiment, the gastric residence system has a residence time between about 24 hours and about 14 days. In one embodiment, the gastric residence system has a residence time between about 48 hours and about 14 days. In one embodiment, the gastric residence system has a residence time between about 72 hours and about 14 days.

In one embodiment, the gastric residence system has a residence time between about 96 hours and about 14 days. In one embodiment, the gastric residence system has a residence time between about 5 days and about 14 days. In one embodiment, the gastric residence system has a residence time between about 6 days and about 14 days. In one embodiment, the gastric residence system has a residence time between about 7 days and about 14 days. In one embodiment, the gastric residence system has a residence time between about 10 days and about 14 days.

The gastric residence system releases a therapeutically effective amount of agent (or salt thereof) during at least a portion of the residence time or residence period during which the system resides in the stomach. In one embodiment, the system releases a therapeutically effective amount of agent (or salt thereof) during at least about 25% of the residence time. In one embodiment, the system releases a therapeutically effective amount of agent (or salt thereof) during at least about 50% of the residence time. In one embodiment, the system releases a therapeutically effective amount of agent (or salt thereof) during at least about 60% of the residence time. In one embodiment, the system releases a therapeutically effective amount of agent (or salt thereof) during at least about 70% of the residence time. In one embodiment, the system releases a therapeutically effective amount of agent (or salt thereof) during at least about 75% of the residence time. In one embodiment, the system releases a therapeutically effective amount of agent (or salt thereof) during at least about 80% of the residence time. In one embodiment, the system releases a therapeutically effective amount of agent (or salt thereof) during at least about 85% of the residence time. In one embodiment, the system releases a therapeutically effective amount of agent (or salt thereof) during at least about 90% of the residence time. In one embodiment, the system releases a therapeutically effective amount of agent (or salt thereof) during at least about 95% of the residence time. In one embodiment, the system releases a therapeutically effective amount of agent (or salt thereof) during at least about 98% of the residence time. In one embodiment, the system releases a therapeutically effective amount of agent (or salt thereof) during at least about 99% of the residence time.

Evaluation of Release Characteristics

The release characteristics of agent from segments, arms, and gastric residence systems can be evaluated by various assays. Assays for agent release are described in detail in the examples. Release of agent in vitro from segments, arms, and gastric residence systems can be measured by immersing a segment, arm, or gastric residence system in a liquid, such as water, 0.1N HCl, fasted state simulated gastric fluid (FaSSGF), or fed state simulated gastric fluid (FeSSGF). Fasted state simulated gastric fluid (FaSSGF) is preferred for release assays. Simulated gastric fluid indicates either fasted state simulated gastric fluid (FaSSGF) or fed state simulated gastric fluid (FeSSGF); when a limitation is specified as being measured in simulated gastric fluid (SGF), the limitation is met if the limitation holds in either fasted state simulated gastric fluid (FaSSGF) or fed state simulated gastric fluid (FeSSGF). For example, if a segment is indicated as releasing at least 10% of an agent over the first 24 hours in simulated gastric fluid, the limitation is met if the segment releases at least 10% of the agent over the first 24 hours in fasted state simulated gastric fluid, or if the segment releases at least 10% of the agent over the first 24 hours in fed state simulated gastric fluid.

Ethanol burst release is typically measured by immersing a segment, arm, or gastric residence system in a solution of 40% ethanol and 60% fasted state simulated gastric fluid for one hour, followed by immersing the same segment, arm, or gastric residence system in 100% fasted state simulated gastric fluid for the remainder of the test period, and measuring release of agent at appropriate time points. This test is designed to simulate the effects of consumption of alcoholic beverages by a patient having a gastric residence system of the invention deployed in the patient's stomach.

While in vitro tests can be performed using segments, arms, or gastric residence systems, use of segments for in vitro tests is most convenient for rapid evaluation of the release characteristics. When in vitro tests are done to compare release rates under different conditions (such as release in 100% FaSSGF versus release in 40% ethanol/60% FaSSGF), the comparison solutions are kept at the same temperature, such as room temperature, 25° C., or 37° C. Room temperature (ambient temperature) is a preferred temperature for comparisons; in one embodiment, the ambient temperature does not drop below 20° C. or exceed 25° C. (although it may fluctuate between 20° C. and 25° C.).

In vivo tests can be performed in animals such as dogs (for example, beagle dogs or hound dogs) and swine. For in vivo tests, a gastric residence system is used, since an individual segment or arm would not be retained in the stomach of the animal. Blood samples can be obtained at appropriate time points, and, if desired, gastric contents can be sampled by cannula or other technique.

Clinical trials in humans, conducted in accordance with appropriate laws, regulations, and institutional guidelines, also provide in vivo data.

Gastric Delivery Pharmacokinetics for Gastric Residence Systems

The gastric residence systems of the invention provide for high bioavailability of the agent as measured by $AUC_{inf}$ after administration of the systems, relative to the bioavailability of a conventional oral formulation of the agent. The systems also provide for maintenance of an approximately constant plasma level or a substantially constant plasma level of the agent.

Relative bioavailability, FREL, of two different formulations, formulation A and formulation B, is defined as:

$$F_{REL} = 100 \times (AUC_A \times \text{Dose}_B)/(AUC_B \times \text{Dose}_A)$$

where $AUC_A$ is the area under the curve for formulation A, $AUC_B$ is the area under the curve for formulation B, $\text{Dose}_A$ is the dosage of formulation A used, and $\text{Dose}_B$ is the dosage of formulation B used. AUC, the area under the curve for the plot of agent plasma concentration versus time, is usually measured at the same time (t) after administration of each formulation, in order to provide the relative bioavailability of the formulations at the same time point. $AUC_{inf}$ refers to the AUC measured or calculated over "infinite" time, that is, over a period of time starting with initial administration, and ending where the plasma level of the agent has dropped to a negligible amount.

In one embodiment, the substantially constant plasma level of agent provided by the gastric residence systems of the invention can range from at or above the trough level of the plasma level of agent when administered daily in a conventional oral formulation (that is, Cmin of agent administered daily in immediate-release formulation) to at or below the peak plasma level of agent when administered daily in a conventional oral formulation (that is, Cmax of agent administered daily in immediate-release formulation).

In some embodiments, the substantially constant plasma level of agent provided by the gastric residence systems of the invention can be about 50% to about 90% of the peak plasma level of agent when administered daily in a conventional oral formulation (that is, Cmax of agent administered daily in immediate-release formulation). The substantially constant plasma level of agent provided by the gastric residence systems of the invention can be about 75% to about 125% of the average plasma level of agent when administered daily in a conventional oral formulation (that is, Cave of agent administered daily in immediate-release formulation). The substantially constant plasma level of agent provided by the gastric residence systems of the invention can be at or above the trough level of plasma level of agent when administered daily in a conventional oral formulation (that is, Cmin of agent administered daily in immediate-release formulation), such as about 100% to about 150% of Cmin.

The gastric residence systems of the invention can provide bioavailability of agent released from the system of at least about 50%, at least about 60%, at least about 70%, or at least about 80% of that provided by an immediate release form comprising the same amount of agent. As indicated above, the bioavailability is measured by the area under the plasma concentration-time curve (AUCinf).

Dissolution Profile, Bioavailability and Pharmacokinetics for Gastric Residence Systems Dissolution: The gastric residence systems described herein provide a steady release of an agent or a pharmaceutically acceptable salt thereof over an extended period of time. The systems are designed to release a therapeutically effective amount of an agent or salt thereof over the period of residence in the stomach. The release of agent (or salt thereof) can be measured in vitro or in vivo to establish the dissolution profile (elution profile, release rate) of the agent (or salt thereof) from a given residence system in a specific environment. The dissolution profile can be specified as a percentage of the original amount of agent (or salt thereof) present in the system which elutes from the system over a given time period.

Thus, in some embodiments, the agent (or salt thereof) contained in a gastric residence system can have a dissolution profile of 10-20% release between zero hours and 24 hours in a given environment. That is, over the 24-hour period after initial introduction of the gastric residence system into the environment of interest, 10-20% of the initial agent (or salt thereof) contained in the system elutes from the system.

The environment of interest can be 1) the stomach of a patient (that is, an in vivo environment), or 2) simulated gastric fluid (that is, an in vitro environment).

The gastric residence systems of the invention provide for high bioavailability of the agent (or salt thereof) as measured by AUCinf after administration of the systems, relative to the bioavailability of a conventional oral formulation of the agent (or salt thereof). The systems also provide for maintenance of a substantially constant plasma level of the agent (or salt thereof).

Parameters of interest for release include the linearity of release over the residence period of the gastric residence systems, the standard deviation of release over the residence period (which is related to linearity of release; a standard deviation of zero indicates that release is linear over the entire residence period), the release over the initial six hours of residence (that is, burst release upon initial administration), and total release of agent (or salt thereof) over the residence period. A preferable residence period is seven days, although other periods, such as two, three, four, five, six, eight, nine, ten, 11, 12, 13, or 14 days can be useful.

Linearity of agent (or salt thereof) release over the residence period refers to the amount released during each 24-hour period of residence. For a seven-day period of residence, it is desirable that about the amount of agent (or salt thereof) is released each day, i.e., that linearity of agent (or salt thereof) release is maximized. This will minimize the standard deviation of daily agent or agent salt release over the residence period. In some embodiments, the gastric release systems have a variation (or a standard deviation) for daily agent (or salt thereof) release of less than about 100%, less than about 90%, less than about 80%, less than about 70%, less than about 60%, less than about 50%, less than about 40%, less than about 30%, less than about 25%, less than about 20%, less than about 15%, less than about 10%, or less than about 5%, over the period of residence. In some embodiments, the period of residence can be about three days, about seven days, about ten days, or about two weeks.

Minimization of burst release, that is, release over the initial period of residence (such as six hours, twelve hours, or 24 hours after administration of a gastric residence system) is desirable in order to maintain a predictable and steady release profile. If T is the total agent (or salt thereof) release over the residence period (in units of mass), and D is the number of days of the residence period, then completely linear release would mean that about T/D mass of agent (or salt thereof) is released per day. If the period over which burst release is measured is the first six hours, then a linear release profile will result in 0.25×T/D mass of agent (or salt thereof) released during the first six hours. In percentage terms of the total amount of agent (or salt thereof) released over the residence period of D days, linear release would be about 100/D % of agent (or salt thereof) per day, and a linear release over the first six hours would be 25/D %. (Note that 100% in this context indicates the total amount of agent (or salt thereof) released, regardless of how much agent (or salt thereof) is contained in the initial formulation.) Thus, for a seven day residence period, linear release over the first six hours would be about 3.6% of the total amount of agent (or salt thereof) released over the seven-day period.

In some embodiments, during the initial six hours of residence after administration the gastric residence systems release about 0.2 to about 2 times T/D of the total mass of agent (or salt thereof) T released over the residence period of D days, or about 0.2 to about 1.75 times T/D of the total mass of agent (or salt thereof) T released over the residence period of D days, or about 0.2 to about 1.5 times T/D of the total mass of agent (or salt thereof) T released over the residence period of D days, or about 0.2 to about 1.25 times T/D of the total mass of agent (or salt thereof) T released over the residence period of D days, or about 0.2 to about 1 times T/D of the total mass of agent (or salt thereof) T released over the residence period of D days, or about 0.2 to about 0.8 times T/D of the total mass of agent (or salt thereof) T released over the residence period of D days, or about 0.2 to about 0.75 times T/D, or about 0.2 to about 0.7 times T/D, or about 0.2 to about 0.6 times T/D, or about 0.2 to about 0.5 times T/D, or about 0.2 to about 0.4 times T/D, or about 0.2 to about 0.3 times T/D, or about 0.25 to about 2 times T/D, or about 0.3 to about 2 times T/D, or about 0.4 to about 2 times T/D, or about 0.5 to about 2 times T/D, or about 0.6 to about 2 times T/D, or about 0.7 to about 2 times T/D, or about 0.25 to about 1.5 times T/D, or about 0.3 to about 1.5 times T/D, or about 0.4 to about 1.5 times T/D, or about 0.5 to about 1.5 times T/D, or about 0.6 to about 1.5 times T/D, or about 0.7 to about 1.5 times T/D, or about 0.25 to about 1.25 times T/D, or about 0.3 to about 1.25 times T/D, or about 0.4 to about 1.25 times T/D, or about 0.5 to about 1.25 times T/D, or about 0.6 to about 1.25 times T/D, or about 0.7 to about 1.25 times T/D, or about 0.25 to about 1 times T/D, or about 0.3 to about 1 times T/D, or about 0.4 to about 1 times T/D, or about 0.5 to about 1 times T/D, or about 0.6 to about 1 times T/D, or about 0.7 to about 1 times T/D, or about 0.25 times T/D, or about 0.25 to about 0.8 times T/D, or about 0.3 to about 0.8 times T/D, or about 0.4 to about 0.8 times T/D, or about 0.5 to about 0.8 times T/D, or about 0.6 to about 0.8 times T/D, or about 0.7 to about 0.8 times T/D, or about 0.8 times T/D, about 1 times T/D, about 1.25 times T/D, about 1.5 times T/D, or about 2 times T/D.

In some embodiment of the gastric residence systems, during the initial six hours of residence after administration the gastric residence systems release about 2% to about 10% of the total mass of agent (or salt thereof) released over the residence period, or about 3% to about 10%, or about 4% to about 10%, or about 5% to about 10%, or about 6% to about 10%, or about 7% to about 10%, or about 8% to about 10%, or about 9% to about 10%, or about 2% to about 9%, or about 2% to about 8%, or about 2% to about 7%, or about 2% to about 6%, or about 2% to about 5%, or about 2% to about 4%, or about 2% to about 3%.

In some embodiments of the gastric residence systems, where the gastric residence systems have a residence period of about seven days, during the initial six hours of residence after administration the gastric residence systems release about 2% to about 10% of the total mass of agent (or salt thereof) released over the residence period of seven days, or about 3% to about 10%, or about 4% to about 10%, or about 5% to about 10%, or about 6% to about 10%, or about 7% to about 10%, or about 8% to about 10%, or about 9% to about 10%, or about 2% to about 9%, or about 2% to about 8%, or about 2% to about 7%, or about 2% to about 6%, or about 2% to about 5%, or about 2% to about 4%, or about 2% to about 3%.

In some embodiments, during the initial 24 hours of residence after administration, the gastric residence systems release about 10% to about 35% of the total mass of agent (or salt thereof) released over the residence period, or about 10% to about 30%, or about 10% to about 25%, or about 10% to about 20%, or about 10% to about 15%, or about 15% to about 35%, or about 15% to about 35%, or about 15% to about 30%, or about 20% to about 30%, or about 25% to about 35%, or about 25% to about 30%, or about 30% to about 35%.

In some embodiments, where the gastric residence systems have a residence period of about seven days, during the initial 24 hours of residence after administration the gastric residence systems release about 10% to about 35% of the total mass of agent (or salt thereof) released over the residence period of seven days, or about 10% to about 30%, or about 10% to about 25%, or about 10% to about 20%, or about 10% to about 15%, or about 15% to about 35%, or about 15% to about 35%, or about 15% to about 30%, or about 20% to about 30%, or about 25% to about 35%, or about 25% to about 30%, or about 30% to about 35%.

Elastomers

Elastomers (also referred to as elastic polymers or tensile polymers) enable the gastric residence system to be compacted, such as by being folded or compressed, into a form suitable for administration to the stomach by swallowing a container or capsule containing the compacted system. Upon dissolution of the capsule in the stomach, the gastric residence system expands into a shape which prevents passage of the system through the pyloric sphincter of the patient for the desired residence time of the system. Thus, the elastomer must be capable of being stored in a compacted configuration in a capsule for a reasonable shelf life, and of expanding to its original shape, or approximately its original shape, upon release from the capsule. In one embodiment, the elastomer is a silicone elastomer. In one embodiment, the elastomer is formed from a liquid silicone rubber (LSR), such as sold in the Dow Corning QP-1 liquid silicone rubber kit. In one embodiment, the elastomer is crosslinked polycaprolactone. In one embodiment, the elastomer is an enteric polymer, such as those listed in the Enteric Polymer Table. In some embodiments, the coupling polymer(s) used in the system are also elastomers. Elastomers are preferred for use as the central polymer in the star-shaped or stellate design of the gastric residence systems.

In one embodiment, both the coupling polymer and elastomer are enteric polymers, which provides for more complete breakage of the system into the carrier polymer-agent pieces if the system enters the intestine, or if the patient drinks a mildly basic solution in order to induce passage of the system.

Examples of elastomers which can be used include silicones, such as those formed using Dow Corning QP-1 kits; urethane-cross-linked polycaprolactones; poly(acryloyl 6-aminocaproic acid) (PA6ACA); poly(methacrylic acid-co-ethyl acrylate) (EUDRAGIT L 100-55); and mixtures of poly(acryloyl 6-aminocaproic acid) (PA6ACA) and poly (methacrylic acid-co-ethyl acrylate) (EUDRAGIT L 100-55).

Flexible coupling polymers, i.e., elastomeric coupling polymers or elastomers, are used as the central polymer in the star-shaped or stellate design of the gastric residence systems. A particularly preferred elastomer for use as the central elastomer of the stellate or star configuration is silicone rubber. Liquid silicone rubber (LSR) can be molded easily and cured into a desired shape. The Dow Corning QP-1 series, comprising cross-linked dimethyl and methylvinyl siloxane copolymers and reinforcing silica, are examples of such silicone rubber polymers (see, for example, the Web site www.dowcorning.com/DataFiles/090276fe8018ed07.pdf). Non-segmented arms or arms comprising segments of carrier polymer-agent components can then be attached to the central silicone rubber elastomer. Another elastomer which can be used as the central elastomer in the stellate design is crosslinked polycaprolactone.

Specific configurations of gastric residence systems are disclosed in International Patent Application No. WO 2017/100367, and any of those configurations can be used for the gastric residence systems disclosed herein.

Carrier Polymers for Segments and Arms (Carrier Polymer-Agent Component)

The segments and arms of the gastric residence system comprise a carrier polymer-agent component, which comprises the agent (or a pharmaceutically acceptable salt of an agent) to be eluted from the gastric residence system in the gastric environment. The agent is blended into the carrier polymer to form a carrier polymer-agent mixture. This mixture can be formed into the desired shape or shapes for use as carrier polymer-agent components in the systems. After the drug or drug salt is blended into the carrier polymer to form the carrier polymer-drug mixture, the drug or drug salt is distributed or dispersed throughout the blended mixture. If excipients, anti-oxidants, or other ingredients are included in the carrier polymer-drug blend, they will also be distributed or dispersed throughout the blended mixture.

Selection of the carrier material for the agent or pharmaceutically acceptable salt thereof in a gastric residence system influences the release profile of drug during the period of gastric residence. Carrier polymers may be thermoplastic, to allow extrusion using hot melt extrusion or 3D printing techniques. They may also have a high enough melt strength and viscosity to enable extrusion into the required geometry. They may have low melting temperatures (for example, less than about 120° C.), to avoid exposing agents or drugs to high temperatures during manufacture. They may have a sufficient mechanical strength (Young's modulus, compression strength, tensile strength) to avoid breaking in the stomach during the desired residence period. Further, they should be capable of forming stable blends with agents, therapeutic agents, drugs, excipients, dispersants, and other additives.

Exemplary carrier polymers suitable for use in this invention include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly (vinyl pyrrolidone), ethylene/vinyl alcohol copolymer, poly (vinyl alcohol), carboxyvinyl polymer (Carbomer), Carbopol® acidic carboxy polymer, polycarbophil, poly (ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly (ethyleneimine), polyurethane, poly(lactic acid), poly(glycolic acid), poly(lactic-co-glycolic acid) (PLGA), polyhydroxyalkanoates, polyhydroxybutyrate, poly(ethylene-co-vinyl acetate), and copolymers, mixtures, blends and combinations thereof. Polycaprolactone (PCL) and/or thermoplastic polyurethanes are preferred carrier polymers. In some embodiments, polydioxanone is used as the carrier polymer. In any of the embodiments of the gastric residence system, the carrier polymer used in the gastric residence system can comprise polycaprolactone, such as linear polycaprolactone with a number-average molecular weight (Mn) range between about 60 kiloDalton (kDa) to about 100 kDa; 75 kDa to 85 kDa; or about 80 kDa; or between about 45 kDa to about 55 kDa; or between about 50 kDa to about 110,000 kDa, or between about 80 kDa to about 110,000 kDa.

Further, release of drug can be modulated by a wide variety of excipients included in the carrier polymer-agent component. Soluble excipients include P407, Eudragit E, PEG, Polyvinylpyrrolidone (PVP), and Polyvinyl alcohol (PVA). Insoluble, wicking excipients include Eudragit RS and Eudragit RL. Degradable excipients include PLA, PLGA, PLA-PCL, polydioxanone, and linear copolymers of caprolactone and glycolide; polyaxial block copolymers of glycolide, caprolactone, and trimethylene carbonate; polyaxial block copolymers of glycolide, trimethylene carbonate, and lactide; polyaxial block copolymers of glycolide, trimethylene carbonate and polypropylene succinate; polyaxial block copolymers of caprolactone, lactide, glycolide, and trimethylene carbonate; polyaxial block copolymers of glycolide, trimethylene carbonate, and caprolactone; and linear block copolymers of lactide, caprolactone, and trimethylene carbonate; such as linear copolymers of caprolactone (95%) and glycolide (5%); polyaxial block copolymers of glycolide (68%), caprolactone (29%), and trimethylene carbonate (3%); polyaxial block copolymers of glycolide (86%), trimethylene carbonate (9%), and lactide (5%); polyaxial block copolymers of glycolide (70%), trimethylene carbonate (27%) and polypropylene succinate (2%); polyaxial block copolymers of caprolactone (35%), lactide (34%), glycolide (17%), and trimethylene carbonate (14%); polyaxial block copolymers of glycolide (55%), trimethylene carbonate (25%), and caprolactone (20%); and linear block copolymers of lactide (39%), caprolactone (33%), and trimethylene carbonate (28%). Insoluble, swellable excipients include Polyvinyl acetate (PVAc), Crospovidone, Croscarmellose, HPMCAS, and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%). Surfactants include Lecithin, Taurocholate, SDS, Soluplus, Fatty acids, and Kolliphor RH40.

Other excipients can be added to the carrier polymers to modulate the release of agent. Such excipients can be added in amounts from about 1% to 75%, from about 5% to 50%, or from about 5% or about 30%. Examples of such excipients include Poloxamer 407 (available as Kolliphor P407, Sigma Cat #62035), poly(ethylene glycol)-block-poly(propylene glycol)-block-poly(ethylene glycol), CAS No. 9003-11-6; H—(OCH2CH2)x-(O—CH(CH3)CH2)y-(OCH2CH2)z-OH where x and z are about 101 and y is about 56); Pluronic P407; Eudragit E, Eudragit EPO (available from Evonik); hypromellose (available from Sigma, Cat #H3785), Kolliphor RH40 (available from Sigma, Cat #07076), polyvinyl caprolactam, polyvinyl acetate (PVAc), polyvinylpyrrolidone (PVP), polyvinyl alcohol (PVA), polyethylene glycol (PEG), and Soluplus (available from BASF; a copolymer of polyvinyl caprolactam, polyvinyl acetate, and polyethylene glycol). Preferred soluble excipients include Eudragit E, polyethylene glycol (PEG), polyvinylpyrrolidone (PVP), polyvinyl acetate (PVAc), and polyvinyl alcohol (PVA). Preferred insoluble excipients include Eudragit RS and Eudragit RL. Preferred insoluble, swellable excipients include crospovidone, croscarmellose, hypromellose acetate succinate (HPMCAS), and carbopol. EUDRAGIT RS and EUDRAGIT RL are registered trademarks of Evonik (Darmstadt, Germany) for copolymers of ethyl acrylate, methyl methacrylate and methacrylic acid ester with quaternary ammonium groups (trimethylammonioethyl methacrylate chloride), having a molar ratio of ethyl acrylate, methyl methacrylate and trimethylammonioethyl methacrylate of about 1:2:0.2 in Eudragit® RL and about 1:2:0.1 in Eudragit® RS. Preferred insoluble, swellable excipients include crospovidone, croscarmellose, hypromellose acetate succinate (HPMCAS), carbopol, and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%).

Further examples of excipients that can be used in the segments of the gastric residence system are listed in the Excipient Table below.

Excipient Table

| Function | General examples | Specific examples |
| --- | --- | --- |
| Polymeric and non-polymeric solubilizers | Polyalkylene oxides<br>Polyethoxylated castor oil<br>Detergents | Kolliphor RH, Kolliphor P407, Soluplus, Cremophor, SDS |
| Release-enhancing excipient (porogen or wicking agent) | Acrylate polymers<br>Acrylate co-polymers<br>Polyvinylpyrrolidone | Eudragit RL<br>Eudragit RS<br>Eudragit E<br>Linear block copolymer of dioxanone and ethylene glycol (e.g., 80:20 ratio) |
| Dispersant | porous inorganic material<br>polar inorganic material<br>non-toxic metal oxides<br>amphiphilic organic molecules<br>polysaccharides, cellulose, cellulose derivatives<br>fatty acids<br>detergents | silica, hydrophilic-fumed silica, hydrophobic colloidal silica, magnesium aluminum silicate, stearate salts, calcium stearate, magnesium stearate, microcrystalline cellulose, carboxymethylcellulose, hypromellose, phospholipids, polyoxyethylene stearates, zinc acetate, alginic acid, lecithin, sodium lauryl sulfate, aluminum oxide |
| Stabilizer/Preservative agent | Anti-oxidants<br>Anti-microbial agents<br>Buffering substances/ pH stabilizers | Tocopherols<br>Alpha-tocopherol<br>Ascorbic acid; ascorbate salts<br>Carotenes<br>Butylated hydroxytoluene (BHT)<br>Butylated hydroxyanisole (BHA)<br>Fumaric acid<br>calcium carbonate<br>calcium lactate<br>calcium phosphate<br>sodium phosphate<br>sodium bicarbonate |

Carrier Polymer-Agent/Agent Salt Combinations with Excipients and Other Additives The blend of carrier polymer-agent or carrier polymer-agent salt can comprise various excipients and other additives. The following Table CPE-1 lists combinations of excipients and other additives that can be used in combination with agent or salt thereof and carrier polymer in the compositions making up the arms or segments of arms of the gastric residence systems. These excipients and other additives can be combined with agent or salt thereof (where the agent or agent salt comprises between about 10% to about 60% by weight of the composition) with the carrier polymer, such as polycaprolactone, making up the remainder of the composition. Excipients include the following, which can be used individually or in any combination, in amounts ranging from about 1% to about 30%, such as about 5% to about 20%, by weight of the composition: Kolliphor P407 (poloxamer 407, poly(ethylene glycol)-block-poly(propylene glycol)-block-poly(ethylene glycol)), Eudragit RS (Poly[Ethyl acrylate, methyl methacrylate, trimethylammonioethyl methacrylate chloride] 1:2:0.1), Eudragit RL (Poly[Ethyl acrylate, methyl methacrylate, trimethylammonioethyl methacrylate chloride] 1:2:0.2), PDO (polydioxanone), PEG-PCL, SIF (FaSSIF/FaSSGF powder from BioRelevant), EPO (dimethylaminoethyl methacrylate-butyl methacrylate-methyl methacrylate copolymer), Kollidon VA64 (vinylpyrrolidone-vinyl acetate copolymer in a ratio of 6:4 by mass), polyvinyl acetate, polyvinyl pyrrolidine.

Other additives include silicon dioxide (comprising, for example, about 0.1% to about 5% by weight of the composition, such as about 0.1% to 1% or about 0.5%) and an anti-oxidant, such as alpha-tocopherol (comprising, for example, about 0.1% to about 5% by weight of the composition, such as about 0.1% to 1% or about 0.5%). Each row of the table below represents a formulation of excipients and other additives for use with the carrier polymer and agent or salt thereof.

TABLE CPE-1

| Excipients and additives, in combination with agent or salt thereof and carrier polymer |
|---|
| EPO, P407, Silica, α-tocopherol |
| EPO, Silica, α-tocopherol |
| Eudragit RL, Eudragit RS, Kolliphor P407, Silica, α-tocopherol |
| Eudragit RL, Kolliphor P407, Silica, α-tocopherol |
| Eudragit RL, Eudragit RS, Kolliphor P407, Silica, α-tocopherol |
| Eudragit RL, Kolliphor P407, Silica, α-tocopherol |
| Eudragit RL, Kolliphor P407, Silica, α-tocopherol |
| Eudragit RS, P407, Silica, α-tocopherol |
| Eudragit RS, Silica, α-tocopherol |
| Kollidon VA64, Silica, α-tocopherol |
| Kolliphor P407, Silica, α-tocopherol |
| Kolliphor RH40, Silica, α-tocopherol |
| PDO, Silica, α-tocopherol |
| PEG-PCL, Silica, α-tocopherol |

TABLE CPE-1-continued

| Excipients and additives, in combination with agent or salt thereof and carrier polymer |
|---|
| Poly Vinyl Acetate, Silica, α-tocopherol |
| PVP, Silica, α-tocopherol |
| SIF, Silica, α-tocopherol |
| Silica, P188, P407, α-tocopherol |
| Silica, α-tocopherol |

Table CPE-2 lists specific amounts of excipients and other additives that can be used in combination with agent or salt thereof and carrier polymer in the compositions making up the arms or segments of arms of the gastric residence systems.

The amounts listed in Table CPE-2 can be varied by plus-or-minus 20% of each ingredient (for example, 0.5% silica can vary between 0.4% and 0.6% silica, as 20% of 0.5% is 0.1%). Each row of the table below represents a formulation of excipients and other additives for use with the carrier polymer and agent or salt thereof.

TABLE CPE-2

| Excipients and additives, in combination with agent or salt thereof and carrier polymer |
|---|
| 0.5% Silica, 0.5% α-tocopherol |
| 0.5% Silica, 2% P407, 0.5% α-tocopherol |
| 0.5% Silica, 2% P188, 2% P407, 0.5% α-tocopherol |
| 0.5% Silica, 3% Eudragit RS, 2% P407, 0.5% α-tocopherol |
| 1% Kolliphor P407, 0.5% Silica, 0.5% α-tocopherol |
| 10% Eudragit RS, 2.5% P407, 2% Silica, 0.5% α-tocopherol |
| 10% Eudragit RS, 5% P407, 0.5% Silica, 0.5% α-tocopherol |
| 10% Eudragit RS, 5% P407, 2% Silica, 0.5% α-tocopherol |
| 12% Eudragit RL, 3% Kolliphor P407, 0.5% Silica, 0.5% α-tocopherol |
| 12% Eudragit RL, 5% Kolliphor P407, 0.5% Silica, 0.5% α-tocopherol |
| 14.78% Eudragit RS, 0.226% P407, 0.5% Silica, 0.5% α-tocopherol |
| 17.5% Eudragit RS, 5% P407, 0.5% Silica, 0.5% α-tocopherol |
| 19.8% Eudragit RS, 0.5% Silica, 0.5% α-tocopherol |
| 2% Kolliphor P407, 0.5% Silica, 0.5% α-tocopherol |
| 2% P407, 0.5% Silica, 0.5% α-tocopherol |
| 20% Eudragit RS, 2% P407, 0.5% Silica, 0.5% α-tocopherol |
| 21.25% Eudragit RS, 2.5% P407, 0.5% Silica, 0.5% α-tocopherol |
| 25% Eudragit RL, 5% P407, 0.5% Silica, 0.5% α-tocopherol |
| 25% Eudragit RS, 0.5% Silica, 0.5% α-tocopherol |
| 25% Eudragit RS, 5% P407, 0.5% Silica, 0.5% α-tocopherol |
| 3% Eudragit RL, 9% Eudragit RS, 5% Kolliphor P407, 0.5% Silica, 0.5% α-tocopherol |
| 3.5% Eudragit RS, 2.5% P407, 2% Silica, 0.5% α-tocopherol |
| 3.5% Eudragit RS, 5% P407, 2% Silica, 0.5% α-tocopherol |
| 30% PDO, 0.5% Silica, 0.5% α-tocopherol |
| 39.5% PEG-PCL, 0.36% Silica, 0.36% α-tocopherol |
| 4.5% EPO, 4.5% P407, 0.5% Silica, 0.5% α-tocopherol |
| 5% Kolliphor P407, 0.5% Silica, 0.5% α-tocopherol |
| 5% Kolliphor RH40, 0.5% Silica, 0.5% α-tocopherol |
| 5% SIF, 0.5% Silica, 0.5% α-tocopherol |
| 6% Eudragit RL, 5% Kolliphor P407, 0.5% Silica, 0.5% α-tocopherol |
| 6% Eudragit RL, 6% Eudragit RS, 5% Kolliphor P407, 0.5% Silica, 0.5% α-tocopherol |
| 6.75% Eudragit RS, 3.75% P407, 2% Silica, 0.5% α-tocopherol |
| 7% EPO, 2% P407, 0.5% Silica, 0.5% α-tocopherol |
| 9% EPO, 0.5% Silica, 0.5% α-tocopherol |
| 9% Eudragit RL, 3% Eudragit RS, 5% Kolliphor P407, 0.5% Silica, 0.5% α-tocopherol |
| 9% Kollidon VA64, 0.5% Silica, 0.5% α-tocopherol |
| 9% Poly Vinyl Acetate, 0.5% Silica, 0.5% α-tocopherol |
| 9% PVP, 0.5% Silica, 0.5% α-tocopherol |
| 9% SIF, 0.5% Silica, 0.5% α-tocopherol |

Agents for Use in Gastric Residence Systems

Agents (e.g., active pharmaceutical ingredient, therapeutic agent) which can be administered to or via the gastrointestinal tract can be used in the gastric residence systems of the invention. The agent is blended with the carrier polymer, and any other excipients or other additives to the carrier polymer, and formed into a segment for use in a gastric residence system. Agents include, but are not limited to, drugs, pro-drugs, biologics, and any other substance which can be administered to produce a beneficial effect on an illness or injury.

Agents that can be used in the gastric residence systems of the invention include statins, such as rosuvastatin; nonsteroidal anti-inflammatory drugs (NSAIDs) such as meloxicam; selective serotonin reuptake inhibitors (SSRIs) such as escitalopram and citalopram; blood thinners, such as clopidogrel; steroids, such as prednisone; antipsychotics, such as aripiprazole and risperidone; analgesics, such as buprenorphine; opioid antagonists, such as naloxone; anti-asthmatics such as montelukast; anti-dementia drugs, such as memantine; cardiac glycosides such as digoxin; alpha blockers such as tamsulosin; cholesterol absorption inhibitors such as ezetimibe; anti-gout treatments, such as colchicine; antihistamines, such as loratadine and cetirizine, opioids, such as loperamide; proton-pump inhibitors, such as omeprazole; antiviral agents, such as entecavir; antibiotics, such as doxycycline, ciprofloxacin, and azithromycin; antimalarial agents; levothyroxine; substance abuse treatments, such as methadone and varenicline; contraceptives; stimulants, such as caffeine; and nutrients such as folic acid, calcium, iodine, iron, zinc, thiamine, niacin, vitamin C, vitamin D, biotin, plant extracts, phytohormones, and other vitamins or minerals. Biologics that can be used as agents in the gastric residence systems of the invention include proteins, polypeptides, polynucleotides, and hormones. Exemplary classes of agents include, but are not limited to, analgesics; anti-analgesics; anti-inflammatory drugs; antipyretics; antidepressants; antiepileptics; antipsychotic agents; neuroprotective agents; anti-proliferatives, such as anti-cancer agents; antihistamines; antimigraine drugs; hormones; prostaglandins; antimicrobials, such as antibiotics, antifungals, antivirals, and antiparasitics; anti-muscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; and antimalarial drugs, such as quinine, lumefantrine, chloroquine, amodiaquine, pyrimethamine, proguanil, chlorproguanil-dapsone, sulfonamides (such as sulfadoxine and sulfamethoxypyridazine), mefloquine, atovaquone, primaquine, halofantrine, doxycycline, clindamycin, artemisinin, and artemisinin derivatives (such as artemether, dihydroartemisinin, arteether and artesunate). The term "agent" includes salts, solvates, polymorphs, and co-crystals of the aforementioned substances. In some embodiments, the agent is selected from the group consisting of cetirizine, rosuvastatin, escitalopram, citalopram, risperidone, olanzapine, donepezil, and ivermectin. In some embodiments, the agent is one that is used to treat a neuropsychiatric disorder, such as an anti-psychotic agent or an anti-dementia drug such as memantine.

In some embodiments, the agent can exclude adamantane-class drugs. In some embodiments, the agent can exclude any one or more of memantine; amantadine; adapromine; nitromemantine; rimantadine; bromantane; neramexane; or tromantadine; or a pharmaceutically acceptable salt of memantine, amantadine, adapromine, nitromemantine, rimantadine, bromantane, or tromantadine. In some embodiments, the agent can exclude memantine. In some embodiments, the agent can exclude a salt of memantine or a pharmaceutically acceptable salt of memantine.

Agents can be used in the gastric residence systems of the invention in any suitable crystalline form, or in amorphous form, or in both crystalline form or forms and amorphous forms. That is, agent or drug particles contained in the gastric residence systems can be used in crystalline form, in amorphous form, or in a mixture of crystalline forms (either a single crystalline form, or multiple crystalline forms) and amorphous forms, so as to provide a desired rate of release or desired physical or chemical properties.

Gastric residence systems are well-suited for use in treatment of diseases and disorders which present difficulties with patient compliance, and thus in some embodiments, the gastric residence systems are used to treat a disease or disorder where patient compliance with a medication regimen is problematic. Such diseases and disorders include neuropsychiatric diseases and disorders, dementia and other diseases and disorders which affect memory, Alzheimer's disease, psychoses, schizophrenia, and paranoia. Accordingly, agents which can be used in the gastric residence systems include, but are not limited to, anti-dementia agents, anti-Alzheimer's disease agents, and anti-psychotics.

Exemplary hydrophilic agents which can be used in the systems include risperidone, cetirizine, memantine, and olanzapine. Exemplary hydrophobic agents which can be used in the systems include aripiprazole, ivermectin, rosuvastatin, citalopram, and escitalopram.

In some embodiments, the agent or salt thereof (for example, a drug) makes up about 10% to about 40% by weight of the arm or segment, and thus the carrier polymer and any other components of the arm or segment blended into the carrier polymer together make up the remainder of the weight of the arm or segment. In some embodiments, the agent or salt thereof makes up about 10% to about 35%, about 10% to about 30%, about 10% to about 25%, about 10% to about 20%, about 10% to about 15%, about 15% to about 40%, about 20% to about 40%, about 25% to about 40%, about 30% to about 40%, about 35% to about 40%, about 15% to about 35%, about 20% to about 35%, or about 25% to about 40% by weight of the arm or segment.

Further embodiments of arms or segments, where the agent or salt thereof makes up more than about 40% by weight of the arm or segment, are described below under "high agent loading of arms and segments."

High Agent Loading of Arms and Segments

In some embodiments of the invention, the arms, or segments of which the arms are comprised, can have a high loading of agent or pharmaceutically acceptable salt thereof "High loading" generally refers to arms or segments where the agent or salt thereof (for example, a drug) makes up more than about 40% by weight of the arm or segment, and thus the carrier polymer and any other components of the arm or segment blended into the carrier polymer together make up less than about 60% by weight of the arm or segment. Any components of the arms or segments which are not blended into the carrier polymer are not included in the calculation of the weight percentage; for example, if an arm has one or more disintegrating matrices interspersed between segments of the arm, the weight of such matrices would not be included as part of the weight of the arm in the calculation of the weight percentage of agent in the arm. Once the loading of the agent increases to about 60%, it becomes increasingly difficult to properly blend the agent with the carrier polymer, and phase separation of the agent and polymer tends to occur. Thus, the loading of the agent in an arm or segment should not exceed about 60% of the total weight of the arm.

Thus, in some embodiments, the amount of agent by weight in the arms, or segments of which the arms are comprised, can comprise at least about 40%, at least about 45%, at least about 50%, at least about 55%, or about 60%. In some embodiments, the amount of agent by weight in the arms, or segments of which the arms are comprised, can comprise about 40% to about 60%, about 45% to about 60%, about 50% to about 60%, about 55% to about 60%, about 40% to about 55%, about 40% to about 50%, or about 40% to about 45%. In some embodiments, the amount of agent by weight in the arms, or segments of which the arms are comprised, can comprise about 25% to about 60%, about 30% to about 60%, or about 35% to about 60%. In some embodiments, the amount of agent by weight in the arms, or segments of which the arms are comprised, can comprise about 51% to about 60%, about 52% to about 60%, about 53% to about 60%, about 54% to about 60%, about 55% to about 60%, about 56% to about 60%, or about 57% to about 60%. In some embodiments, the agent or pharmaceutically acceptable salt thereof is present in an amount by weight of between about 67% and about 150% of the weight of the carrier polymer.

The combination of the high agent or agent salt loading with the release rate-controlling polymer film provides gastric residence systems with increased amounts of agent or agent salt, while maintaining good release kinetics over the residence period of the system.

Dispersants for Modulation of Agent Release and Stability of Polymer Blend

The use of a dispersant in the carrier polymer-agent component provides numerous advantages. The rate of elution of agent from the carrier polymer-agent component is affected by numerous factors as previously noted, including the composition and properties of the carrier polymer (which may itself comprise multiple polymeric and non-polymeric components); the physical and chemical properties of the agent; and the gastric environment. Avoiding burst release of agent, especially hydrophilic agents, and maintaining sustained release of the agent over the effective release period or residence period is an important characteristic of the systems. The use of a dispersant according to the invention enables better control of release rate and suppression of burst release. Burst release and release rate can be tuned by using varied concentrations of dispersant. For example, different dispersants and different excipients, at varying concentrations, can tune burst release of cetirizine in simulated gastric fluid.

Dispersants which can be used in the invention include: silicon dioxide (silica, $SiO_2$) (hydrophilic fumed); stearate salts, such as calcium stearate and magnesium stearate; microcrystalline cellulose; carboxymethylcellulose; hydrophobic colloidal silica; hypromellose; magnesium aluminum silicate; phospholipids; polyoxyethylene stearates; zinc acetate; alginic acid; lecithin; fatty acids; sodium lauryl sulfate; and non-toxic metal oxides such as aluminum oxide. Porous inorganic materials and polar inorganic materials can be used. Hydrophilic-fumed silicon dioxide is a preferred dispersant. One particularly useful silicon dioxide is sold by Cabot Corporation (Boston, Massachusetts, USA) under the registered trademark CAB-O-SIL® M-5P (CAS #112945-52-5), which is hydrophilic-fumed silicon dioxide having a BET surface area of about 200 m2/g±15 m2/g The mesh residue for this product on a 45 micron sieve is less than about 0.02%. The typical primary aggregate size is about 150 to about 300 nm, while individual particle sizes may range from about 5 nm to about 50 nm.

In addition to anti-aggregation/anti-flocculation activity, the dispersant can help prevent phase separation during fabrication and/or storage of the systems. This is particularly useful for manufacture of the systems by hot melt extrusion.

The weight/weight ratio of dispersant to agent substance can be about 0.1% to about 5%, about 0.1% to about 4%, about 0.1% to about 3%, about 0.1% to about 2%, about 0.1% to about 1%, about 1% to about 5%, about 1% to about 4%, about 1% to about 3%, about 1% to about 2%, about 2% to about 4%, about 2% to about 3%, about 3% to about 4%, about 4% to about 5%, or about 0.1%, about 0.5%, about 1%, about 2%, about 3%, about 4% or about 5%.

Dispersants can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

Dispersants can also be used to modulate the amount of burst release of agent or pharmaceutically acceptable salt thereof during the initial period when the gastric residence system is administered. In embodiments of a gastric residence system that is to be administered once weekly, the burst release over the approximately first six hours after initial administration is less than about 8%, preferably less than about 6%, of the total amount of agent (or salt thereof) in the system. In embodiments of a gastric residence system that is to be administered once every three days, the burst release over the approximately first six hours after initial administration is less than about 12%, preferably less than about 10%, of the total amount of agent (or salt thereof) in the system. In embodiments of a gastric residence system that is to be administered once daily, the burst release over the approximately first six hours after initial administration is less than about 40%, preferably less than about 30%, of the total amount of agent (or salt thereof) in the system. In general, if a new gastric residence system is administered every D days, and the total mass of agent (or salt thereof) is M, then the gastric residence system releases less than about [(M divided by D) times 0.5], preferably less than about [(M divided by D) multiplied by 0.4], or less than about [(M divided by D) multiplied by ⅜], more preferably less than about [(M divided by D) multiplied by 0.3], over the approximately first six hours after initial administration. In further embodiments, the gastric residence system releases at least about [(M divided by D) multiplied by 0.25] over the approximately first six hours after initial administration, that is, the system releases at least about one-quarter of the daily dosage over the first one-quarter of the first day of administration.

Stabilizers for Use in Gastric Residence Systems

Many agents are prone to oxidative degradation when exposed to reactive oxygen species, which can be present in the stomach. An agent contained in the system may thus oxidize due to the prolonged residence in the stomach of the system, and the extended release period of agent from the system. Accordingly, it is desirable to include stabilizers or preservatives in the systems, in order to stabilize the agent to prevent oxidative and other degradation.

Stabilizers, such as anti-oxidants including tocopherols, alpha-tocopherol, ascorbic acid, ascorbyl palmitate, butylated hydroxytoluene, butylated hydroxyanisole, and fumaric acid, can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

Anti-oxidant stabilizers that can be included in the systems to reduce or prevent oxidation of the agent include alpha-tocopherol (about 0.01 to about 0.05% v/v), ascorbic acid (about 0.01 to about 0.1% w/v), ascorbyl palmitate (about 0.01 to about 0.1% w/v), butylated hydroxytoluene (about 0.01 to about 0.1% w/w), butylated hydroxyanisole (about 0.01 to about 0.1% w/w), and fumaric acid (up to 3600 ppm). Vitamin E, a tocopherol, a Vitamin E ester, a tocopherol ester, ascorbic acid, or a carotene, such as alpha-tocopherol, Vitamin E succinate, alpha-tocopherol succinate, Vitamin E acetate, alpha-tocopherol acetate, Vitamin E nicotinate, alpha-tocopherol nicotinate, Vitamin E linoleate, or alpha-tocopherol linoleate can be used as anti-oxidant stabilizers.

Certain agents can be pH-sensitive, especially at the low pH present in the gastric environment. Buffering or pH-stabilizer compounds that can be included in the systems to reduce or prevent degradation of agent at low pH include calcium carbonate, calcium lactate, calcium phosphate, sodium phosphate, and sodium bicarbonate. They are typically used in an amount of up to about 2% w/w. The buffering or pH-stabilizer compounds can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

The anti-oxidant stabilizers, pH stabilizers, and other stabilizer compounds are blended into the polymers containing the agent (or pharmaceutically acceptable salt thereof) by blending the stabilizer(s) into the molten carrier polymer-agent or agent salt mixture. The stabilizer(s) can be blended into molten carrier polymer prior to blending the agent (or salt thereof) into the polymer-stabilizer mixture; or the stabilizer(s) can be blended with agent (or salt thereof) prior to formulation of the blended agent (or salt thereof)-stabilizer mixture in the carrier polymer; or stabilizer(s), agent (or salt thereof), and molten carrier polymer can be blended simultaneously. Agent (or salt thereof) can also be blended with molten carrier polymer prior to blending the stabilizer(s) into the polymer-agent or agent salt mixture.

In one embodiment, less than about 10% of the agent (or salt thereof) remaining in the system is degraded or oxidized after a gastric residence period of about 24 hours. In one embodiment, less than about 10% of the agent (or salt thereof) remaining in the system is degraded or oxidized after a gastric residence period of about 48 hours. In one embodiment, less than about 10% of the agent (or salt thereof) remaining in the system is degraded or oxidized after a gastric residence period of about 72 hours. In one embodiment, less than about 10% of the agent (or salt thereof) remaining in the system is degraded or oxidized after a gastric residence period of about 96 hours. In one embodiment, less than about 10% of the agent (or salt thereof) remaining in the system is degraded or oxidized after a gastric residence period of about five days. In some embodiments, less than about 10% of the agent (or salt thereof) remaining in the system is degraded or oxidized after a gastric residence period of about a week. In some embodiments, less than about 10% of the agent (or salt thereof) remaining in the system is degraded or oxidized after a gastric residence period of about two weeks.

In one embodiment, less than about 5% of the agent (or salt thereof) remaining in the system is degraded or oxidized after a gastric residence period of about 24 hours. In one embodiment, less than about 5% of the agent (or salt thereof) remaining in the system is degraded or oxidized after a gastric residence period of about 48 hours. In one embodiment, less than about 5% of the agent (or salt thereof) remaining in the system is degraded or oxidized after a gastric residence period of about 72 hours. In one embodiment, less than about 5% of the agent (or salt thereof) remaining in the system is degraded or oxidized after a gastric residence period of about 96 hours. In one embodiment, less than about 5% of the agent (or salt thereof) remaining in the system is degraded or oxidized after a gastric residence period of about five days. In some embodiments, less than about 5% of the agent (or salt thereof) remaining in the system is degraded or oxidized after a gastric residence period of about a week. In some embodiments, less than about 5% of the agent (or salt thereof) remaining in the system is degraded or oxidized after a gastric residence period of about two weeks.

Coupling Polymers

The coupling polymer is used to link one or more carrier polymer-agent components (i.e., arm or segment of an arm) to one or more carrier polymer-agent components, to link one or more carrier polymer-agent components to one or more elastomer components (i.e., core), or to link one or more elastomer components to one or more elastomer components. Thus, the coupling polymers form linker regions between other components of the system. Enteric polymers and time-dependent polymers are preferred for use as coupling polymers. In some embodiments, enteric polymers are used as coupling polymers. In some embodiments, time-dependent polymers which are pH-resistant, that is, less sensitive to changes in pH than enteric polymers, are used as coupling polymers. In some embodiments, both enteric polymers and time-dependent polymers which are less sensitive to changes in pH than enteric polymers are used as coupling polymers.

Enteric polymers are relatively insoluble under acidic conditions, such as the conditions encountered in the stomach, but are soluble under the less acidic to basic conditions encountered in the small intestine. Enteric polymers which dissolve at about pH 5 or above can be used as coupling polymers, as the pH of the initial segment of the small intestine, the duodenum, ranges from about 5.4 to 6.1. If the gastric residence system passes intact through the pyloric valve, the enteric coupling polymer will dissolve and the components linked by the coupling polymer will break apart, allowing passage of the residence system through the small and large intestines. Thus, the gastric residence systems are designed to uncouple rapidly in the intestinal environment by dissolution of the coupling polymer.

By "time-dependent polymer which are pH-resistant" (or equivalently, "pH-resistant time-dependent polymers") is meant that, under conditions where an enteric polymer would degrade to the point that it would no longer link the components together, the time-dependent polymer will still have sufficient mechanical strength to link the components together. In some embodiments, the time-dependent polymer retains about the same linking capacity, that is, about 100% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 90% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 75% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 60% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 50% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 25% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer resists breaking under a flexural force of about 0.2 Newtons (N), about 0.3 N, about 0.4 N, about 0.5 N, about 0.75 N, about 1 N, about 1.5 N, about 2 N, about 2.5 N, about 3 N, about 4 N, or about 5 N, after exposure to a solution between about pH 7 to about pH 8, where the exposure is for about an hour, about a day, about three days, or about a week. Linkage strength can be measured by any relevant test that serves to test coupling ability, such as a four-point bending flexural test (ASTM D790).

Exemplary coupling polymers include, but are not limited to, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylate-methacrylic acid-octyl acrylate copolymer, and copolymers, mixtures, blends and combinations thereof. Some of the enteric polymers that can be used in the invention are listed in the Enteric Polymer Table, along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Poly(methacrylic acid-co-ethyl acrylate) (sold under the trade name EUDRAGIT L 100-55; EUDRAGIT is a registered trademark of Evonik Rohm GmbH, Darmstadt, Germany) is a preferred enteric polymer. Another preferred enteric polymer is hydroxypropylmethylcellulose acetate succinate (hypromellose acetate succinate or HPMCAS; Ashland, Inc., Covington, Kentucky, USA), which has a tunable pH cutoff from about 5.5 to about 7.0. Cellulose acetate phthalate, cellulose acetate succinate, and hydroxypropyl methylcellulose phthalate are also suitable enteric polymers.

In one embodiment, the enteric polymers used in the gastric residence system dissolve at a pH above about 4. In some embodiments, the enteric polymers used in the gastric residence system dissolve at a pH above about 5. In some embodiments, the enteric polymers used in the gastric residence system dissolve at a pH above about 6. In some embodiments, the enteric polymers used in the gastric residence system dissolve at a pH above about 7. In some embodiments, the enteric polymers used in the gastric residence system dissolve at a pH above about 7.5. In some embodiments, the enteric polymers used in the gastric residence system dissolve at a pH between about 4 and about 5. In some embodiments, the enteric polymers used in the gastric residence system dissolve at a pH between about 4 and about 6. In some embodiments, the enteric polymers used in the gastric residence system dissolve at a pH between about 4 and about 7. In some embodiments, the enteric polymers used in the gastric residence system dissolve at a pH between about 4 and about 7.5. In some embodiments, the enteric polymers used in the gastric residence system dissolve at a pH between about 5 and about 6. In some embodiments, the enteric polymers used in the gastric residence system dissolve at a pH between about 5 and about 7. In some embodiments, the enteric polymers used in the gastric residence system dissolve at a pH between about 5 and about 7.5. In some embodiments, the enteric polymers used in the gastric residence system dissolve at a pH between about 6 and about 7. In some embodiments, the enteric polymers used in the gastric residence system dissolve at a pH between about 6 and about 7.5.

Enteric Polymer Table

| Polymer | Dissolution pH |
|---|---|
| Cellulose acetate phthalate | 6.0-6.4 |
| Hydroxypropyl methylcellulose phthalate 50 | 4.8 |
| Hydroxypropyl methylcellulose phthalate 55 | 5.2 |
| Polyvinylacetate phthalate | 5.0 |
| Methacrylic acid-methyl methacrylate copolymer (1:1) | 6.0 |
| Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate | 7.0 |
| Poly (methyl vinyl ether/maleic acid) monoethyl ester | 4.5-5.0 |
| Poly (methyl vinyl ether/maleic acid) n-butyl ester | 5.4 |

Additional preferred polymers for use as coupling polymers are time-dependent polymers, that is, polymers that degrade in a time-dependent manner in the gastric environment. For example, the liquid plasticizer triacetin releases from a polymer formulation in a time-dependent manner over seven days in simulated gastric fluid, while Plastoid B retains its strength over a seven-day period in simulated gastric fluid. Thus, a polymer that degrades in a time-dependent manner can be readily prepared by mixing Plastoid B and triacetin; the degradation time of the Plastoid B-triacetin mixture can be extended by increasing the amount of Plastoid B used in the mixture (that is, using less triacetin in the mixture), while the degradation time can be decreased by decreasing the amount of Plastoid B used in the mixture (that is, using more triacetin in the mixture).

A variety of time-dependent mechanisms are available. Water-soluble time-dependent polymers break down as water penetrates through the polymer. Examples of such polymers are hydroxypropyl methylcellulose and poly vinyl acetate. Acid soluble time-dependent polymers break down over time in an acidic environment. Examples include Eudragit EPO. Time-dependent polymers can use water soluble plasticizers; as plasticizer is released, the remaining polymer becomes brittle and breaks under gastric forces. Examples of such polymers include triacetin and triethyl citrate.

In some embodiments, the carrier polymer-agent components are arms comprised of segments attached by enteric polymers. In some embodiments, the carrier polymer-agent components are attached to the elastomer component of the system by enteric polymers. In any of these embodiments, when enteric polymers are used for both segment-to-segment attachments and for attachment of the arms to the elastomeric component, the enteric polymer used for segment-segment attachments can be the same enteric polymer as the enteric polymer used for attachment of the arms to the elastomeric component, or the enteric polymer used for segment-segment attachments can be a different enteric polymer than the enteric polymer used for attachment of the arms to the elastomeric component. The enteric polymers used for the segment-segment attachments can all be the same enteric polymer, or can all be different enteric polymers, or some enteric polymers in the segment-segment attachments can be the same and some enteric polymers in the segment-segment attachments can be different. That is, the enteric polymer(s) used for each segment-segment attachment and the enteric polymer used for attachment of the arms to the elastomeric component can be independently chosen.

In some embodiments, the carrier polymer-drug components are non-segmented arms attached to the elastomer component of the system by enteric polymers, time-dependent linkers, or disintegrating matrices, or by any combination of enteric polymers, time-dependent linkers, and/or disintegrating matrices.

In any of the embodiments of the gastric residence systems described herein, the coupling polymers or linkers can comprise hydroxypropyl methyl cellulose acetate succinate (HPMCAS) and polycaprolactone (PCL). These blends can be used to form disintegrating linkers or disintegrating matrices. The ratio of HPMCAS to polycaprolactone in the disintegrating linker or disintegrating matrix can be between about 80% HPMCAS:20% PCL to about 20% HPMCAS:80% PCL. the ratio of HPMCAS to polycaprolactone can be between about 80% HPMCAS:20% PCL to about 20% HPMCAS:80% PCL; between about 70% HPMCAS:30% PCL to about 30% HPMCAS:70% PCL; between about 60% HPMCAS:40% PCL to about 40% HPMCAS:60% PCL; between about 80% HPMCAS:20% PCL to about 50% HPMCAS:50% PCL; between about 80% HPMCAS:20% PCL to about 60% HPMCAS:40% PCL; between about 70% HPMCAS:30% PCL to about 50% HPMCAS:50% PCL; between about 70% HPMCAS:30% PCL to about 60% HPMCAS:40% PCL; between about 20% HPMCAS:80% PCL to about 40% HPMCAS:60% PCL; between about 20% HPMCAS:80% PCL to about 50% HPMCAS:50% PCL; between about 30% HPMCAS:70% PCL to about 40% HPMCAS:60% PCL; between about 30% HPMCAS:70% PCL to about 50% HPMCAS:50% PCL; or about 80% HPMCAS:20% PCL, about 70% HPMCAS:30% PCL, about 60% HPMCAS:40% PCL, about 50% HPMCAS:50% PCL, about 40% HPMCAS:60% PCL, about 30% HPMCAS:70% PCL, or about 20% HPMCAS:80% PCL. The linker can further comprise a plasticizer selected from the group consisting of triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, and diacetylated monoglycerides.

The linkers are chosen to weaken sufficiently after a specified period of time in order to allow the gastric residence systems to reach a point where they de-couple and pass through the pylorus and out of the stomach after the desired residence period or weaken sufficiently such that the gastric residence system is no longer retained in the stomach; that is, the linkers weaken to the point of uncoupling (the uncoupling point) or to the point where the gastric residence system can pass through the pylorus (the pyloric passage point, or passage point). Thus, in one embodiment, linkers are used that uncouple after about two days in a human stomach; after about three days in a human stomach; after about four days in a human stomach; after about five days in a human stomach; after about six days in a human stomach; after about seven days in a human stomach; after about eight days in a human stomach; after about nine days in a human stomach; after about ten days in a human stomach; or after about two weeks in a human stomach. In one embodiment, linkers are used that uncouple after about two days in a dog stomach; after about three days in a dog stomach; after about four days in a dog stomach; after about five days in a dog stomach; after about six days in a dog stomach; after about seven days in a dog stomach; after about eight days in a dog stomach; after about nine days in a dog stomach; after about ten days in a dog stomach; or after about two weeks in a dog stomach. In one embodiment, linkers are used that uncouple after about two days in a pig stomach; after about three days in a pig stomach; after about four days in a pig stomach; after about five days in a pig stomach; after about six days in a pig stomach; after about seven days in a pig stomach; after about eight days in a pig stomach; after about nine days in a pig stomach; after about ten days in a pig stomach; or after about two weeks in a pig stomach. In one embodiment, linkers are used that uncouple after about two days in fasted-state simulated gastric fluid; after about three days in fasted-state simulated gastric fluid; after about four days in fasted-state simulated gastric fluid; after about five days in fasted-state simulated gastric fluid; after about six days in fasted-state simulated gastric fluid; after about seven days in fasted-state simulated gastric fluid; after about eight days in fasted-state simulated gastric fluid; after about nine days in fasted-state simulated gastric fluid; after about ten days in fasted-state simulated gastric fluid; or after about two weeks in fasted-state simulated gastric fluid. In one embodiment, linkers are used that uncouple after about two days in fed-state simulated gastric fluid; after about three days in fed-state simulated gastric fluid; after about four days in fed-state simulated gastric fluid; after about five days in fed-state simulated gastric fluid; after about six days in fed-state simulated gastric fluid; after about seven days in fed-state simulated gastric fluid; after about eight days in fed-state simulated gastric fluid; after about nine days in fed-state simulated gastric fluid; after about ten days in fed-state simulated gastric fluid; or after about two weeks in fed-state simulated gastric fluid. In one embodiment, linkers are used that uncouple after about two days in water at pH 2; after about three days in water at pH 2; after about four days in water at pH 2; after about five days in water at pH 2; after about six days in water at pH 2; after about seven days in water at pH 2; after about eight days in water at pH 2; after about nine days in water at pH 2; after about ten days in water at pH 2; or after about two weeks in water at pH 2. In one embodiment, linkers are used that uncouple after about two days in water at pH 1; after about three days in water at pH 1; after about four days in water at pH 1; after about five days in water at pH 1; after about six days in water at pH 1; after about seven days in water at pH 1; after about eight days in water at pH 1; after about nine days in water at pH 1; after about ten days in water at pH 1; or after about two weeks in water at pH 1.

The de-coupling or pyloric passage point in human, dog, or pig occurs when the system passes out of the stomach, that is, when it passes through the pylorus. For the in vitro measurements in simulated gastric fluid or acidic water, the de-coupling or pyloric passage point occurs when the linker weakens to the point where it will break under the normal compressive forces of the stomach, typically about 0.1 Newton to 0.2 Newton. Linkage strength (breaking point) can be measured by any relevant test that serves to test coupling ability, that is, the force required to break the linker, such as the four-point bending flexural test (ASTM D790) described in Example 18 of WO 2017/070612, or Examples 12, 13, 15, 17, or 18 of WO 2017/100367. In one embodiment, the de-coupling or pyloric passage point is reached when the linkers uncouple at about 0.2 N of force. In another embodiment, the de-coupling or pyloric passage point is reached when the linkers uncouple at about 0.1 N of force.

The gastric residence systems can reach the pyloric passage point without any or all of the linkers actually breaking. If the linkers weaken or degrade to the point where they can no longer hold the gastric residence system in the stomach, even if one, some, or all of the linkers do not break, the gastric residence system will pass through the pylorus and into the small intestine (the pyloric passage point or passage point). In some embodiments, linkers are used that weaken to the passage point after about two days in a human stomach; after about three days in a human stomach; after about four days in a human stomach; after about five days in a human stomach; after about six days in a human stomach; after about seven days in a human stomach; after about eight days in a human stomach; after about nine days in a human stomach; after about ten days in a human stomach; or after about two weeks in a human stomach. In some embodiments, linkers are used that weaken to the passage point after about two days in a dog stomach; after about three days in a dog stomach; after about four days in a dog stomach; after about five days in a dog stomach; after about six days in a dog stomach; after about seven days in a dog stomach; after about eight days in a dog stomach; after about nine days in a dog stomach; after about ten days in a dog stomach; or after about two weeks in a dog stomach. In some embodiments, linkers are used that weaken to the passage point after about two days in a pig stomach; after about three days in a pig stomach; after about four days in a pig stomach; after about five days in a pig stomach; after about six days in a pig stomach; after about seven days in a pig stomach; after about eight days in a pig stomach; after about nine days in a pig stomach; after about ten days in a pig stomach; or after about two weeks in a pig stomach. In some embodiments, linkers are used that weaken to the passage point after about two days in fasted-state simulated gastric fluid; after about three days in fasted-state simulated gastric fluid; after about four days in fasted-state simulated gastric fluid; after about five days in fasted-state simulated gastric fluid; after about six days in fasted-state simulated gastric fluid; after about seven days in fasted-state simulated gastric fluid; after about eight days in fasted-state simulated gastric fluid; after about nine days in fasted-state simulated gastric fluid; after about ten days in fasted-state simulated gastric fluid; or after about two weeks in fasted-state simulated gastric fluid. In some embodiments, linkers are used that weaken to the passage point after about two days in fed-state simulated gastric fluid; after about three days in fed-state simulated gastric fluid; after about four days in fed-state simulated gastric fluid; after about five days in fed-state simulated gastric fluid; after about six days in fed-state simulated gastric fluid; after about seven days in fed-state simulated gastric fluid; after about eight days in fed-state simulated gastric fluid; after about nine days in fed-state simulated gastric fluid; after about ten days in fed-state simulated gastric fluid; or after about two weeks in fed-state simulated gastric fluid. In some embodiments, linkers are used that weaken to the passage point after about two days in water at pH 2; after about three days in water at pH 2; after about four days in water at pH 2; after about five days in water at pH 2; after about six days in water at pH 2; after about seven days in water at pH 2; after about eight days in water at pH 2; after about nine days in water at pH 2; after about ten days in water at pH 2; or after about two weeks in water at pH 2. In some embodiments, linkers are used that weaken to the passage point after about two days in water at pH 1; after about three days in water at pH 1; after about four days in water at pH 1; after about five days in water at pH 1; after about six days in water at pH 1; after about seven days in water at pH 1; after about eight days in water at pH 1; after about nine days in water at pH 1; after about ten days in water at pH 1; or after about two weeks in water at pH 1.

Filaments for Improved Gastric Residence

Following is a description of gastric residence systems having a filament. As described in detail below, the filament of gastric residence systems having a filament may help prevent the gastric residence system from prematurely passing through a patient's pylorus. Accordingly, a filament and gastric residence systems having a filament described herein can help improve the efficacy and reliability of gastric residence systems.

Gastric residence systems with a filament can prevent the gastric residence system from prematurely passing through a patient's pylorus. Described herein are gastric residence systems having comprising a filament to help minimize the risk of the gastric residence system passing through the pylorus of a patient prematurely.

Figure 4A:
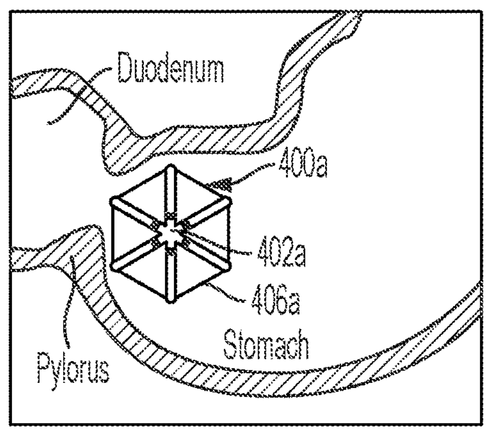
FIGS. 4A and 4B show a gastric residence system having filament and how the filament may help prevent premature passage through the pylorus, according to some embodiments.
Figure 4B:
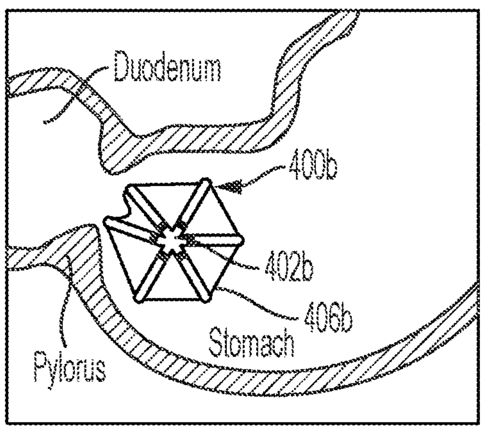

A filament may be attached to the distal ends of the arms of a gastric residence system. FIGS. 4A and 4B show how the inclusion of a filament affects the most common bending and passage modes of an intact gastric residence system through the pylorus. In particular, the filament can prevent one or two arms from prematurely entering the pylorus, for example. It also maintains the spacing of the arms, which changes the bending geometry and increases the force required to compress the gastric residence system to a configuration small enough to prematurely pass through the pylorus.

For example, gastric residence system 400*a* of FIG. 4A comprises a central core 402*a* and a plurality of arms. As shown, each arm 404*a* of the plurality of arms extends radially from the central core 402. Each arm 404 is attached to core 402*a* at a proximal end. Filament 406*a* is shown attached to the distal end of each arm 404*a*. FIG. 4A shows gastric residence system 400*a* in an open configuration. As shown, when gastric residence system 400*a* remains in an open configuration, filament 406*a* helps prevent gastric residence system 400*a* from passing prematurely through a pylorus.

FIG. 4B shows gastric residence system 400*b* in a bended configuration. Gastric residence system 400*b* comprises core 402*b*, arms 404*b*, and filament 406*b*. As shown, even if gastric residence system 400*b* bends into a configuration that might otherwise allow for premature passage through a patient's pylorus (see FIG. 3B), filament 408*b* can help prevent the device from passing. In particular, filament 408*b* is flexible and stretchable such that it can maintain its integrity despite gastric forces that may bend and contort gastric residence system 400*b*.

In some embodiments, a gastric residence system may comprise tips located at a distal end of one or more arms. The tips may comprise an enteric polymer composition. The filament may be connected to each arm by way of the tip at the distal end. The tips may be configured to separate from the rest of the arm when in a gastric environment. In particular, the tips may be configured to separate from the arms, allowing the filament to also separate from the gastric residence system. This separation may be fine-tuned such that the tips and filament separate once a predetermined gastric residence time approaches expiration, such that the gastric residence system separates and passes through a patient's pylorus at the expiration of the predetermined gastric residence time. If the tips and/or filament separate too early, the gastric residence system risks passing through the patient's pylorus prematurely.

In some embodiments, the arm tips may comprise one or more polymers, an enteric material, a plasticizer, and an acid. Suitable polymers may include polycaprolactone and/or thermoplastic polyurethanes (e.g. Pathway™ by Lubrizol). In some embodiments, the composition of an arm tip may be the same as the composition of a linker component. In some embodiments, the composition of an arm tip may be different than the composition of a linker component. In some embodiments, an arm tip may comprise from 10 to 50 wt. % polymer. In some embodiments, an arm tip may comprise less than 50 wt. %, less than 40 wt. %, less than 30 wt. %, or less than 20 wt. % polymer. In some embodiments, an arm tip may comprise more than 10 wt. %, more than 20 wt. %, more than 30 wt. %, or more than 40 wt. % polymer.

In some embodiments, the enteric material of the arm tips may comprise an enteric polymer. For example, suitable enteric polymers include Cellulose acetate phthalate, Hydroxypropyl methylcellulose phthalate 50, Hydroxypropyl methylcellulose phthalate 55, Polyvinylacetate phthalate, Methacrylic acid-methyl methacrylate copolymer (1:1), Methacrylic acid-methyl methacrylate copolymer (2:1), Methacrylic acid-ethyl acrylate copolymer (2:1), Shellac, Hydroxypropyl methylcellulose acetate succinate, Poly (methyl vinyl ether/maleic acid) monoethyl ester, or Poly (methyl vinyl ether/maleic acid) n-butyl ester. In some embodiments, an arm tip may comprise from 20 to 90 wt. % enteric material. In some embodiments, an arm tip may comprise less than 90 wt. %, less than 80 wt. %, less than 70 wt. %, less than 60 wt. %, less than 50 wt. %, less than 40 wt. %, or less than 30 wt. % enteric material. In some embodiments, an arm tip may comprise more than 20 wt. %, more than 30 wt. %, more than 40 wt. %, more than 50 wt. %, more than 60 wt. %, more than 70 wt. %, or more than 90 wt. % enteric material.

Suitable plasticizers may include propylene glycol, P407, triethyl citrate, triacetin, dibutyl sebacate, and/or polyethylene glycol. In some embodiments, an arm tip may comprise from 1 to 20 wt. % plasticizer. In some embodiments, an arm tip may comprise less than 20 wt. %, less than 15 wt. %, less than 10 wt. %, or less than 5 wt. % plasticizer. In some embodiments, an arm tip may comprise more than 1 wt. %, more than 5 wt. %, more than 10 wt. %, or more than 15 wt. % plasticizer.

Suitable acids can include stearic acid or other fatty acids. In some embodiments, an arm tip may comprise from 1 to 20 wt. % or from 1 to 10 wt. % acid. In some embodiments, an arm tip may comprise less than 20 wt. %, less than 15 wt. %, less than 10 wt. %, or less than 5 wt. % acid. In some embodiments, an arm tip may comprise more than 1 wt. %, more than 5 wt. %, more than 10 wt. %, or more than 15 wt. % acid.

Figure 5A:
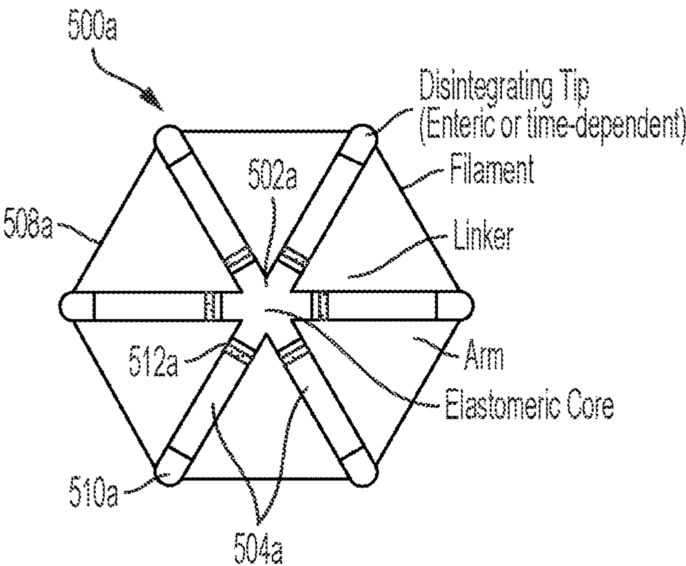
FIGS. 5A and 5B show two different configurations of gastric residence systems comprising a filament, according to some embodiments.
Figure 5B:
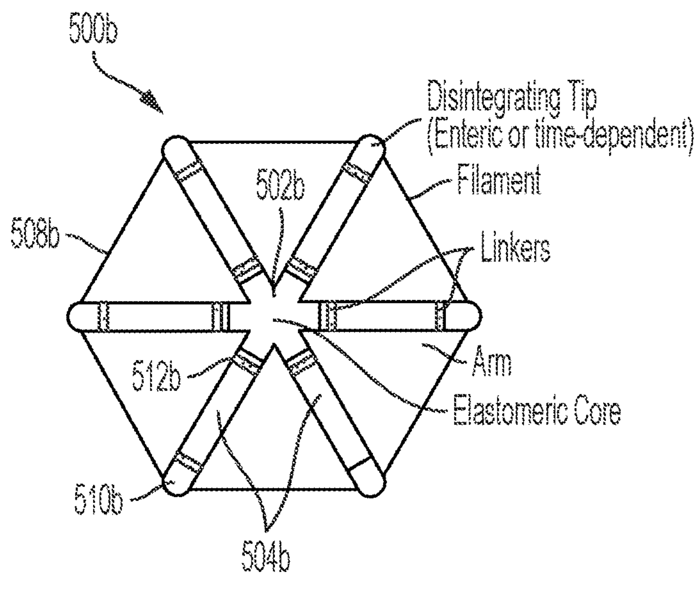

FIGS. 5A and 5B show two different configurations of a gastric residence system having a filament connected to tips at a distal end of each arm. In particular, FIG. 5A shows gastric residence system 500*a* comprising core 502*a* and six arms 504*a*. Each arm 504*a* comprises a tip 510*a* at a distal end. In some embodiments, each arm 504*a* may be connected to core 502*a* via a linker 512*a*. As shown, filament 508*a* connects each arm 504*a* at tip 510*a*. In some embodiments, a single filament 508*a* may wrap circumferentially around gastric residence system 500*a*, connecting to each arm at tip 510*a*. In some embodiments, multiple filaments 508*a* may connect each arm 504*a* of gastric residence system 500*a*.

FIG. 5B shows gastric residence system 500*b* having core 502*b*, six arms 504*b*, a tip 510*b* at a distal end of each arm 504*b*. Unlike gastric residence system 500*a* of FIG. 5A, gastric residence system 500*b* comprises a linker 512*b* connecting arm 504*b* to core 502*b*, as well as a linker 512*b* connecting two segments of arm 504*b*. As shown, filament 508*b* connects each arm 504*b* at tip 510*b*. In some embodiments, a single filament 508*b* may wrap circumferentially around gastric residence system 500*a*, connecting to each arm at tip 510*a*. In some embodiments, multiple filaments 508*b* may connect each arm 504*b* of gastric residence system 500*b*.

Filaments for improved gastric residence may include elastic polymers and/or bioresorbable polymers.

Suitable elastic polymers may include Polyurethanes (Lubrizol Pellethane, Pathways, Tecoflex, carbothane), polyamide-polyether block copolymers (Pebax), poly(ethylene-co-vinyl acetate) (PEVAc), polyvinyl acetate, silicones, and/or combinations thereof. In some embodiments, a filament may comprise 10-90 wt. %, 20-80%, or 30-70 wt. % elastic polymer. In some embodiments, a filament may comprise less than 90 wt. %, less than 80 wt. %, less than 70 wt. %, less than 60 wt. %, less than 50 wt. %, less than 40 wt. %, less than 30 wt. %, or less than 20 wt. % elastic polymer. In some embodiments, a filament my comprise more than 10 wt. %, more than 20 wt. %, more than 30 wt. %, more than 40 wt. %, more than 50 wt. %, more than 60 wt. %, more than 70 wt. %, or more than 80 wt. % elastic polymer.

Suitable bioresorbable polymers can include Poly(lactic-co-glycolic acid) (PLGA), polycaprolactone (PCL), poly (lactic acid) (PLA), PCL-PLA copolymers, polydioxanone, poly(trimethylene carbonate), PCL-poly(glycolic acid) copolymers, Poly(glycerol sebacate), Polyanhydrides, Polyphosphazenes, Poly(alkyl cyanoacrylate)s, poly(amino acids), Poly(propylene fumarate), and/or combinations thereof. In some embodiments, a filament may comprise 10-90 wt. %, 20-80%, or 30-70 wt. % bioresorbable polymer. In some embodiments, a filament may comprise less than 90 wt. %, less than 80 wt. %, less than 70 wt. %, less than 60 wt. %, less than 50 wt. %, less than 40 wt. %, less than 30 wt. %, or less than 20 wt. % bioresorbable polymer. In some embodiments, a filament my comprise more than 10 wt. %, more than 20 wt. %, more than 30 wt. %, more than 40 wt. %, more than 50 wt. %, more than 60 wt. %, more than 70 wt. %, or more than 80 wt. % bioresorbable polymer.

In some embodiments, a filament may include a plasticizer. For example, suitable plasticizers can include propylene glycol, P407, triethyl citrate, triacetin, dibutyl sebacate, and/or polyethylene glycol. In some embodiments, a filament may include 0.1 to 20 wt. % plasticizer or 1 to 10 wt. % plasticizer. In some embodiments, a filament may comprise less than 20 wt. %, less than 15 wt. %, less than 10 wt. %, less than 5 wt. %, or less than 1 wt. % plasticizer. In some embodiments, a filament may comprise more than 0.1 wt. %, more than 1 wt. %, more than 5 wt. %, more than 10 wt. %, or more than 15 wt. % plasticizer.

A length of the filament can be measured as a length between each arm, or, for embodiments comprising a single filament wrapping the circumference of the gastric residence system, the entire length of said circumferentially-wrapped filament. Either way, the length of a filament depends on the size of the gastric residence system and the number of arms. For example, for a stellate-shape gastric residence system comprise six arms, the length of a circumferentially-wrapped single filament may be 100-150 mm, 110-140 mm, or 120-130 mm in length. The length of the filament between any two adjacent arms of the six arms may be 18-24 mm or 20-22 mm.

In some embodiments, filaments made from Pellethane tubes may be stretched between two adjacent arms to create tension in the filament between the arms. For a stellate-shape gastric residence system comprise six arms, the length of a circumferentially-wrapped single filament comprising Pellethane tubes may be 90-130 mm or 100-120 mm in length. The length of the filament between any two adjacent arms of the six arms may be 18-22 mm.

The cross-sectional shape of a filament may be any of a variety of shapes including, but not limited to: a circle, an oval, a rectangle, or an annulus. The thickness or diameter of a filament may be 100-1000 microns, preferably 200 to 400 microns. In some embodiments, the thickness or diameter of a filament may be less than 1000 microns, less than 800 microns, less than 600 microns, less than 400 microns, or less than 200 microns. In some embodiments, the thickness or diameter of a filament may be more than 100 microns, more than 200 microns, more than 400 microns, more than 600 microns, or more than 800 microns.

In embodiments comprising a filament having a rectangular cross-section, the width of the filament (i.e., longer side of the rectangular cross-sectional measurement) may be 1-4 mm. In some embodiments, the width may be less than 4 mm, less than 3 mm, or less than 2 mm. In some embodiments, the width may be more than 2 mm, more than 3 mm, or more than 4 mm.

The force required to compress a gastric residence system having a filament may be quantified using a radial compression test, described in detail in the "Testing Methods" section, below. In some embodiments, the force required to compress a gastric residence system having a filament may be 1.25 to 5 times the force required to compress a gastric residence system without a filament to the same compressed diameter. In some embodiments, the force required to compress a gastric residence system having a filament may be less than 5 times, less than 4 times, less than 3 times, or less than 2 times the force required to compress a gastric residence system without a filament to the same compressed diameter. In some embodiments, the force required to compress a gastric residence system having a filament may be more than 1.25 times, more than 2 times, more than 3 times, or more than 4 times the force required to compress a gastric residence system without a filament to the same compressed diameter.

The force required to separate a filament from an arm tip may be quantified using a pullout force test, described in detail in the "Testing Methods" section, below. In some embodiments, the force required to separate a filament from its corresponding arm tip may be 0.5 to 10N or 2 to 6N. In some embodiments, the force required to separate a filament from its corresponding arm tip may be less than 10N, less than 9N, less than 8N, less than 7N, less than 6N, less than 5N, less than 4N, less than 3N, less than 2N, or less than 1N. In some embodiments, the force required to separate a filament from its corresponding arm tip may be more than 0.5N, more than 1N, more than 2N, more than 3N, more than 4N, more than 5N, more than 6N, more than 7N, more than 8N, or more than 9N. In some embodiments, the force required to separate a filament from its corresponding arm tip may decrease the longer the gastric residence system stays in a gastric environment.

In some embodiments, the force required to separate a filament from its corresponding arm tip may depend on the method used to secure the ends of the filament (i.e., knotted, heated, or no secured end). In some embodiments, the force required to separate a filament having knotted ends from its corresponding arm tip may be greater than the force required to separate a filament having heated ends from its corresponding arm tip. In some embodiments, the force required to separate a filament having knotted ends and the force required to separate a filament having heated ends from its corresponding arm tip may be greater than the force required to separate an unmodified filament (i.e., unsecured) from its corresponding arm tip.

Gastric Residence Systems Comprising Arms of Controlled Stiffness

In some embodiments, gastric residence systems described herein may additionally comprise arms of a controlled thickness to help prevent premature passage of the gastric residence system through a patient's pylorus.

By controlling the stiffness of an element of a gastric residence system that widens/enlarges the device to its open configuration (such as an arm), the risk of premature passage of the gastric residence system through the pylorus may be minimized. Accordingly, gastric residence systems having arms of controlled stiffness can help improve the efficacy and reliability of gastric residence systems. Additionally, gastric residence systems having arms of controlled stiffness can help prevent the gastric residence system from bending into configurations that allow for premature passage through the pylorus.

Gastric residence systems having arms of controlled stiffness require more force for the gastric residence system to bend into configurations suitable for premature passage through the pylorus. Described are gastric residence systems having controlled stiffness of any member that can widen or enlarge the gastric residence system into its open configuration (such as an arm) to help minimize the risk of the gastric residence system passing through the pylorus of a patient prematurely.

A gastric residence system having arms of a controlled stiffness is defined as a system comprising one or more arms having at least a portion of the arm made of a flexible material. In some embodiments, one or more arms may include a first segment comprising a first polymer composition and a second segment comprising a second polymer composition, wherein the second segment is more flexible than the first segment.

In some embodiments, the one or more arms extend radially. A proximal end of the one or more arms may be connected to a core. In some embodiments, a gastric residence system may include a plurality of arms extending radially. In some embodiments, a gastric residence system may include a plurality of arms connected to a core at the proximal end of each arm, the plurality of arms extending radially from the core. In some embodiments, a gastric residence system may comprise a plurality of arms, each arm comprising a first segment and a second segment.

The first polymer composition of a flexible arm of a gastric residence system may comprise a relatively stiff polymer. For example, suitable polymers may include polycaprolactone, polylactic acid, poly(lactic-co-glycolic acid), HPMCAS, high durometer TPU, and/or combinations thereof. Other examples may include hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly (vinyl pyrrolidone), ethylene/vinyl alcohol copolymer, poly (vinyl alcohol), carboxyvinyl polymer (Carbomer), Carbopol® acidic carboxy polymer, polycarbophil, poly (ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly (ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. In some embodiments, the first segment may also comprise one or more therapeutic agent or active pharmaceutical ingredients (APIs).

In some embodiments, the first polymer composition may comprise 10-90 wt. % or 50-70 wt. % polycaprolactone. In some embodiments, the first polymer composition may comprise less than 90 wt. %, less than 80 wt. %, less than 70 wt. %, less than 60 wt. %, less than 50 wt. %, less than 40 wt. %, less than 30 wt. %, or less than 20 wt. % polycaprolactone. In some embodiments, the first polymer composition may include more than 20 wt. %, more than 30 wt. %, more than 40 wt. %, more than 50 wt. %, more than 60 wt. %, more than 70 wt. %, or more than 80 wt. % polycaprolactone.

In some embodiments, the first polymer composition may comprise 10-90 wt. % or 30-70 wt. % therapeutic agent or API. In some embodiments, the first polymer composition may comprise less than 90 wt. %, less than 80 wt. %, less than 70 wt. %, less than 60 wt. %, less than 50 wt. %, less than 40 wt. %, less than 30 wt. %, or less than 20 wt. % therapeutic agent or API. In some embodiments, the first polymer composition may include more than 20 wt. %, more than 30 wt. %, more than 40 wt. %, more than 50 wt. %, more than 60 wt. %, more than 70 wt. %, or more than 80 wt. % therapeutic agent or API.

The second polymer composition of an arm of a gastric residence system disclosed herein may comprise a primary polymer that is flexible relative to the polymer of the first polymer composition. For example, suitable relatively "flexible" polymers may include one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, a polyethylene-co-vinyl acetate, and a silicone. In some embodiments, the second polymer composition of an arm may actually comprise the same primary polymer as the first polymer composition. For example, the second polymer composition may comprise polycaprolactone. However, unlike the first polymer composition, the second polymer composition may additionally comprise a soluble material (e.g., copovidone, poloxamers). Thus, upon hydration (e.g., within the stomach), the second polymer composition will soften such that the stiffness of the second polymer composition of the second segment is less than the first polymer composition of the first segment. Suitable commercially-available polymers may include Pathway™ TPU polymers (The Lubrizol Corporation), Tecoflex™ (The Lubrizol Corporation), Tecophilic™ (The Lubrizol Corporation), Carbothane™ (The Lubrizol Corporation), Isoplast® (The Lubrizol Corporation), Pebax® (Arkema), Texin® (Covestro), Chronoflex (AdvanSource Biomaterials), NEUSoft™ (PolyOne), and Medalist® TPEs (Teknor Apex).

In some embodiments, the second polymer composition may comprise 10-90 wt. % or 40-70 wt. % primary polymer. In some embodiments, the second polymer composition may comprise less than 90 wt. %, less than 80 wt. %, less than 70 wt. %, less than 60 wt. %, less than 50 wt. %, less than 40 wt. %, less than 30 wt. %, or less than 20 wt. % primary polymer. In some embodiments, the second polymer composition may include more than 20 wt. %, more than 30 wt. %, more than 40 wt. %, more than 50 wt. %, more than 60 wt. %, more than 70 wt. %, or more than 80 wt. % primary polymer.

In some embodiments, the second polymer composition may additionally include one or more water-soluble excipients (which may include one or more polymers to the primary polymer described previously). For example, suitable water-soluble excipients may include a copovidone, a poloxamer, and/or a polyethylene oxide. Suitable commercially-available water-soluble excipients can include Kolliphor P407 (poloxamer 407, poly(ethylene glycol)-block-poly(propylene glycol)-block-poly(ethylene glycol)), PEG-PCL, SIF (FaSSIF/FaSSGF powder from BioRelevant), EPO (dimethylaminoethyl methacrylate-butyl methacrylate-methyl methacrylate copolymer), Kollidon VA64 (vinylpyrrolidone-vinyl acetate copolymer in a ratio of 6:4 by mass), polyvinyl pyrrolidine.

The second polymer composition may comprise 5-70 wt. % or 10-40 wt. % water-soluble excipients. In some embodiments, the second polymer composition may comprise less than 70 wt. %, less than 60 wt. %, less than 50 wt. %, less than 40 wt. %, less than 30 wt. %, less than 20 wt. %, or less than 10 wt. % water-soluble excipients. In some embodiments, the second polymer composition may comprise more than 5 wt. %, more than 10 wt. %, more than 20 wt. %, more than 30 wt. %, more than 40 wt. %, more than 50 wt. %, or more than 60 wt. % water-soluble excipients.

In some embodiments, the second polymer composition may comprise additional excipients. For example, the second polymer composition may comprise bismuth subcarbonate, silica, vitamin E succinate, iron oxide, a polyethylene glycol, polyvinyl acetate and polyvinylcaprolactame-based graft copolymer (Soluplus®), sodium starch glycolate, and/or hydroxypropyl cellulose. In some embodiments, the second polymer composition may comprise 10-70 wt. % or 20-50 wt. % excipients. In some embodiments, the second polymer composition may comprise less than 70 wt. %, less than 60 wt. %, less than 50 wt. %, less than 40 wt. %, less than 30 wt. %, or less than 20 wt. % excipients. In some embodiments, the second polymer composition may comprise more than 10 wt. %, more than 20 wt. %, more than 30 wt. %, more than 40 wt. %, more than 50 wt. %, or more than 60 wt. % excipients.

In some embodiments, the second polymer composition may additionally comprise a therapeutic agent or API. The second polymer composition may comprise 20-80 wt. % or 40-60 wt. % therapeutic agent or API. In some embodiments, the second polymer composition may comprise less than 80 wt. %, less than 70 wt. %, less than 60 wt. %, less than 50 wt. %, less than 40 wt. %, or less than 30 wt. % therapeutic agent or API. In some embodiments, the second polymer composition may comprise more than 20 wt. %, more than 30 wt. %, more than 40 wt. %, more than 50 wt. %, more than 60 wt. %, or more than 70 wt. % therapeutic agent or API.

Some polymer materials that are useful for creating arms of controlled stiffness may have an added advantage in thermal stability. For example, gastric residence systems may experience temperature variation during shipping and distribution. Shipping data suggest that cargo temperature extremes may approach 60° C. in some climates (Singh et al, Packag. Technol. Sci. 2012; 25: 149-160). The polymers that comprise gastric residence systems should be physically stable at this temperature if they are to be shipped without cold chain packaging and storage.

Polycaprolactone is a preferred polymer for relatively stiff arms (or stiff/first segments), and thermoplastic polyurethane is a preferred polymer for creating arms of controlled stiffness (i.e., second segments). Polycaprolactone-based arms are physically stable when exposed to temperatures as high as 55° C., but melt if they reach 60° C. When stored in a capsule, arms that begin to melt can adhere to one another and prevent the gastric residence system from unfolding in the stomach. Thermoplastic polyurethanes such as Pathway PY-PT72AE provide improved thermal stability. Pathway PY-PT72AE is an amorphous material that does not undergo a clear melt transition but does soften at elevated temperatures.

When a gastric residence system comprising relatively stiff arms is compressed (e.g., by gastric waves or a radial compression test), the compression force is transferred to the more flexible core of the gastric residence system, resulting in a gastric residence system in a bended configuration that is capable of passing through the pylorus of a patient (i.e., an opening having a diameter of 20 mm).

Conversely, when a gastric residence system comprising relatively flexible arms (i.e., having a first segment and a second segment) is compressed, the second segment absorbs some of the compression force. Thus, the compression forces are not transferred to the core of the gastric residence system having relatively flexible arms as is the case with the gastric residence system having relatively stiff arms. To compress the stiff inner segments of the arms to pyloric size, greater force is required due to the shorter lever arm attached to the flexible core. This can mean that the gastric residence system having relatively flexible arms requires a greater compression force to bend it into a configuration small enough to pass through the pylorus of a patient (i.e., an opening having a diameter of 20 mm).

As the second segment of an arm of a gastric residence system having arms of controlled stiffness increases relative to the first segment, so too does the compression force required to compress the gastric residence system into a bended configuration small enough to pass through a pylorus (i.e., an opening having a diameter of 20 mm). (As long as the size of the stiff inner portion and the core is still larger than the diameter of the pylorus.)

The ratio of the first segment of a relatively flexible arm to the second segment of the arm may vary. If the first segment is too large in comparison to the second segment, the compression forces may transfer to the core of a gastric residence system too early, allowing the compression forces to compress the gastric residence system into a bended configuration small enough to prematurely pass through a pylorus. If the second segment is too large compared to the first segment, the second segment may too easily bend under the compression forces, allowing the forces to compress the gastric residence system into a bended configuration small enough to prematurely pass through a pylorus. Both scenarios result in a gastric residence system that is not as effective at resisting premature passage through the pylorus as desired.

An effective ratio of the first segment to the second segment of a flexible arm of a gastric residence system may vary. In some embodiments, the first segment may comprise from 10-90% of a length of an arm (as measured from the proximal end to the distal end). In some embodiments, the first segment may comprise less than 90%, less than 80%, less than 70%, less than 60%, less than 50%, less than 40%, less than 30%, or less than 20% of a length of an arm. In some embodiments, the first segment may comprise more than 10%, more than 20%, more than 30%, more than 40%, more than 50%, more than 60%, more than 70%, or more than 80% of a length of an arm. In some embodiments, the second segment may comprise from 10-90% of a length of an arm (as measured from the proximal end to the distal end). In some embodiments, the second segment may comprise less than 90%, less than 80%, less than 70%, less than 60%, less than 50%, less than 40%, less than 30%, or less than 20% of a length of an arm. In some embodiments, the second segment may comprise more than 10%, more than 20%, more than 30%, more than 40%, more than 50%, more than 60%, more than 70%, or more than 80% of a length of an arm.

System Polymeric Composition

The choice of the individual polymers for the carrier polymer, coupling polymer, and elastomer influence many properties of the system, such as drug elution rate (dependent on the carrier polymer, as well as other factors), the residence time of the system (dependent on the degradation of any of the polymers, principally the coupling polymers), the uncoupling time of the system if it passes into the intestine (dependent primarily on the enteric degradation rate of the coupling polymer, as discussed herein), and the shelf life of the system in its compressed form (dependent primarily on properties of the elastomer). As the systems will be administered to the gastrointestinal tract, all of the system components should be biocompatible with the gastrointestinal environment.

The rate of elution of drug from the carrier polymer-drug component is affected by numerous factors, including the composition and properties of the carrier polymer, which may itself be a mixture of several polymeric and non-polymeric components; the properties of the drug such as hydrophilicity/hydrophobicity, charge state, pKa, and hydrogen bonding capacity; and the properties of the gastric environment. In the aqueous environment of the stomach, avoiding burst release of a drug (where burst release refers to a high initial delivery of active pharmaceutical ingredient upon initial deployment of the system in the stomach), particularly a hydrophilic drug, and maintaining sustained release of the drug over a period of time of days to one or two weeks is challenging.

The residence time of the systems in the stomach is adjusted by the choice of coupling polymers used in the linker regions. The systems will eventually break down in the stomach, despite the use of enteric coupling polymers, as the mechanical action of the stomach and fluctuating pH will eventually weaken the enteric coupling polymers. Coupling polymers which degrade in a time-dependent manner in the stomach can also be used to adjust the time until the system breaks apart, and hence adjust the residence time. Once the system breaks apart, it passes into the intestines and is then eliminated.

The elastomer used in the systems is central to the shelf life of the systems. When the systems are compressed, the elastomer is subjected to mechanical stress. The stress in turn can cause polymer creep, which, if extensive enough, can prevent the systems from returning to their uncompacted configurations when released from the capsules or other container; this in turn would lead to premature passage of the system from the stomach. Polymer creep can also be temperature dependent, and therefore the expected storage conditions of the systems also need to be considered when choosing the elastomer and other polymer components.

The system components and polymers should not swell, or should have minimal swelling, in the gastric environment. The components should swell no more than about 20%, no more than about 10%, or preferably no more than about 5% when in the gastric environment over the period of residence.

The systems are optionally radiopaque, so that they can be located via abdominal X-ray if necessary. In some embodiments, one or more of the materials used for construction of the system is sufficiently radiopaque for X-ray visualization. In other embodiments, a radiopaque substance is added to one or more materials of the system, or coated onto one or more materials of the system, or are added to a small portion of the system. Examples of suitable radiopaque substances are barium sulfate, bismuth subcarbonate, bismuth oxychloride, and bismuth trioxide. It is preferable that these materials should not be blended into the polymers used to construct the gastric residence system, so as not to alter drug release from the carrier polymer, or desired properties of other system polymers. Metal striping or tips on a small portion of the system components can also be used, such as tungsten.

Methods of Manufacture and Methods of Treatment

Following is a description of various methods of manufacturing and methods of treatment. In particular, included is a detailed description of: Manufacture/assembly of system: three-dimensional printing; Manufacture/assembly of system: co-extrusion; Agent particle size and milling; Methods of Manufacture of Carrier Polymer-Agent (or Agent Salt) Components; Manufacture/assembly of system: affixing arms to central elastomer; Manufacture/assembly of system; Methods of Manufacturing Gastric Residence Systems Having a Filament; Methods of treatment using the gastric residence systems; and Kits and Articles of Manufacture.

Manufacture/Assembly of System: Three-Dimensional Printing

Three-dimensional printing of components of the gastric residence system, such as arm or arm segments, is performed using commercially-available equipment. Three-dimensional printing has been used for pharmaceutical preparation; see Khaled et al., "Desktop 3D printing of controlled release pharmaceutical bilayer tablets," International Journal of Pharmaceutics 461:105-111 (2014); U.S. Pat. No. 7,276,252; Alhnan et al., "Emergence of 3D Printed Dosage Forms: Opportunities and Challenges," Pharm. Res., May 18, 2016, PubMed PMID: 27194002); Yu et al., "Three-dimensional printing in pharmaceutics: promises and problems," J. Pharm. Sci. 97(9):3666-3690 (2008); and Ursan et al., "Three-dimensional drug printing: A structured review," J. Am. Pharm. Assoc. 53(2):136-44 (2013).

The initial feedstocks for three-dimensional printing are polymers or polymer blends (e.g. enteric polymers, time-dependent polymers, or blends of one or more of an agent, an agent salt, a drug, an excipient, etc., with a carrier polymer, enteric polymers, or time-dependent polymers). The polymer or ingredients which are to be used for one region of the segment or arm to be manufactured are mixed and pelletized using hot melt extrusion. The polymer or blended polymer material is extruded through a circular die, creating a cylindrical fiber which is wound around a spool.

Multiple spools are fed into the 3D printer (such as a Hyrel Printer, available from Hyrel 3D, Norcross, Georgia, United States), to be fed into their representative print heads. The print heads heat up and melt the material at the nozzle, and lay down a thin layer of material (polymer or polymer blend) in a specific position on the piece being manufactured. The material cools and hardens within seconds, and the next layer is added until the complete structure is formed. The quality of the dosage form is dependent on the feed rate, nozzle temperature, and printer resolution; feed rate and nozzle temperature can be adjusted to obtain the desired quality.

Three-dimensional printing can be used to manufacture individual arms, or segments of arms. Three-dimensional printing can also be used to prepare a bulk configuration, such as a consolidated "slab," similar to that prepared by co-extrusion methods described herein. The bulk configuration can be cut into individual pieces (that is, individual arms or individual segments) as needed.

In some embodiments of the invention, producing an entire arm of the gastric residence system by three-dimensional printing of the arm is contemplated. In some embodiments of the invention, producing a segment of an arm of the gastric residence system by three-dimensional printing of the segment of an arm is contemplated. In some embodiments, an arm or a segment thereof is produced by three-dimensional printing of adjacent portions of carrier polymer-agent or polymer-agent salt blend and linker material in a bulk configuration, such as a slab configuration. The three-dimensional printing can be followed by cutting the bulk configuration into pieces which have the desired shape of the arm or segment thereof. The three-dimensional printing can be followed by compression molding of portions of the bulk configuration into pieces which have the desired shape of the arm or segment thereof.

Three-dimensional printing is often accomplished by feeding a rod or fiber of a solid material to a print head, where it is melted and deposited with subsequent solidification, in a technique known as fused deposition modeling (sometimes also called extrusion deposition); see U.S. Pat. Nos. 5,121,329 and 5,340,433. The methods described herein for the manufacture of carrier polymer-drug components can also be used to manufacture feed material, which can be used in the manufacture via three-dimensional printing of components of the gastric residence systems.

Manufacture/Assembly of System: Co-Extrusion

Components of the gastric residence systems can be manufactured by co-extrusion. Most of the various configurations for the segments discussed herein, such as the “islands-in-the-sea” configurations, can be made by either three-dimensional printing or co-extrusion. However, co-extrusion is less expensive, and can be run as a continuous process, as opposed to three-dimensional printing, which is generally run as a batch process.

Co-extrusion of the “islands-in-the-sea” configuration is used in the textile industry and for production of fiber optics, but has rarely been applied in biomedical systems. See U.S. Pat. Nos. 3,531,368; 3,716,614; 4,812,012; and Haslauer et al., J. Biomed. Mater. Res. B Appl. Biomater. 103(5):1050-8 (2015)).

Co-extrusion of components of the gastric residence system, such as an arm, or a segment of an arm, can be performed using commercially-available equipment, combined with customized co-extruder plumbing and customized dies for the desired configuration. The initial feedstocks for co-extrusion are polymers or polymer blends (e.g. enteric polymers, time-dependent polymers, or blends of one or more of an agent, an agent salt, a drug, an excipient, etc., with a carrier polymer, enteric polymers, or time-dependent polymers). The polymer or ingredients which are to be used for one region of the segment or arm to be manufactured are mixed and pelletized using hot melt extrusion. The polymer pellets thus formed are placed into hoppers above single screw extruders and dried to remove surface moisture. Pellets are gravimetrically fed into individual single-screw extruders, where they are melted and pressurized for co-extrusion.

The appropriate molten polymers are then pumped through custom designed dies with multiple channels where they form the required geometry. The composite polymer block is cooled (water-cooled, air-cooled, or both) and cut or stamped into the desired shape, including, but not limited to, such shapes as triangular prisms, rectangular prisms, or cylinder sections (pie-shaped wedges).

In some embodiments of the invention, producing an entire arm of the gastric residence system by co-extruding the arm is contemplated. In some embodiments of the invention, producing a segment of an arm of the gastric residence system by co-extruding the segment of an arm is contemplated. In some embodiments, an arm or a segment thereof is produced by co-extruding adjacent portions of carrier polymer-agent or carrier polymer-agent salt blend and linker material in a bulk configuration, such as a slab configuration. The co-extruding can be followed by cutting the bulk configuration into pieces which have the desired shape of the arm or segment thereof. The co-extruding can be followed by compression molding of portions of the bulk configuration into pieces which have the desired shape of the arm or segment thereof.

In some embodiments, an arm or a segment thereof is produced by co-extruding adjacent portions of carrier polymer-agent or carrier polymer-agent salt blend and linker material in a bulk configuration, such as a slab configuration, while also co-extruding an additional polymer or polymers within the carrier polymer-agent or carrier polymer-agent salt blend, the linker material, or both the carrier polymer-agent (or agent salt) blend and the linker material. The co-extruding the additional polymer or polymers within the carrier polymer-agent or carrier polymer-agent salt blend, the linker material, or both the carrier polymer-agent (or agent salt) blend and the linker material can be performed in an islands-in-the-sea configuration. The co-extruding can be followed by cutting the bulk configuration into pieces which have the desired shape of the arm or segment thereof. The co-extruding can be followed by compression molding of portions of the bulk configuration into pieces which have the desired shape of the arm or segment thereof.

Agent Particle Size and Milling

Control of particle size used in the gastric residence systems is important for both optimal release of agent and mechanical stability of the systems. The particle size of the agents affects the surface area of the agents available for dissolution when gastric fluid permeates the carrier polymer-agent segments of the system. Also, as the arms of the systems are relatively thin in diameter (for example, 1 millimeter to 5 millimeters), the presence of a particle of agent of a size in excess of a few percent of the diameter of the arms will result in a weaker arm, both before the agent elutes from the device, and after elution when a void is left in the space formerly occupied by the agent particle. Such weakening of the arms is disadvantageous, as it may lead to premature breakage and passage of the system before the end of the desired residence period.

In one embodiment, the agent particles used for blending into the carrier polymer-agent components are smaller than about 100 microns in diameter. In another embodiment, the agent particles are smaller than about 75 microns in diameter. In another embodiment, the agent particles are smaller than about 50 microns in diameter. In another embodiment, the agent particles are smaller than about 40 microns in diameter. In another embodiment, the agent particles are smaller than about 30 microns in diameter. In another embodiment, the agent particles are smaller than about 25 microns in diameter. In another embodiment, the agent particles are smaller than about 20 microns in diameter. In another embodiment, the agent particles are smaller than about 10 microns in diameter. In another embodiment, the agent particles are smaller than about 5 microns in diameter.

In one embodiment, at least about 80% of the agent particles used for blending into the carrier polymer-agent components are smaller than about 100 microns in diameter. In another embodiment, at least about 80% of the agent particles are smaller than about 75 microns in diameter. In another embodiment, at least about 80% of the agent particles are smaller than about 50 microns in diameter. In another embodiment, at least about 80% of the agent particles are smaller than about 40 microns in diameter. In another embodiment, at least about 80% of the agent particles are smaller than about 30 microns in diameter. In another embodiment, at least about 80% of the agent particles are smaller than about 25 microns in diameter. In another embodiment, at least about 80% of the agent particles are smaller than about 20 microns in diameter. In another embodiment, at least about 80% of the agent particles are smaller than about 10 microns in diameter. In another embodiment, at least about 80% of the agent particles are smaller than about 5 microns in diameter.

In one embodiment, at least about 80% of the mass of the agent particles used for blending into the carrier polymer-agent components have sizes between about 1 micron and about 100 microns in diameter. In another embodiment, at least about 80% of the mass of the agent particles have sizes between about 1 micron and about 75 microns in diameter. In another embodiment, at least about 80% of the mass of the agent particles have sizes between about 1 micron and about 50 microns in diameter. In another embodiment, at least about 80% of the mass of the agent particles have sizes between about 1 micron and about 40 microns in diameter. In another embodiment, at least about 80% of the mass of the agent particles have sizes between about 1 micron and about 30 microns in diameter. In another embodiment, at least about 80% of the mass of the agent particles have sizes between about 1 micron and about 25 microns in diameter. In another embodiment, at least about 80% of the mass of the agent particles have sizes between about 1 micron and about 20 microns in diameter. In another embodiment, at least about 80% of the mass of the agent particles have sizes between about 1 micron and about 10 microns in diameter. In another embodiment, at least about 80% of the mass of the agent particles have sizes between about 1 micron and about 5 microns in diameter.

In one embodiment, at least about 80% of the mass of the agent particles used for blending into the carrier polymer-agent components have sizes between about 2 microns and about 100 microns in diameter. In another embodiment, at least about 80% of the mass of the agent particles have sizes between about 2 microns and about 75 microns in diameter. In another embodiment, at least about 80% of the mass of the agent particles have sizes between about 2 microns and about 50 microns in diameter. In another embodiment, at least about 80% of the mass of the agent particles have sizes between about 2 microns and about 40 microns in diameter. In another embodiment, at least about 80% of the mass of the agent particles have sizes between about 2 microns and about 30 microns in diameter. In another embodiment, at least about 80% of the mass of the agent particles have sizes between about 2 microns and about 25 microns in diameter. In another embodiment, at least about 80% of the mass of the agent particles have sizes between about 2 microns and about 20 microns in diameter. In another embodiment, at least about 80% of the mass of the agent particles have sizes between about 2 microns and about 10 microns in diameter. In another embodiment, at least about 80% of the mass of the agent particles have sizes between about 2 microns and about 5 microns in diameter.

In one embodiment, at least about 80% of the mass of the agent particles used for blending into the carrier polymer-agent components have sizes between about 5 microns and about 100 microns in diameter. In another embodiment, at least about 80% of the mass of the agent particles have sizes between about 5 microns and about 75 microns in diameter. In another embodiment, at least about 80% of the mass of the agent particles have sizes between about 5 microns and about 50 microns in diameter. In another embodiment, at least about 80% of the mass of the agent particles have sizes between about 5 microns and about 40 microns in diameter. In another embodiment, at least about 80% of the mass of the agent particles have sizes between about 5 microns and about 30 microns in diameter. In another embodiment, at least about 80% of the mass of the agent particles have sizes between about 5 microns and about 25 microns in diameter. In another embodiment, at least about 80% of the mass of the agent particles have sizes between about 5 microns and about 20 microns in diameter. In another embodiment, at least about 80% of the mass of the agent particles have sizes between about 5 microns and about 10 microns in diameter.

The particle size of the agents can be readily adjusted by milling. Several milling techniques are available to reduce larger particles to smaller particles of desired size. Fluid energy milling is a dry milling technique which uses inter-particle collisions to reduce the size of particles. A type of fluid energy mill called an air jet mill shoots air into a cylindrical chamber in a manner so as to maximize collision between agent particles. Ball milling utilizes a rolling cylindrical chamber which rotates around its principal axis. The agent and grinding material (such as steel balls, made from chrome steel or CR-NI steel; ceramic balls, such as zirconia; or plastic polyamides) collide, causing reduction in particle size of the agent. Ball milling can be performed in either the dry state, or with liquid added to the cylinder where the agent and the grinding material are insoluble in the liquid. Further information regarding milling is described in the chapter by R. W. Lee et al. entitled "Particle Size Reduction" in Water-Insoluble Drug Formulation, Second Edition (Ron Liu, editor), Boca Raton, Florida: CRC Press, 2008; and in the chapter by A. W. Brzeczko et al. entitled "Granulation of Poorly Water-Soluble Drugs" in Handbook of Pharmaceutical Granulation Technology, Third Edition (Dilip M. Parikh, editor), Boca Raton, Florida: CRC Press/Taylor & Francis Group, 2010 (and other sections of that handbook). Fluid energy milling (i.e., air jet milling) is a preferred method of milling, as it is more amenable to scale-up compared to other dry milling techniques such as ball milling.

Substances can be added to the agent material during milling to assist in obtaining particles of the desired size, and minimize aggregation during handling. Silica (silicon dioxide, SiO2) is a preferred milling additive, as it is inexpensive, widely available, and non-toxic. Other additives which can be used include silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants. In particular, hydrophobic particles less than 5 microns in diameter are particularly prone to agglomeration, and hydrophilic additives are used when milling such particles. A weight/weight ratio of about 0.1% to about 5% of milling additive, such as silica, can be used for fluid milling or ball milling, or about 0.1% to about 4%, about 0.1% to about 3%, about 0.1% to about 2%, about 0.1% to about 1%, about 1% to about 5%, about 1% to about 4%, about 1% to about 3%, about 1% to about 2%, or about 0.1%, about 0.5%, about 1%, about 2%, about 3%, about 4% or about 5%.

After milling, particles can be passed through meshes of appropriate size to obtain particles of the desired size. To obtain particles of a desired maximum size, particles are passed through a mesh with holes of the maximum size desired; particles which are too large will be retained on the mesh, and particles which pass through the mesh will have the desired maximum size. To obtain particles of a desired minimum size, particles are passed through a mesh with holes of the minimum size desired; particles which pass through the mesh are too small, and the desired particles will be retained on the mesh.

Methods of Manufacture of Carrier Polymer-Agent (or Agent Salt) Components

Blending temperatures for incorporation of the agent (or a pharmaceutically acceptable salt thereof) into polymeric matrices typically range from about 80° C. to about 120° C., although higher or lower temperatures can be used for polymers which are best blended at temperatures outside that range. When agent (or salt thereof) particles of a particular size are used, and it is desired that the size of the particles be maintained during and after blending, blending can be done at temperatures below the melting point of the agent (or salt thereof), so as to maintain the desired size of the particles. Otherwise, temperatures can be used which melt both the polymer and the agent (or salt thereof). Blending temperatures should be below the degradation temperature of the agent (or salt thereof). In one embodiment, less than about 2% of the agent (or salt thereof) is degraded during manufacture. In one embodiment, less than about 1.5% of the agent (or salt thereof) is degraded during manufacture. In one embodiment, less than about 1% of the agent (or salt thereof) is degraded during manufacture. In one embodiment, less than about 0.75% of the agent (or salt thereof) is degraded during manufacture. In one embodiment, less than about 0.5% of the agent (or salt thereof) is degraded during manufacture. In one embodiment, less than about 0.4% of the agent (or salt thereof) is degraded during manufacture. In one embodiment, less than about 0.3% of the agent (or salt thereof) is degraded during manufacture. In one embodiment, less than about 0.2% of the agent (or salt thereof) is degraded during manufacture. In one embodiment, less than about 0.15% of the agent (or salt thereof) is degraded during manufacture. In one embodiment, less than about 0.1% of the agent (or salt thereof) is degraded during manufacture. In one embodiment, less than about 0.05% of the agent (or salt thereof) is degraded during manufacture. In one embodiment, less than about 0.04% of the agent (or salt thereof) is degraded during manufacture. In one embodiment, less than about 0.03% of the agent (or salt thereof) is degraded during manufacture. In one embodiment, less than about 0.02% of the agent (or salt thereof) is degraded during manufacture. In one embodiment, less than about 0.01% of the agent (or salt thereof) is degraded during manufacture.

Hot melt extrusion can be used to prepare the carrier polymer-agent (or agent salt) components. Single-screw or, preferably, twin-screw systems can be used. As noted, if it is desired that the size of the particles be maintained during and after blending, carrier polymers should be used which can be melted at temperatures which do not degrade the agent or salt thereof. Otherwise, temperatures can be used which melt both the polymer and the agent or salt thereof.

Melting and casting can also be used to prepare the carrier polymer-agent (or salt thereof) components. The carrier polymer and agent (or salt thereof), and any other desired components, are mixed together. The carrier polymer is melted and the melt is mixed so that the agent (or salt thereof) particles are evenly distributed in the melt, poured into a mold, and allowed to cool.

Solvent casting can also be used to prepare the carrier polymer-agent (or salt thereof) components. The polymer is dissolved in a solvent, and particles of agent (or salt thereof) are added. If the size of the agent (or salt thereof) particles are to be maintained, a solvent should be used which does not dissolve the agent (or salt thereof) particles, so as to avoid altering the size characteristics of the particles; otherwise, a solvent which dissolves both the polymer and agent (or salt thereof) particles can be used. The solvent-carrier polymer-agent (or salt thereof) particle mixture (or solvent-carrier particle-agent/agent salt solution), is then mixed to evenly distribute the particles (or thoroughly mix the solution), poured into a mold, and the solvent is evaporated.

Manufacture/Assembly of System: Affixing Arms to Central Elastomer

For a stellate gastric residence system, such as that shown in FIG. 1A, the arms of the gastric residence system can be affixed to the central elastomer in a number of ways. The central polymer can be cast or molded with short "asterisk" arms, and a linker polymer can be used to affix the arms to the asterisk arms of the central elastomer. Alternatively, the central elastomer can be formed in a mold into which the proximal ends of the arms protrude. The elastomer sets, cures, or otherwise hardens into its desired form with a portion of the arms extending into the body of the central elastomer. Alternatively, the central elastomer can be prepared with cavities into which the arms can be firmly inserted.

The invention thus includes a method of making a gastric residence system, comprising preparing at least three arms formed from a material comprising any drug-carrier polymer-excipient formulation as disclosed herein; and attaching the arms to a central elastomer to form a gastric residence system. The arms can comprise at least one segment with a release rate-controlling polymer film. The arms of the gastric residence system project radially from the central elastomer, such as in a "hub and spoke" arrangement. A preferred number of arms is six. However, stellate systems with three, four, five, seven, or eight arms can also be used.

In some embodiments, arms comprising any carrier polymer-agent formulation can be heat-welded, solvent-welded, or otherwise affixed to other elements, including disintegrating matrices, coupling polymers, or interfacing polymers, which are then affixed to a central elastomer. In some embodiments, the arms are directly affixed to a central elastomer. Disintegrating matrices, coupling polymers, or interfacing polymer segments can be welded or otherwise affixed to the central elastomer prior to affixing the arms.

In some embodiments, arms comprising any drug-carrier polymer-excipient formulation as disclosed herein can be heat-welded to polycaprolactone segments, such as short polycaprolactone "asterisk" arms affixed to a central elastomer. Linker segments can be welded to the short "asterisk" arms prior to affixing the drug-carrier polymer-excipient formulation arms. Heat welding of drug-carrier polymer-excipient formulation arms to MW 80,000 PCL segments at temperatures between 140° C. to 170° C., followed by cooling for 24 hours at 8° C., resulted in stronger welds. Thus, in one embodiment, attaching the arms comprising any drug-carrier polymer-excipient formulation as disclosed herein to a central elastomer to form a gastric residence system, can comprise heat-welding the arms to other system components, such as asterisk arms or other segments comprising at least about 90%, at least about 95%, or at least about 99% polycaprolactone (such as MW 80,000 PCL), at a temperature between about 140° C. to about 170° C., followed by cooling of the welded members attached to other system components for about 12 to about 48 hours at a temperature of about 2° C. to about 14° C., such as about 5° C. to about 10° C., or about 8° C. The other system components can alternatively be linker elements.

Manufacture/Assembly of System

Once the arms of the gastric residence system have been affixed to the central elastomer, the system is ready to be folded into its compacted configuration and placed into a capsule for storage, transport, and eventual administration. The system can be folded in an automated mechanical process, or by hand, and placed into a capsule of the appropriate size and material. More detail regarding manufacture and assembly of gastric residence systems, and of packaging the gastric residence system into capsules, can be found in International Patent Application Nos. WO 2015/191920, WO 2015/191925, WO 2017/070612, WO 2017/100367, and PCT/US2017/034856.

Methods of Manufacturing Gastric Residence Systems Having a Filament

As described, a filament of a gastric residence system may be connected to a tip of an arm of the gastric residence system. If not properly connected, the arm may translate along the filament when the gastric residence system is compressed/bent, which may compromise the ability of the filament to help prevent premature passage of the gastric residence system through the pylorus. Thus, following is a description of methods of manufacturing gastric residence systems having a filament.

Figures 6A, 6B, 6C:
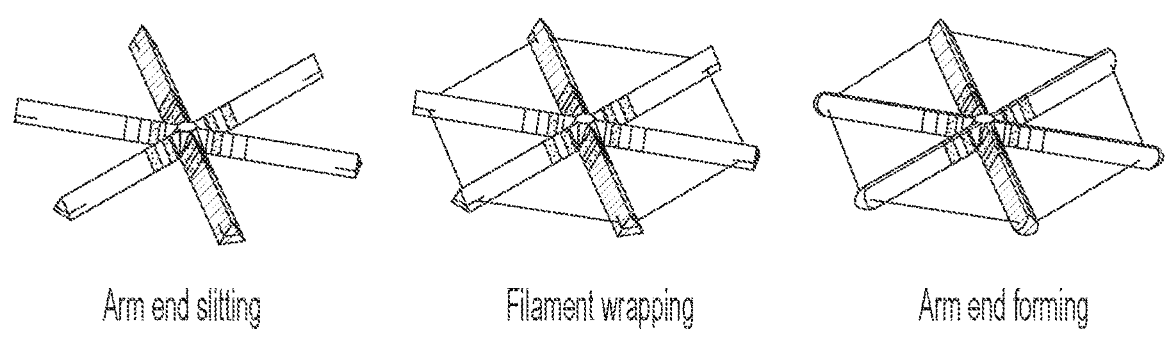
FIGS. 6A-6C show stages of preparing a gastric residence system with filament, according to some embodiments.

In some embodiments, a filament may be attached to the arms of pre-assembled gastric residence systems by notching, wrapping, and end forming. The gastric residence systems may be assembled with specially-formulated tips at each distal end of each arm. Each tip of each arm may be notched with a razor blade or circular saw to form a notch in the tip, as shown in FIG. 6A. FIG. 6B shows a filament that has been wrapped circumferentially around the arms of the gastric residence system and fed through each notch. In some embodiments, the filament may be wrapped using a winding fixture with controlled tension. FIG. 6C shows notches that have been closed and rounded to secure the filament. In some embodiments, the notches may be closed using a fixture that applies heat and pressure to the end of each arm through a heated die, leaving a rounded surface at the end of the arm.

Figure 7:
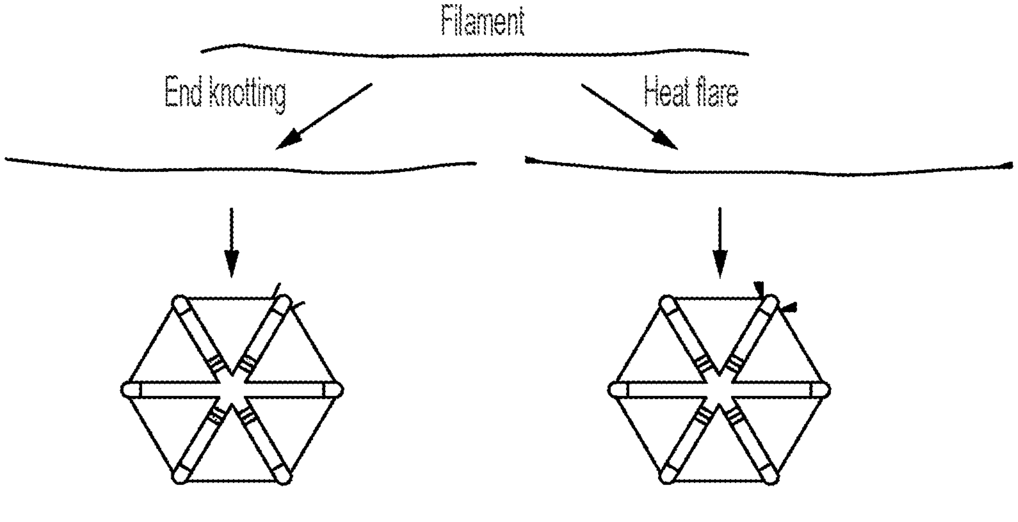
FIG. 7 shows two methods of securing the filament, according to some embodiments.

After wrapping a filament to connect two or more arms, the ends of the filament can be secured. FIG. 7 shows two different methods of securing the ends of a filament. The two ends of the filament may be secured first by overlapping them within the notch of a single arm. As the gastric residence system bends within the stomach during gastric residence, tension is applied to the filament and the two free filament ends may slip through the notch and detach from the arm. Thus, to better secure the filament ends, the filament ends can be enlarged by knotting and/or heat flaring. In some embodiments, the ends of the filament may be knotted and/or heated prior to attaching to the gastric residence system.

Figure 8:
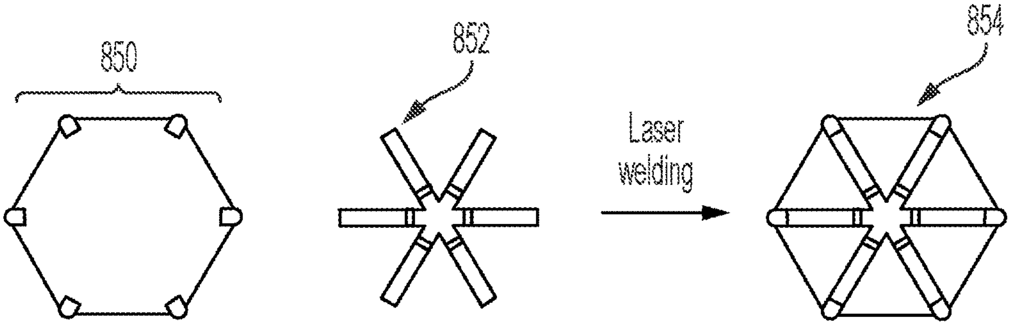
FIG. 8 shows a method of manufacturing a gastric residence system, according to some embodiments.

In some embodiments, the filament may be attached to a plurality of arm tips prior to attaching the arm tips to the rest of the gastric residence system. For example, the filament and arm tips may be manufactured by injection molding or insert molding (e.g., overmolding the tips onto an existing filament). FIG. 8 shows an example of a manufacturing process that includes forming the filament and arm tips by injection molding. As shown, gastric residence system 852 may be inserted into the injection molded filament and arm tips (850). Gastric residence system 852 maybe welded to the filament and arm tips 850 to form a completed gastric residence system having a filament 854.

Methods of Treatment Using the Gastric Residence Systems

The gastric residence systems can be used to treat conditions requiring administration of a drug or agent over an extended period of time. In a preferred embodiment, a gastric residence system is administered to a human. For long-term administration of agents or drugs which are taken for months, years, or indefinitely, administration of a gastric residence system periodically, such as once weekly or once every two weeks can provide substantial advantages in patient compliance and convenience. Accordingly, the gastric residence systems of the invention can be administered once every three days, once every five days, once weekly, once every ten days, or once every two weeks. The administration frequency is timed to coincide with the designed gastric residence period of the gastric residence system which is administered, so that at about the same time that a gastric residence system passes out of the stomach after its residence period, a new gastric residence system is administered.

Once a gastric residence system has been administered to a patient, the system provides sustained release of agent or drug over the period of gastric retention. After the period of gastric retention, the system degrades and passes out of the stomach. Thus, for a system with a gastric retention period of one week, the patient will swallow (or have administered to the stomach via other methods) a new system every week. Accordingly, in one embodiment, a method of treatment of a patient with a gastric retention system of the invention having a gastric residence period of a number of days D (where D-days is the gastric residence period in days), over a total desired treatment period T-total (where T-total is the desired length of treatment in days) with the agent or drug in the system, comprises introducing a new gastric residence system every D-days into the stomach of the patient, by oral administration or other methods, over the total desired treatment period. The number of gastric residence systems administered to the patient will be (T-total) divided by (D-days). For example, if treatment of a patient for a year (T-total=365 days) is desired, and the gastric residence period of the system is 7 days (D-days=7 days), approximately 52 gastric residence systems will be administered to the patient over the 365 days, as a new system will be administered once every seven days.

Alternatively, the patient can swallow (or have administered to the stomach via other methods) a new gastric residence system at the end of the effective release period of the gastric residence system. The "effective release period" or "effective release time" is the time over which the gastric residence system releases an effective amount of the agent contained in the system. Accordingly, in one embodiment, a method of treatment of a patient with a gastric residence system of the invention having an effective release period of a number of days E (where E-days is the effective release period in days), over a total desired treatment period T-total (where T-total is the desired length of treatment in days) with the agent in the system, comprises introducing a new gastric residence system every E-days into the stomach of the patient, by oral administration or other means, over the total desired treatment period. The number of gastric residence systems administered to the patient will be (T-total) divided by (E-days). For example, if treatment of a patient for a year (T-total=365 days) is desired, and the effective release period of the system is 7 days (E-days=7 days), approximately 52 gastric residence systems will be administered to the patient over the 365 days, as a new system will be administered once every seven days.

Kits and Articles of Manufacture

Also provided herein are kits for treatment of patients with the gastric residence systems of the invention. The kit may contain, for example, a sufficient number of gastric residence systems for periodic administration to a patient over a desired total treatment time period. If the total treatment time in days is (T-total), and the gastric residence systems have a residence time of (D-days), then the kit will contain a number of gastric residence systems equal to ((T-total) divided by (D-days)) (rounded to an integral number), for administration every D-days. Alternatively, if the total treatment time in days is (T-total), and the gastric residence systems have an effective release period of (E-days), then the kit will contain a number of gastric residence systems equal to ((T-total) divided by (E-days)) (rounded to an integral number), for administration every E-days. The kit may contain, for example, several gastric residence systems in containers (where the containers may be capsules) and may optionally also contain printed or computer readable instructions for dosing regimens, duration of treatment, or other information pertinent to the use of the gastric residence systems and/or the agent or drug contained in the gastric residence systems. For example, if the total treatment period prescribed for the patient is one year, and the gastric residence system has a residence time of one week or an effective release period of one week, the kit may contain 52 capsules, each capsule containing one gastric residence system, with instructions to swallow one capsule once a week on the same day (e.g., every Saturday).

Articles of manufacture, comprising a sufficient number of gastric residence systems for periodic administration to a patient over a desired total treatment time period, and optionally comprising instructions for dosing regimens, duration of treatment, or other information pertinent to the use of the gastric residence systems and/or the agent or drug contained in the gastric residence systems, are also included in the invention. The articles of manufacture may be supplied in appropriate packaging, such as dispensers, trays, or other packaging that assists the patient in administration of the gastric residence systems at the prescribed interval.

Testing Methods

3-Point Bending Test: A "flexural modulus" of a material is an intrinsic property of a material computed as the ratio of stress to strain in flexural deformation of the material as measured by a 3-point bending test. Although the linkers are described herein as being components of the gastric residence system, the flexural modulus of the material of the polymeric material may be measured in isolation. For example, the polymeric linker in the gastric residence system may be too short to measure the flexural modulus, but a longer sample of the same material may be used to accurately determine the flexural modulus. The longer sample used to measure the flexural modulus should have the same cross-sectional dimensions (shape and size) as the polymeric linker used in the gastric residence system. The flexural modulus is measured using a 3-point bending test in accordance with the ASTM standard 3-point bending test (ASTM D790) using a 10 mm distance between supports and further modified to accommodate materials with non-rectangular cross-sections. The longest line of symmetry for the cross section of the polymeric linker should be positioned vertically, and the flexural modulus should be measured by applying force downward. If the longest line of symmetry for the cross section of the polymeric linker is perpendicular to a single flat edge, the single flat edge should be positioned upward. If the cross-section of the polymeric linker is triangular, the apex of the triangle should be faced downward. As force is applied downward, force and displacement are measured, and the slope at the linear region is obtained to calculate the flexural modulus.

Figure 9:
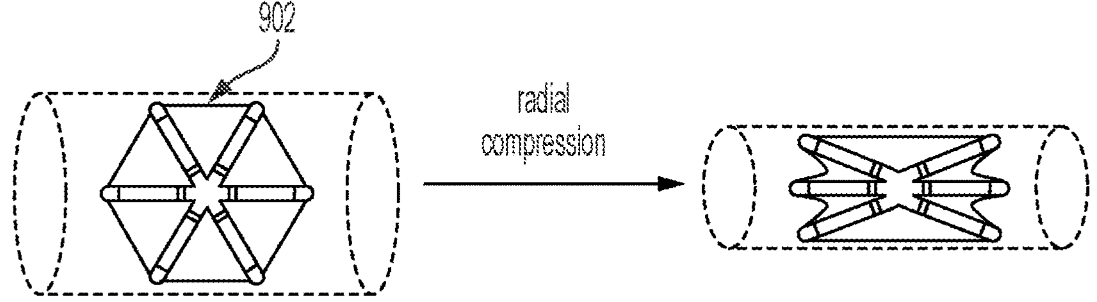
FIG. 9 shows a method of testing radial compression using an iris mechanism, according 10 to some embodiments.

Radial Force Compression Test: FIG. 9 shows a radial force compression test using an iris mechanism. Specifically, gastric residence system 902 depicted in FIG. 9 comprises a filament wrapped circumferentially about a stellate-shaped gastric residence system comprising six arms. The instrument (i.e., iris tester) used to measure radial force compression was a Blockwise Model TTR2 Tensile Testing Machine with Model RLU124 Twin-Cam™ Radial Compression Station, 60 mm D×124 mm L.

The gastric residence system that was measured was placed in the iris tester such that the plane of the gastric residence system was parallel to the axis of the iris cylinder. Four arm tips were placed in contact with the interior wall of the iris tester (in the case of gastric residence systems comprising six arms), where two arms are angled upwards and two arms are angled downwards. Two additional arms were oriented parallel to the axis of the iris cylinder.

Figure 10A:
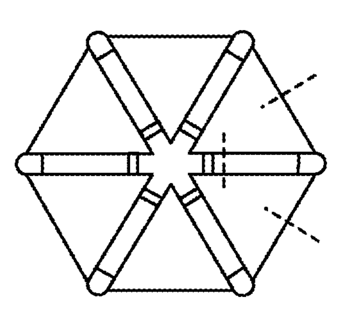
FIG. 10A and FIG. 10B show a pullout force test of a gastric residence system having a filament, according to some embodiments.
Figure 10B:
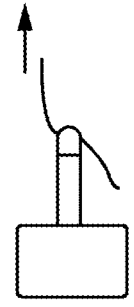

Pullout Force Test: FIGS. 10A and 10B show a method of testing filament adhesion strength. As described previously, the filament may be attached to a distal end of an arm. In cases where a single filament connects more than two arms, the filament may be connected to the distal end of each arm to prevent translation of the arm along the filament when the gastric residence system is bent by gastric forces. Thus, the pullout force test described herein can quantify the amount of force required to separate the filament from the distal end of an arm.

Gastric residence systems having six arms and a filament were prepared and the arms were isolated by cutting the elastomeric core into six parts. The filament was cut between each arm. The tensile force required to pull the filament out of each arm tip was measured using an Instron 3340 Series Universal Testing System by gripping the base of the arm and one end of the filament.

Double Funnel Durability Test: A double funnel test may be used to quantify the durability and/or failure mode of a gastric residence system. The durability of a gastric residence system can help prevent the premature breaking or weakening due to repeated gastric wave/forces (and early passage through the pylorus) of a gastric residence system. To test a gastric residence system using a double funnel test, the system to be tested is gripped at its center (i.e., core) by a ring attached to a linear actuator. The gastric residence system is repeatedly moved upwards and downwards into facing cone-shaped cavities, causing the arms of gastric residence system to bend back and forth with reference to the core. The cone-shaped cavities are facing each other such that the vertex of the cones are opposite each other and the bases of each cone are proximate one another. This upwards and downwards motion is repeated for hundreds of cycles or until the gastric residence system breaks. Different specific failure modes may include a breakage at a connection point (e.g., arm-to-core or first segment-to-second segment) or tearing of the silicone core. The number of cycles to failure and the force required to bend the gastric residence system may be quantified. The test may be performed with the gastric residence system submerged in aqueous media (e.g., simulated gastric fluid) and at body temperature.

Planar Circumferential Bend Durability Test: A planar circumferential test may be used to quantify the durability and/or failure mode of a gastric residence system. In particular, the planar circumferential bend durability test can test a gastric residence system by positioning it onto a puck having four grips each in contact with arms of the gastric residence system. The grips are connected to a rotational actuator that applies force to the arms in a circumferential motion. This motion causes the arms to spread within the plane of the gastric residence system. The motion is repeated for hundreds of cycles or until the gastric residence system breaks. Different specific failure modes may include a breakage at a connection point (e.g., arm-to-core or first segment-to-second segment) or tearing of the silicone core. The number of cycles to failure and the force required to bend the gastric residence system may be quantified. The test may be performed with the gastric residence system submerged in aqueous media (e.g., simulated gastric fluid) and at body temperature.

Melt Flow Index (MFI): The melt flow index (MFI) is a measurement of viscosity at low shear, measured in grams of material that flow through a die in 10 minutes at a set temperature and applied weight. These measurements are performed using a Ray-Ran 6MPCA Advanced Melt Flow System, with a weight of 2.16 kg (but can be with a range of standardized weights) and following Procedure A of ASTM D1238 "Standard Test Method for Melt Flow Rates of Thermoplastics by Extrusion Plastometer."

Tensile Test: An Instron machine having custom-made grips (Figure C) can be used to evaluate the ultimate tensile strength (UTS) of the bond between any combination of stellate components: (1) in a variety of incubation media; (2) at several times of incubation; and (3) at room temperature or body temperature (37-40° C.). A low ultimate tensile strength indicates a potential failure point in the stellate. Using formulation and process optimization, tensile strength can be maximized for ideal stellate performance.

For testing stellate arms with a triangular cross-section, custom-made grips can be used having one flat plate and one notched plate. The apex of the triangular arm sits in the notch, in order to distribute the pressure from the plates more evenly across the three lengthwise faces of the triangular arm.

Tensile testing was performed using an Instron 3342 Series. A series of hot-melt extruded, thermally bonded equilateral triangular prisms with a 3.33 mm triangular base is gripped using pneumatic actuation. The crosshead moves upward at 5-500 mm/minute depending on the elasticity of the materials tested. The instrument records Force (N) v. Displacement (mm), and the maximum force is divided by the cross-sectional area at the interface to calculate ultimate tensile strength (stress).

Drug Release Rate Test: Release rate of drug is tested in fasted-state simulated gastric fluid (FaSSGF). FaSSGF was prepared as follows, according to the manufacturer's instructions (biorelevant.com). 975 mL deionized water and 25 mL of 1N hydrochloric acid were mixed in a 1 L glass media bottle. The pH was adjusted to 1.6 using 1N HCl or NaOH as needed. 2.0 grams of NaCl was added and mixed in. Just before use, 60 mg of Biorelevant powder was mixed into the solution. The composition of FaSSGF was taurocholate (0.08 mM), phospholipids (0.02 mM), sodium (34 mM), chloride (59 mM). Carrier polymer-agent compositions were formed into drug-loaded polymer arms by blending polymer powder and active pharmaceutical ingredient, and extruding. Arms were coated with release rate-modulating polymer films by dissolving the film polymer in an appropriate solvent, typically ethyl acetate or acetone, and pan-coating or dip-coating the arm in the solution of film polymer. Coated arms are then placed in a vessel containing FaSSGF, incubated at 37° C., and typically sampled at least four times over a seven-day period. Drug content was measured by HPLC. Samples were stored for no more than 3 days at 4° C. prior to analysis. At each measurement time point, in order to maintain sink conditions, the entire volume of release media was replaced with fresh solution pre-equilibrated to 37° C.

EXAMPLES

Figure 11:
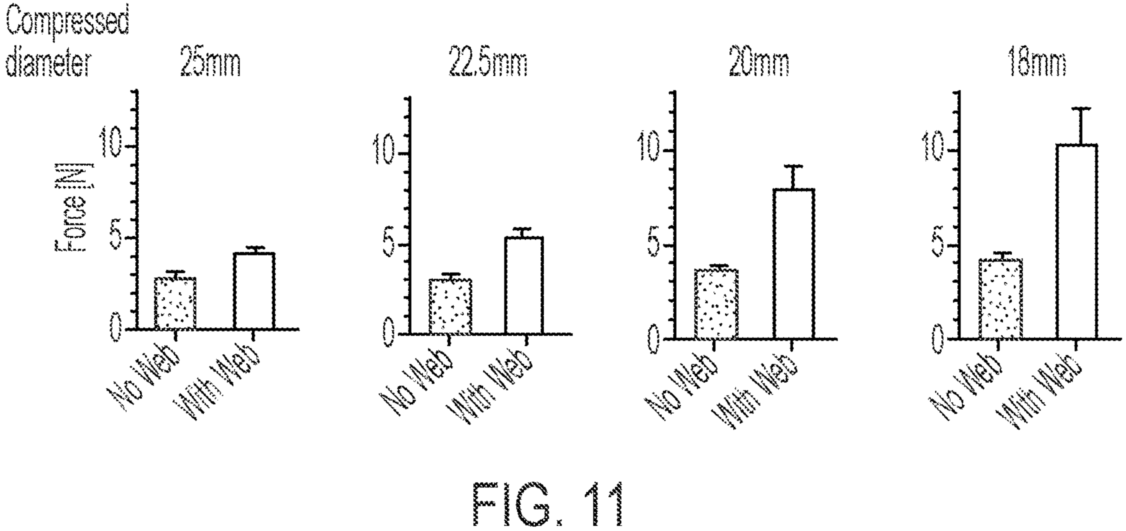
FIG. 11 shows radial force data for gastric residence systems without a filament and gastric residence systems having filament, according to some embodiments.

Example 1: The radial force required to compress gastric residence systems to various iris diameters was tested using the radial force test described in detail previously. As shown in FIG. 11, a gastric residence system with a filament and a gastric residence system without a filament were tested. As shown, the discrepancy between the force required to compress the gastric residence system with a filament and the gastric residence system without a filament increases as the compressed diameter decreases. The results demonstrate that at compressed diameters small enough for the gastric residence system to prematurely pass through the pylorus (i.e., diameters of 20 mm and less), the force required to compress the gastric residence system with a filament is at least two times greater than the force required to compress the gastric residence system without a filament.

Figure 12:
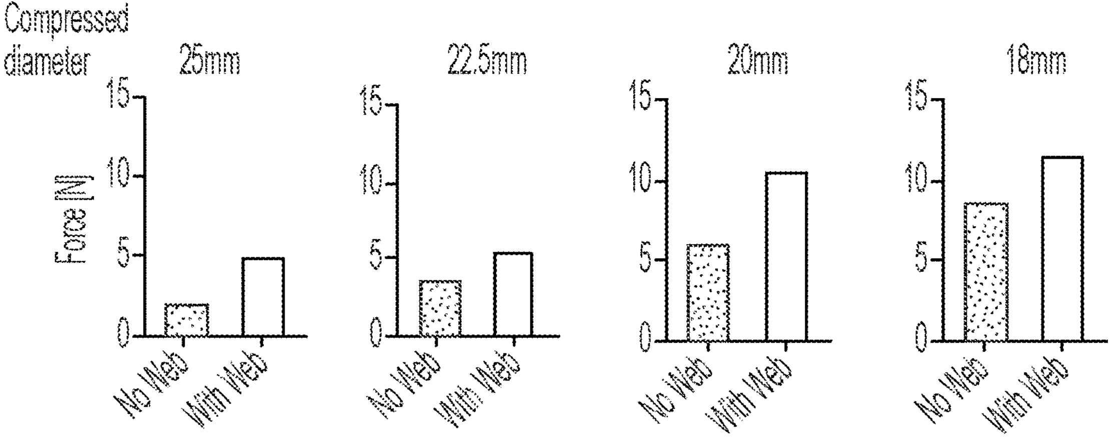
FIG. 12 shows radial force data for gastric residence systems without a filament and comprising flexible arms and gastric residence systems having filament and stiff arms, according to some embodiments.

Example 2: The radial force required to compress gastric residence systems to various iris diameters was tested using the radial force test described in detail previously. In particular, a gastric residence systems having relatively flexible arms (compared to the gastric residence systems tested in Example 1) with and without a filament were tested. Like the gastric residence systems tested in Example 1, FIG. 12 shows that the discrepancy between the force required to compress the gastric residence system with a filament and the gastric residence system without a filament increases as the compressed diameter decreases. Further, as shown in the figure, the force required to compress the gastric residence system with the filament to a compressed diameter small enough to prematurely pass through the pylorus (i.e., diameters of 20 mm and less) is approximately one and a half times greater than the force required to compress the gastric residence system without a filament to the same compressed diameter.

Figure 13:
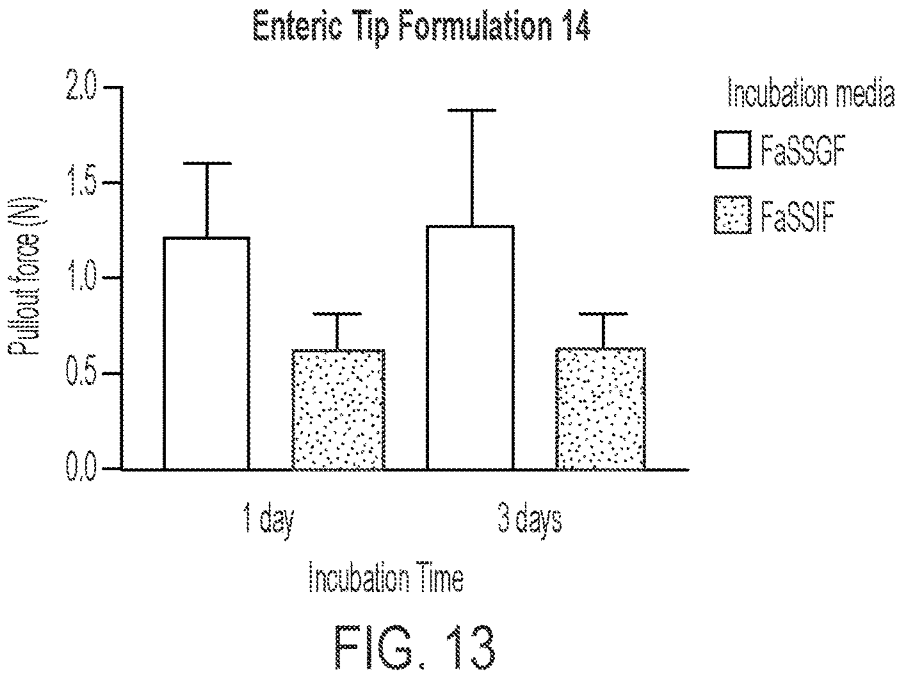
FIG. 13 shows pullout force data for gastric residence systems comprising filament and enteric tips (formulation 14), according to some embodiments.

Example 3: The pullout force required to separate a filament from an arm tip was tested at various incubation settings. As shown in FIG. 13, the pullout force was tested for filaments connected to arm tips having formulation 14 (shown in Table 1) using the pullout force testing procedure described in detail previously. Tips comprising this formulation are designed to remain connected to the filament in a highly acidic, or gastric environment, and separate or slip from the filament in an intestinal environment as the gastric residence system components pass through the intestine of a patient. Adhesion force was measured after samples were incubated in fasted state simulated gastric fluid (FaSSGF, pH 1.6) or fasted state simulated intestinal fluid (FaSSIF, pH 6.5) for both 1 and 3 days. As shown in the Figure, the length of incubation (i.e., 1 day or 3 days) only marginally affected the pullout force of samples incubated in the fasted state simulated gastric fluid and the fasted state simulated intestinal fluid. However, the pullout force between the two simulated fluids varied significantly. The pullout force of the samples incubated in fasted state simulated gastric fluid was approximately twice that of the pullout force of the samples incubated in fasted state simulated intestinal fluid.

TABLE 1

| Arm tip formulation compositions. | | | | |
|---|---|---|---|---|
| | Formu-lation 1 | Formu-lation 6 | Formu-lation 14 | Formu-lation 15 |
| PCL (wt. %) | 30 | 30 | 30 | 30 |
| HPMC AS MG (wt. %) | 64.9 | 49.9 | 64.9 | 59.9 |
| Plasticizer (wt. %) | Propylene Glycol, 5 | P407, 10 | Propylene Glycol, 2.5 | Propylene Glycol, 5 |
| Stearic Acid (wt. %) | 0 | 0 | 2.5 | 5 |

Figure 14:
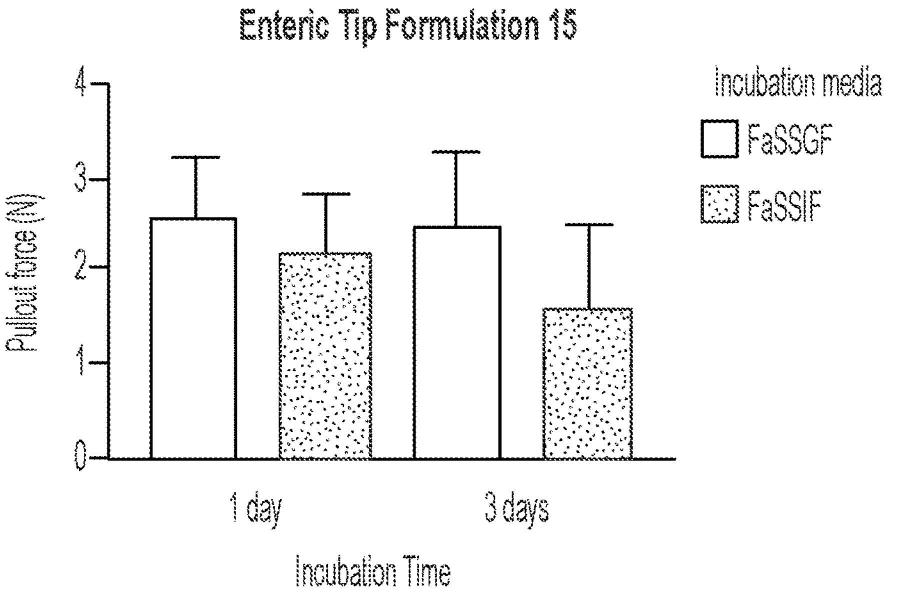
FIG. 14 shows pullout force data for gastric residence systems comprising filament and enteric tips (formulation 15), according to some embodiments.

Example 4: The pullout force required to separate a filament from an arm tip was tested at various incubation settings. As shown in FIG. 14, the pullout force was tested for filaments connected to arm tips having formulation 15 (shown in Table 1) using the pullout force testing procedure described in detail previously. Tips comprising this formulation are designed to remain connected to the filament in a highly acidic, or gastric environment, and separate or slip from the filament in an intestinal environment as the gastric residence system components pass through the intestine of a patient. Adhesion force was measured after samples were incubated in fasted state simulated gastric fluid (FaSSGF, pH 1.6) or fasted state simulated intestinal fluid (FaSSIF, pH 6.5) for both 1 and 3 days. As shown in the Figure, the length of incubation (i.e., 1 day or 3 days) only marginally affected the pullout force of samples incubated in the fasted state simulated gastric fluid. However, the pullout force of samples incubated for 3 days was approximately 75% that of the pullout force of samples incubated only 1 day in the fasted state simulated intestinal fluid. Additionally, the pullout force of the samples incubated in fasted state simulated gastric fluid was approximately at least 20% more than that of the pullout force of the samples incubated in fasted state simulated intestinal fluid.

Figure 15:
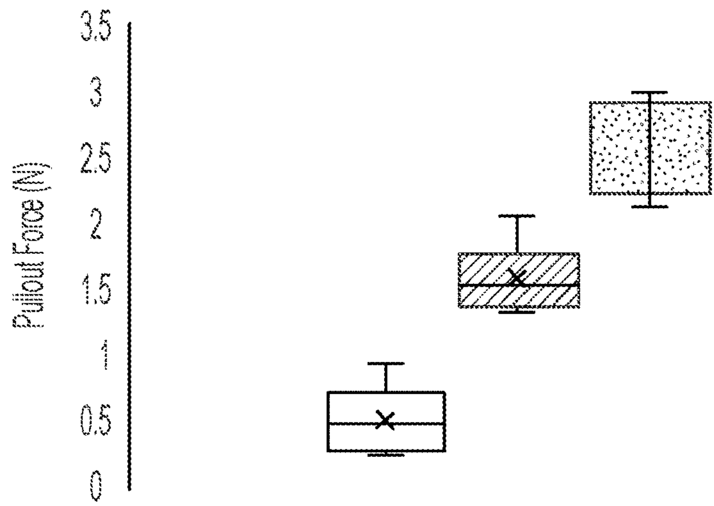
FIG. 15 shows pullout force data for filaments of gastric residence systems having filament of different securing methods, according to some embodiments.

Example 5: The pullout force required to separate a filament from an arm tip was tested for both knotted and heated filament ends. FIG. 15 shows the results of this test. The samples were incubated in fasted state simulated gastric fluid for three days. As shown in the Figure, the samples having knotted filament ends required the most force to separate the filament from the arm tip. The samples with heat-flared filament ends required less force to separate the filament from the arm tip than the knotted filament ends, but more force than the control samples (neither knotted nor heated). As shown in the Figure, the pullout force required to separate the knotted filament ends was approximately at least one and a half times that of the pullout force required to separate the heated filament ends from the arm tip, and approximately five times that of the pullout force required to separate the control (i.e., unknotted, unheated) filament ends from the arm tip.

Figure 16:
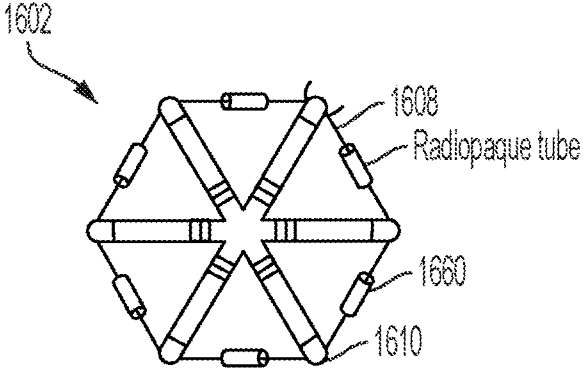
FIG. 16 shows a gastric residence system having filament that has been prepared for visualization when in a dog's stomach, according to some embodiments.

Example 6: Gastric residence of gastric residence systems comprising a filament were tested in dogs. FIG. 16 shows gastric residence system 1602 comprising filament 1608 having knotted ends. A radiopaque tube/marker 1660 was placed on filament 1608 between each arm tip 1610. Two or more radiopaque tube/marker 1660 can be used to identify the location and intactness of the gastric residence system in vivo via X-ray imaging. The radiopaque tube/marker 1660 comprised bismuth blended into a polymeric matrix. Specifically, bismuth-loaded polycaprolactone was formed into tubes, and the tubes were fed onto the filament between each arm during filament assembly. The radiopaque tubes could slide freely along the filament and could slide off the filament if filament ends slipped free from the stellate. During animal studies, filament intactness was tracked on X-rays by observing the number and orientation of radiopaque tubes visible.

Gastric residence systems were assembled with arm tips 1610 comprising enteric formulation 14 (see Table 1) via notching, wrapping, and rounding as shown in FIGS. 5A-5C. Arm tips 1610 were notched with a circular saw. Pellethane filaments were cut to length, radiopaque tubes were fed onto filaments, and filament ends were knotted. Filaments were added to gastric residence systems by feeding through the notches at the ends of the arms such that one radiopaque marker was located between each arm. The notches were then closed by applying pressure from a heated die (85° C., 25 psi, for 30 sec). Gastric residence systems were loaded into hydroxypropyl methylcellulose capsules and dosed orally in beagles. Gastric residence systems were visualized daily by X-ray for one week. The number of polycaprolactone tubes visible in X-rays is shown in Table 2. In two of the three dogs, webs remained intact for greater than one week. In the third gastric residence system, two radiopaque tubes separated from the stellate by day 7, and the stellate passed from the body by day 8. The data indicate that filaments comprising of these materials are sufficiently durable to support weeklong gastric residence.

TABLE 2

| Gastric residence in beagle dogs, tested using gastric residence systems having a filament. | | | | | | | | |
|---|---|---|---|---|---|---|---|---|
| Animal # | Day 1 | Day 2 | Day 3 | Day 4 | Day 5 | Day 6 | Day 7 | Day 8 |
| 1005 | 6/6 | 6/6 | 6/6 | 6/6 | 6/6 | 6/6 | 6/6 | 6/6 |
| 1006 | 6/6 | 6/6 | 6/6 | 6/6 | 6/6 | 6/6 | 6/6 | 6/6 |
| 1007 | 6/6 | 6/6 | 6/6 | 6/6 | 6/6 | 6/6 | 4/6 | 0/6 |

Example 7: The ability of a filament to prevent intact passage of a star shaped gastric residence system out of the stomach was evaluated in a dog model. Dosage forms were assembled with 40 A durometer silicone cores, enteric matrices, and PCL-based placebo arms to an outer diameter of 37 mm. The arms included radiopaque markers for X-ray tracking of gastric residence. The dosage forms were loaded into coated HPMC capsules and dosed in five beagle dogs. As a first study, the gastric residence systems were dosed without a filament. The gastric residence time ranged from 1-7 days, with an average of 3.2 days. X-ray imaging showed intact stellates in the intestine, suggesting that the dosage forms were able to pass out of the stomach intact. As addition of a filament to a dosage form is intended to help the dosage form resist intact passage through the pylorus, this stellate configuration was chosen to assess the ability of a filament to improve gastric retention time by resisting intact passage. Similar stellates were assembled (40 A core, 37 mm outer diameter, PCL-based arms) and a filament was attached to the end of each arm The filament was a flexible Pellethane tube, 80 A durometer, about 400 micron OD and about 250 micron ID. The dosage forms were folded into coated HPMC capsules and dosed in five beagles. X-ray imaging showed that gastric retention time ranged from 4-10 days with and average of 6.4 days. Addition of the filament was able to prolong gastric residence time for a dosage form that otherwise passed through the pylorus intact.

Example 8: The deployment time of gastric residence systems comprising a filament and sleeved on the arm-side of and the deployment time of gastric residence systems comprising a filament and sleeved on the core side was tested. Specifically, some gastric residence systems, such as stellate-shaped gastric residence systems, are configured to compact/fold at the core. Thus, when compacted/folded, the gastric residence system has an arm side (e.g., the side indicated by the arrow in FIG. 17A) and a core side (e.g., the side indicated by the arrow in FIG. 17C). The example described herein tests the deployment time for gastric residence systems that are compacted and sleeved on an arm side and gastric residence systems that are compacted and sleeved on a core side.

Figure 17A:
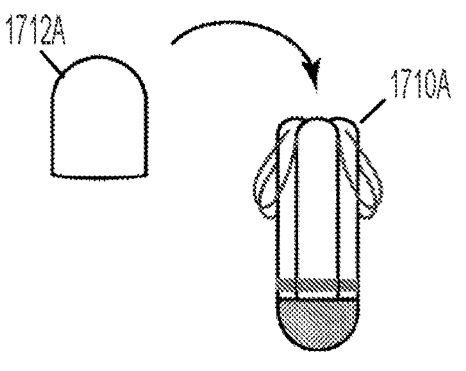
FIG. 17A shows a compacted/folded gastric residence system comprising a filament being sleeved on an arm side, according to some embodiments.
Figure 17B:
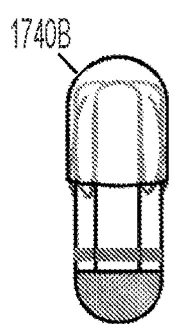
FIG. 17B shows a sleeved compacted/folded gastric residence system comprising a filament, according to some embodiments.
Figure 17C:
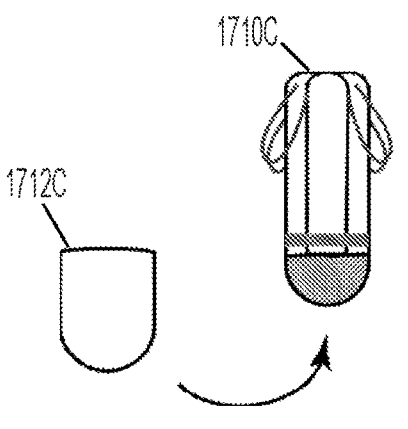
FIG. 17C shows a compacted/folded gastric residence system comprising a filament being sleeved on a core side, according to some embodiments.
Figure 17D:
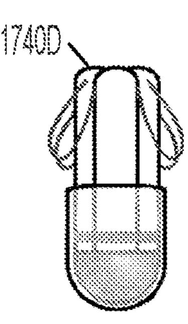
FIG. 17D shows a sleeved compacted/folded gastric residence system comprising a filament, according to some embodiments.

FIGS. 17A-17G shows different sleeving and encapsulation configurations for gastric residence systems comprising a filament. Specifically, FIG. 17A shows a compacted/folded gastric residence system 1710A that is being sleeved on an arm side with sleeve 1712A. Compacted/folded gastric residence system 1710A comprises a filament between each arm of the gastric residence system. Thus, the filament of the gastric residence system is covered by sleeve 1712A. FIG. 17B shows gastric residence system 1710A sleeved with sleeve 1712A on the arm side of the gastric residence system to form sleeved compacted/folded gastric residence system 1740B. FIG. 17C shows a compacted/folded gastric residence system 1710C. However, compacted/folded gastric residence system 1710C is shown being sleeved on the core side of the gastric residence system with sleeve 1712C. FIG. 17D shows compacted/folded gastric residence system 1710D sleeved with sleeve 1712C on the core side of the gastric residence system. Thus, unlike sleeved compacted/folded gastric residence system 1740B of FIG. 17B, the webbing of compacted/folded gastric residence system 1710C is not covered by sleeve 1712C in sleeved compacted/folded gastric residence system 1740D.

Figure 17E:
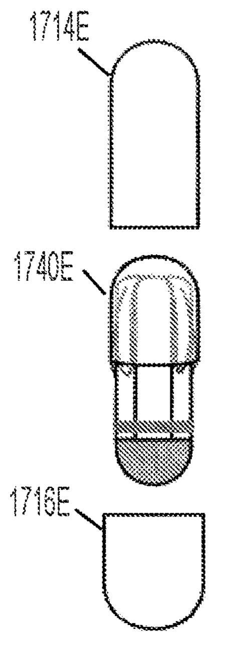
FIG. 17E shows a compacted/folded gastric residence system comprising a filament and sleeved on an arm side being encapsulated with a two-piece capsule, according to some embodiments.
Figure 17E:
Figure 17F:
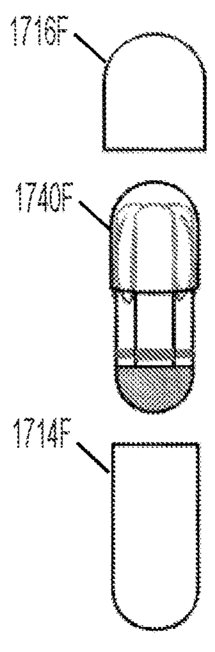
FIG. 17F shows a compacted/folded gastric residence system comprising a filament and sleeved on an arm side being encapsulated with a two-piece capsule, according to some embodiments.

FIGS. 17E and 17F show different encapsulation configurations for sleeved compacted/folded gastric residence systems. Both sleeved compacted/folded gastric residence system 1740E of FIG. 17E and sleeved compacted/folded gastric residence system 1740F of FIG. 17F are sleeved on an arm side of the gastric residence system. Further, FIG. 17E shows sleeved gastric residence system 1740E being encapsulated with a two-piece capsule. The cap of the two-piece capsule, cap 1716E, is shown encapsulating the sleeved gastric residence system on its core side, and the body of the two-piece capsule, body 1714E, is shown encapsulating the sleeved gastric residence system on its sleeved arm side. FIG. 17F shows sleeved gastric residence system 1740F being encapsulating with a two-piece capsule. However, unlike that of FIG. 17E, the sleeved compacted/folded gastric residence system 1740F of FIG. 17F is being encapsulated with the body of the two-piece capsule, body 1714F, encapsulating the core side, and the cap of the two-piece capsule, cap 1716F encapsulating the sleeved arm side of the gastric residence system.

Figure 17G:
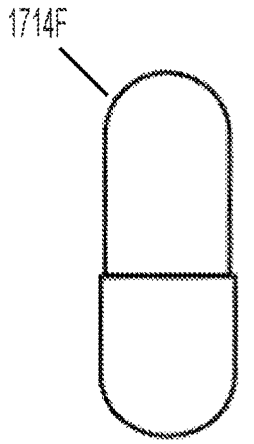
FIG. 17G shows an encapsulated compacted/folded gastric residence system, according to some embodiments.

FIG. 17G shows an encapsulated sleeved compacted/folded gastric residence system 1742G.

The sleeve used in these trials were VCaps Plus HPMC size 0. The sleeved gastric residence systems were then encapsulated in VCaps Plus HPMC capsules. Below, Table 3 shows deployment time data for arm-side sleeved gastric residence systems, and Table 4 shows deployment time data for core-side sleeved gastric residence systems. The data of both Tables 3 and 4 was obtained using the Deployment (Rocker) test at pH 7, described in further detail below.

TABLE 3

Arm-side sleeve deployment results.

| Capsule # | Deployment time (min) |
|---|---|
| 1 | 95.3 |
| 2 | 78.7 |
| 3 | 83.6 |
| 4 | 68.6 |
| 5 | 67.0 |
| Average | 78.6 |
| StDev | 11.6 |

TABLE 4

Core-side sleeve deployment results.

| Capsule # | Deployment time (min) |
|---|---|
| 1 | 87.8 |
| 2 | 130.2 |
| 3 | 107.7 |
| 4 | 81.9 |
| 5 | 55.6 |
| 6 | 71.0 |
| 7 | 101.0 |
| 8 | 84.8 |
| 9 | 85.7 |
| 10 | 59.0 |
| Average | 86.5 |
| StDev | 22.5 |

As shown in Tables 3 and 4, the deployment time of core-side sleeved gastric residence systems and arm-side sleeved gastric residence systems are similar. Although the average deployment time of core-side sleeved gastric residence systems is slightly greater than that of arm-side sleeved gastric residence systems, the difference is not enough to be statistically significant. Thus, the deployment time of arm-side gastric residence systems and the deployment time of core-side gastric residence systems, based on the data of Tables 3 and 4, are arguably the same.

Example 9: Degradable sutures can be used as filaments to enhance gastric residence properties of the gastric residence systems. The degradable sutures can be elastic or inelastic. Further, the degradable sutures can be bioresorbable. In some instances, the degradable sutures were attached to the enteric tips of the stellate arms.

To evaluate the effect of elasticity of the outer filament on the stellate resistance to compression to a size that can pass through the pylorus, stellate gastric residence systems were assembled using filaments of varying elasticity. Polyurethane elastomer (Pellethane tubing) was used as an elastic filament material, and poly(glyclolic acid) sutures were used as inelastic filaments. Filaments were attached to enteric tips of stellate arms via notching, spooling, and rounding. Radial force required to compress the stellates to a diameter of 20 mm was then measured using an iris tester.

Figure 18A:
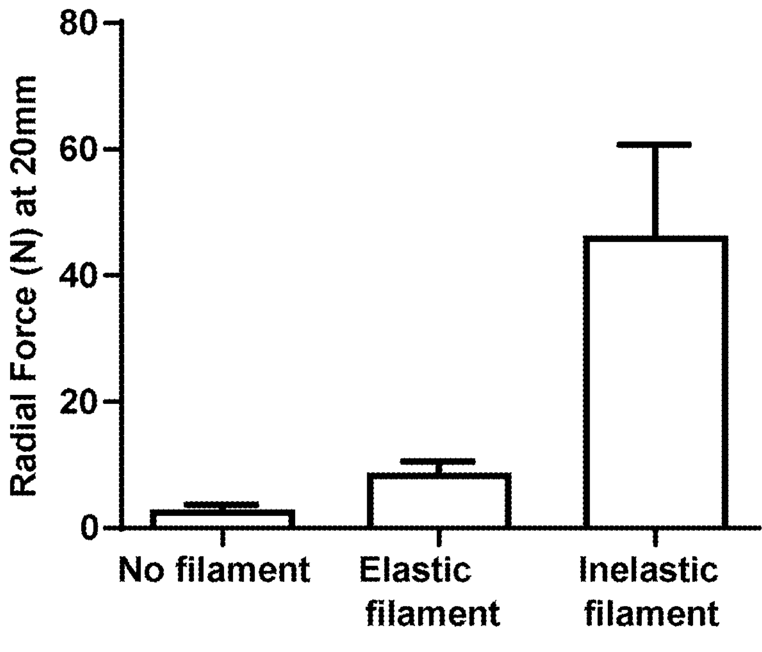
FIG. 18A shows the ability of elastic or inelastic filaments in increasing the resistance of a stellate gastric residence system to compression.

A shown in FIG. 18A, both filament materials increased the stellate's resistance to compression compared to stellates with no filament. In addition, stellates with inelastic webs had greater resistance to compression than stellates with elastic webs.

In addition, adhesion strength of PLGA sutures to stellate arms with enteric tips was evaluated by measuring pullout force after incubation. Stellate gastric residence systems were assembled with enteric tips and with filaments, made from either polyurethane elastomer (Pellethane) or PLGA sutures. The filaments were attached to enteric tips of stellate arms via notching, spooling, and rounding. Adhesion of the filament to stellate arms was measured before and after incubation in fasted state simulated gastric fluid for the indicated periods of time (0 day, 1 day, 4 days or 7 days).

Figure 18B:
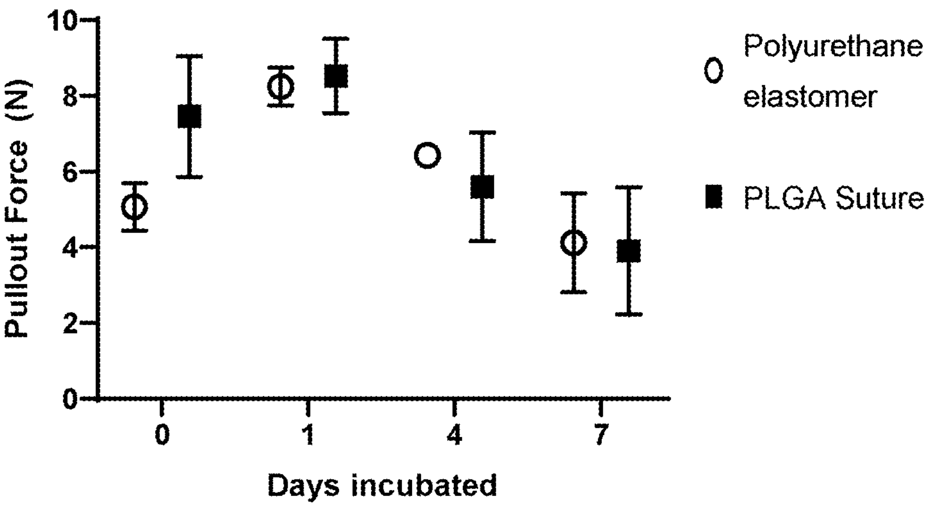
FIG. 18B shows the adhesion strength of degradable sutures to the enteric tips of gastric residence systems over time in a simulated gastric environment.

As shown in FIG. 18B, adhesion of both types of filaments was strongest at early timepoints and reduced at later timepoints, consistent with observed hydration and softening of the enteric tip material. More importantly, both the polyurethane elastomer and PLGA filament materials maintained an adhesion strength above the 1N target for at least 7 days.

EXEMPLARY EMBODIMENTS

Embodiment 1. A gastric residence system comprising:

a core;

a plurality of arms connected to the core at a proximal end through a plurality of linker components, one linker component of the plurality of linker components corresponding to each arm of the plurality of arms, and the plurality of arms extending radially from the proximal end; and a filament circumferentially connecting each arm of the plurality of arms.

Embodiment 2. The gastric residence system of embodiment 1, wherein the filament circumferentially connects a distal end of each arm of the plurality of arms.

Embodiment 3. The gastric residence system of embodiment 1 or 2, wherein the plurality of arms comprises at least three arms.

Embodiment 4. The gastric residence system of any of embodiments 1-3, wherein the plurality of arms is configured to be loaded with an active pharmaceutical ingredient.

Embodiment 5. The gastric residence system of any of embodiments 1-4, wherein the plurality of arms comprises 40-60% loading of an active pharmaceutical ingredient.

Embodiment 6. The gastric residence system of any of embodiments 1-5, wherein the linker component degrades, dissolves, disassociates, or mechanically weakens in a gastric environment.

Embodiment 7. The gastric residence system of any of embodiments 1-6, wherein the gastric residence system is configured to be folded during administration and is configured to assume an open configuration when in a patient's stomach.

Embodiment 8. The gastric residence system of embodiment 7, wherein the core undergoes elastic deformation when the gastric residence system is in the folded configuration and recoils when the gastric residence system assumes the open configuration.

Embodiment 9. The gastric residence system of any of embodiments 1-8, wherein the gastric residence system has a multi-armed star shape in the open configuration.

Embodiment 10. The gastric residence system of any of embodiments 1-9, wherein the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

Embodiment 11. The gastric residence system of any of embodiments 2-10, wherein the pullout force required to separate the filament from the distal end of a first arm of the plurality of arms is greater than 1N when measured after incubating the gastric residence system in an environment of pH 1.6 for 3 days.

Embodiment 12. The gastric residence system of any of embodiments 2-11, wherein the pullout force required to separate the filament from the distal end of the first arm of the plurality of arms is less than 2N when measured after incubating the gastric residence system in an environment of pH 6.5 for 3 days.

Embodiment 13. The gastric residence system of any of embodiments 1-12, wherein the distal end of each arm of the plurality of arms comprises an enteric material.

Embodiment 14. The gastric residence system of any of embodiments 1-13, wherein the filament comprises one or more of an elastic polymer, a biosorbable polymer, and a plasticizer.

Embodiment 15. The gastric residence system of embodiment 13 or 14, wherein the enteric material of the distal end of each arm comprises a polymer, an enteric polymer, a plasticizer, and an acid.

Embodiment 16. The gastric residence system of embodiment 15, wherein the polymer comprises polycaprolactone or TPU.

Embodiment 17. The gastric residence system of embodiment 15 or 16, wherein the enteric polymer comprises hydroxypropylmethylcellulose acetate succinate.

Embodiment 18. The gastric residence system of any of embodiments 15-17, wherein the plasticizer comprises propylene glycol.

Embodiment 19. The gastric residence system of any of embodiments 15-18, wherein the acid comprises stearic acid.

Embodiment 20. The gastric residence system of any of embodiments 1-19, wherein the distal end of each arm comprises a notch and the filament is positioned within the notch of each distal end.

Embodiment 21. The gastric residence system of embodiment 20, wherein the filament is secured by overlapping a first end of the filament and a second end of the filament within a first notch, and the first end and the second end are secured by enlarging the first end and the second end of the filament.

Embodiment 22. The gastric residence system of any of embodiments 1-21, wherein each arm of the plurality of arms comprises a first segment comprising a first polymer composition and a second segment comprising a second polymer composition, wherein the first segment has a stiffness greater than a stiffness of the second segment, as measured using a 3-point bending test per ASTM D790.

Embodiment 23. The gastric residence system of embodiment 22, wherein the force required to compress the gastric residence system into a configuration small enough to pass through an opening having a diameter of 20 mm is at least 1.2 times greater than the force required to compress a gastric residence system having arms comprising only a first polymer composition into a configuration small enough to pass through the opening, as measured using an iris testing mechanism.

Embodiment 24. The gastric residence system of embodiment 22 or 23, wherein the first polymer composition comprises one or more of PCL, PLA, PLGA, HPMCAS, and TPU.

Embodiment 25. The gastric residence system of any of embodiments 22-24, wherein the second polymer composition comprises one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, and a silicone.

Embodiment 26. The gastric residence system of any of embodiments 22-25, wherein the second polymer composition comprises at least a polycaprolactone and a soluble material to form a material that softens upon exposure to an aqueous environment.

Embodiment 27. The gastric residence system of any of embodiments 22-26, wherein the first segment is directly connected to the second segment of each arm of the plurality of arms.

Embodiment 28. The gastric residence system of any of embodiments 22-27, wherein the first segment is connected to the second segment via a linker.

Embodiment 29. The gastric residence system of any of embodiments 22-28, wherein the first segment comprises 20-50% of a length of at least the first arm of the plurality of arms, the length being measured from a proximal end of the first arm, the proximal end being proximate to the core, to a distal end of the first arm.

Embodiment 30. The gastric residence system of any embodiments 22-29, wherein the second segment comprises 50-80% of a length of at least the first arm of the plurality of arms, the length being measured from a proximal end of the first arm, the proximal end being proximate to the core, to a distal end of the first arm.

Embodiment 31. The gastric residence system of any of embodiments 22-30, wherein a number of fatigue cycles required to break the gastric residence system is at least 25% greater than a number of fatigue cycles required to break a gastric residence system with arms comprising only a first polymer composition, as measured using a double funnel test.

Embodiment 32. The gastric residence system of any of embodiments 1-31, wherein the gastric residence system is configured to be encapsulated with a capsule when the gastric residence system is in a folded configuration to form a gastric residence dosage form suitable for administering to a patient, and the gastric residence dosage form is configured to release the gastric residence system in a stomach of the patient, allowing the gastric residence to assume an open configuration.

Embodiment 33. The gastric residence system of any of embodiments 1-32, wherein the gastric residence system is used to treat a patient.

Embodiment 34. The gastric residence system of embodiment 33, wherein the patient is a human or a dog.

Embodiment 35. A gastric residence system comprising:

a plurality of arms connected at a proximal end, the plurality of arms extending radially from the proximal end; and a filament circumferentially connecting a distal end of each arm of the plurality of arms.

Embodiment 36. The gastric residence system of embodiment 35, comprising a core, wherein each arm of the plurality of arms is connected to the core at the proximal end of each arm.

Embodiment 37. The gastric residence system of embodiment 35 or 36, wherein the plurality of arms comprises at least three arms.

Embodiment 38. The gastric residence system of embodiment 35 or 36, wherein the plurality of arms is configured to be loaded with an active pharmaceutical ingredient.

Embodiment 39. The gastric residence system of any of embodiments 35-38, wherein the plurality of arms comprises 40-60% loading of an active pharmaceutical ingredient.

Embodiment 40. The gastric residence system of any of embodiments 36-39, comprising a plurality of linker components, wherein one linker component of the plurality of linker components connects one arm of the plurality of arms to the core.

Embodiment 41. The gastric residence system of embodiment 40, wherein each linker component of the plurality of linker component degrades, dissolves, disassociates, or mechanically weakens in a gastric environment.

Embodiment 42. The gastric residence system of any of embodiments 35-41, wherein the gastric residence system is configured to be folded during administration and is configured to assume an open configuration when in a patient's stomach.

Embodiment 43. The gastric residence system of embodiment 42, wherein the core undergoes elastic deformation when the gastric residence system is in the folded configuration and recoils when the gastric residence system assumes the open configuration.

Embodiment 44. The gastric residence system of any of embodiments 35-43, wherein the gastric residence system has a multi-armed star shape in the open configuration.

Embodiment 45. The gastric residence system of embodiment 35-44, wherein the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

Embodiment 46. The gastric residence system of any of embodiments 35-45, wherein the pullout force required to separate the filament from the distal end of a first arm of the plurality of arms is greater than 1N when measured after incubating the gastric residence system in an environment of pH 1.6 for 3 days.

Embodiment 47. The gastric residence system of any of embodiments 35-46, wherein the pullout force required to separate the filament from the distal end of the first arm of the plurality of arms is less than 2N when measured after incubating the gastric residence system in an environment of pH 6.5 for 3 days.

Embodiment 48. The gastric residence system of any of embodiments 35-47, wherein the distal end of each arm of the plurality of arms comprises an enteric material.

Embodiment 49. The gastric residence system of any of embodiments 35-48, wherein the filament comprises one or more of an elastic polymer, a biosorbable polymer, and a plasticizer.

Embodiment 50. The gastric residence system of embodiment 48 or 49, wherein the enteric material of the distal end of each arm comprises a polymer, an enteric polymer, a plasticizer, and an acid.

Embodiment 51. The gastric residence system of embodiment 50, wherein the polymer comprises polycaprolactone or TPU.

Embodiment 52. The gastric residence system of embodiment 50 or 51, wherein the enteric polymer comprises hydroxypropylmethylcellulose acetate succinate.

Embodiment 53. The gastric residence system of any of embodiments 50-52, wherein the plasticizer comprises propylene glycol.

Embodiment 54. The gastric residence system of any of embodiments 50-53, wherein the acid comprises stearic acid.

Embodiment 55. The gastric residence system of any of embodiments 35-54, wherein the distal end of each arm comprises a notch and the filament is positioned within the notch of each distal end.

Embodiment 56. The gastric residence system of embodiment 55, wherein the filament is secured by overlapping a first end of the filament and a second end of the filament within a first notch, and the first end and the second end are secured by one of knotting or heat flaring.

Embodiment 57. The gastric residence system of any of embodiments 35-56, wherein each arm of the plurality of arms comprises a first segment comprising a first polymer composition and a second segment comprising a second polymer composition, wherein the first segment has a stiffness greater than a stiffness of the second segment, as measured using a 3-point bending test per ASTM D790.

Embodiment 58. The gastric residence system of embodiment 57, wherein the force required to compress the gastric residence system into a configuration small enough to pass through an opening having a diameter of 20 mm is at least 1.2 times greater than the force required to compress a gastric residence system having arms comprising only a first polymer composition into a configuration small enough to pass through the opening, as measured using an iris testing mechanism.

Embodiment 59. The gastric residence system of embodiment 57 or 58, wherein the first polymer composition comprises one or more of PCL, PLA, PLGA, HPMCAS, and TPU.

Embodiment 60. The gastric residence system of any of embodiments 57-59, wherein the second polymer composition comprises one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, and a silicone.

Embodiment 61. The gastric residence system of any of embodiments 57-60, wherein the second polymer composition comprises at least a polycaprolactone and a soluble material to form a material that softens upon exposure to an aqueous environment.

Embodiment 62. The gastric residence system of any of embodiments 57-61, wherein the first segment is directly connected to the second segment of at least the first arm of the plurality of arms.

Embodiment 63. The gastric residence system of any of embodiments 57-62, wherein the first segment is connected to the second segment through a linker component.

Embodiment 64. The gastric residence system of any of embodiments 57-63, wherein the first segment comprises 20-50% of a length of at least the first arm, the length being measured from a proximal end of the first arm, the proximal end being proximate to the core, to a distal end of the first arm.

Embodiment 65. The gastric residence system of any embodiments 57-64, wherein the second segment comprises 50-80% of a length of the at least one arm, the length being measured from a proximal end of the at least one arm, the proximal end being proximate to the core, to a distal end of the at least one arm.

Embodiment 66. The gastric residence system of any of embodiments 57-65, wherein a number of fatigue cycles required to break the gastric residence system is at least 25% greater than a number of fatigue cycles required to break a gastric residence system with arms comprising only a first polymer composition, as measured using a double funnel test.

Embodiment 67. The gastric residence system of any of embodiments 35-66, wherein the gastric residence system is configured to be encapsulated with a capsule when the gastric residence system is in a folded configuration to form a gastric residence dosage form suitable for administering to a patient, and the gastric residence dosage form is configured to release the gastric residence system in a stomach of the patient, allowing the gastric residence to assume an open configuration.

Embodiment 68. The gastric residence system of any of embodiments 35-67, wherein the gastric residence system is used to treat a patient.

Embodiment 69. The gastric residence system of embodiment 68, wherein the patient is a human or a dog.

Embodiment 70. A method of manufacturing a gastric residence system comprising:

preparing gastric residence system comprising a plurality of arms connected to a core at a proximal end through a plurality of linker components, one linker component of the plurality of linker components corresponding to each arm of the plurality of arms, and the plurality of arms extending radially;

notching each arm of the plurality of arms to form a notch in each arm;

wrapping a filament circumferentially around the gastric residence system such that the filament is positioned within each notch of each arm; and closing each notch to secure the filament within each notch.

Embodiment 71. The method of embodiment 70, wherein the filament circumferentially connects a distal end of each arm of the plurality of arms.

Embodiment 72. The method of embodiment 70 or 71, wherein the plurality of arms comprises at least three arms.

Embodiment 73. The method of any of embodiments 70-72, wherein the plurality of arms is configured to be loaded with an active pharmaceutical ingredient.

Embodiment 74. The method of any of embodiments 70-73, wherein the plurality of arms comprises 40-60% loading of an active pharmaceutical ingredient.

Embodiment 75. The method of any of embodiments 70-74, wherein the linker component degrades, dissolves, disassociates, or mechanically weakens in a gastric environment.

Embodiment 76. The method of any of embodiments 70-75, wherein the gastric residence system is configured to be folded during administration and is configured to assume an open configuration when in a patient's stomach.

Embodiment 77. The method of embodiment 76, wherein the core undergoes elastic deformation when the gastric residence system is in the folded configuration and recoils when the gastric residence system assumes the open configuration.

Embodiment 78. The method of any of embodiments 70-77, wherein the gastric residence system has a multi-armed star shape in the open configuration.

Embodiment 79. The method of any embodiment 70-78, wherein closing each notch comprises at least one of knotting or heating.

Embodiment 80. The method of any of embodiments 70-79, wherein the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

Embodiment 81. The method of any of embodiments 70-80, wherein the pullout force required to separate the filament from the distal end of a first arm of the plurality of arms is greater than 1N when measured after incubating the gastric residence system in an environment of pH 1.6 for 3 days.

Embodiment 82. The method of any of embodiments 70-81, wherein the pullout force required to separate the filament from the distal end of the first arm of the plurality of arms is less than 2N when measured after incubating the gastric residence system in an environment of pH 6.5 for 3 days.

Embodiment 83. The method of any of embodiments 70-82, wherein the distal end of each arm of the plurality of arms comprises an enteric material.

Embodiment 84. The method of any of embodiments 70-83, wherein the filament comprises one or more of an elastic polymer, a biosorbable polymer, and a plasticizer.

Embodiment 85. The method of any of embodiments 70-84, wherein the enteric material of the distal end of each arm comprises a polymer, an enteric polymer, a plasticizer, and an acid.

Embodiment 86. The method of embodiment 85, wherein the polymer comprises polycaprolactone.

Embodiment 87. The method of embodiment 85 or 86, wherein the enteric polymer comprises hydroxypropylmethylcellulose acetate succinate.

Embodiment 88. The method of any of embodiments 85-87, wherein the plasticizer comprises propylene glycol.

Embodiment 89. The method of any of embodiments 85-88, wherein the acid comprises stearic acid.

Embodiment 90. The method of any of embodiments 70-89, wherein each arm of the plurality of arms comprises a first segment comprising a first polymer composition and a second segment comprising a second polymer composition, wherein the first segment has a stiffness greater than a stiffness of the second segment, as measured using a 3-point bending test per ASTM D790.

Embodiment 91. The method of embodiment 90, wherein the force required to compress the gastric residence system into a configuration small enough to pass through an opening having a diameter of 20 mm is at least 1.2 times greater than the force required to compress a gastric residence system having arms comprising only a first polymer composition into a configuration small enough to pass through the opening, as measured using an iris testing mechanism.

Embodiment 92. The method of embodiment 90 or 91, wherein the first polymer composition comprises one or more of PCL, PLA, PLGA, HPMCAS, and TPU.

Embodiment 93. The method of any of embodiments 90-92, wherein the second polymer composition comprises one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, and a silicone.

Embodiment 94. The method of any of embodiments 90-93, wherein the second polymer composition comprises at least a polycaprolactone and a soluble material to form a material that softens upon exposure to an aqueous environment.

Embodiment 95. The method of any of embodiments 90-94, wherein the first segment is directly connected to the second segment of the at least one arm.

Embodiment 96. The method of any of embodiments 90-95, wherein the first segment is connected to the second segment through a linker component.

Embodiment 97. The method of any of embodiments 90-96, wherein the first segment comprises 20-50% of a length of the at least one arm, the length being measured from a proximal end of the at least one arm, the proximal end being proximate to the core, to a distal end of the at least one arm.

Embodiment 98. The method of any embodiments 90-97, wherein the second segment comprises 50-80% of a length of the at least one arm, the length being measured from a proximal end of the at least one arm, the proximal end being proximate to the core, to a distal end of the at least one arm.

Embodiment 99. The method of any of embodiments 90-98, wherein a number of fatigue cycles required to break the gastric residence system is at least 25% greater than a number of fatigue cycles required to break a gastric residence system with arms comprising only a first polymer composition, as measured using a double funnel test.

Embodiment 100. The method of any of embodiments 90-99, wherein the gastric residence system is configured to be encapsulated with a capsule when the gastric residence system is in a folded configuration to form a gastric residence dosage form suitable for administering to a patient, and the gastric residence dosage form is configured to release the gastric residence system in a stomach of the patient, allowing the gastric residence to assume an open configuration.

Embodiment 101. A gastric residence system made using the method of any of embodiments 70-100, wherein the gastric residence system is used to treat a patient.

Embodiment 102. The gastric residence system of embodiment 101, wherein the patient is a human or a dog.

Embodiment 103. A method of manufacturing a gastric residence system comprising:

- preparing a gastric residence system comprising a plurality of arms connected to a core at a proximal end through a plurality of linker components, one linker component of the plurality of the plurality of linker components corresponding to each arm of the plurality of arms, and the plurality of arms extending radially;
- preparing a plurality of tips and a filament, one tip for each arm of the plurality of arms, wherein the filament is attached to each tip of the plurality of tips;
- connecting each tip of the plurality of tips to an arm of the plurality of arms to form a gastric residence system comprising a filament.

Embodiment 104. The method of embodiment 103, wherein preparing a plurality of tips and a filament comprises injection molding.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X".

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A gastric residence system comprising:

a core;

a plurality of arms connected to the core at a proximal end through a plurality of linker components, one linker component of the plurality of linker components corresponding to each arm of the plurality of arms, and the plurality of arms extending radially from the proximal end; and a filament circumferentially connecting each arm of the plurality of arms.

2. The gastric residence system of claim 1, wherein the filament circumferentially connects a distal end of each arm of the plurality of arms.

3. The gastric residence system of claim 1, wherein at least one arm of the plurality of arms comprises a segment comprising 40-60% loading of an active pharmaceutical ingredient.

4. The gastric residence system of claim 1, wherein the gastric residence system is configured to be folded during administration and is configured to assume an open configuration when in a patient's stomach and the linker component degrades, dissolves, disassociates, or mechanically weakens in a gastric environment.

5. The gastric residence system of claim 4, wherein the core undergoes elastic deformation when the gastric residence system is in the folded configuration and recoils when the gastric residence system assumes the open configuration.

6. The gastric residence system of claim 1, wherein the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

7. The gastric residence system of claim 2, wherein the pullout force required to separate the filament from the distal end of a first arm of the plurality of arms is greater than 1N when measured after incubating the gastric residence system in an environment of pH 1.6 for 3 days and less than 2N when measured after incubating the gastric residence system in an environment of pH 6.5 for 3 days.

8. The gastric residence system of claim 1, wherein the distal end of each arm of the plurality of arms comprises an enteric material comprising a polymer, an enteric polymer, a plasticizer, and an acid.

9. The gastric residence system of claim 1, wherein the filament comprises one or more of an elastic polymer, a biosorbable polymer, and a plasticizer.

10. The gastric residence system of claim 8, wherein the polymer comprises polycaprolactone or TPU, the enteric polymer comprises hydroxypropylmethylcellulose acetate succinate, the plasticizer comprises propylene glycol, the acid comprises stearic acid.

11. The gastric residence system of claim 1, wherein the distal end of each arm comprises a notch and the filament is positioned within the notch of each distal end.

12. The gastric residence system of claim 1, wherein each arm of the plurality of arms comprises a first segment comprising a first polymer composition and a second segment comprising a second polymer composition, wherein the first segment has a stiffness greater than a stiffness of the second segment, as measured using a 3-point bending test per ASTM D790.

13. The gastric residence system of claim 12, wherein the force required to compress the gastric residence system into a configuration small enough to pass through an opening having a diameter of 20 mm is at least 1.2 times greater than the force required to compress a gastric residence system having arms comprising only a first polymer composition into a configuration small enough to pass through the opening, as measured using an iris testing mechanism.

14. The gastric residence system of claim 12, wherein the first polymer composition comprises one or more of PCL, PLA, PLGA, HPMCAS, and TPU and the second polymer composition comprises one or more of a polyurethane, a polyether-polyamide copolymer, a thermoplastic elastomer, a thermoplastic polyurethane, polycaprolactone polylactic acid copolymer, a poly (trimethylene carbonate), a polyglycerol sebacate, and a silicone.

15. The gastric residence system of claim 12, wherein the first segment comprises 20-50% of a length of at least the first arm of the plurality of arms, the length being measured from a proximal end of the first arm, the proximal end being proximate to the core, to a distal end of the first arm and the second segment comprises 50-80% of a length of at least the first arm of the plurality of arms, the length being measured from a proximal end of the first arm, the proximal end being proximate to the core, to a distal end of the first arm.

16. The gastric residence system of claim 12, wherein a number of fatigue cycles required to break the gastric residence system is at least 25% greater than a number of fatigue cycles required to break a gastric residence system with arms comprising only a first polymer composition, as measured using a double funnel test.

17. The gastric residence system of claim 1, wherein the gastric residence system is configured to be encapsulated with a capsule when the gastric residence system is in a folded configuration to form a gastric residence dosage form suitable for administering to a patient, and the gastric residence dosage form is configured to release the gastric residence system in a stomach of the patient, allowing the gastric residence to assume an open configuration.

18. The gastric residence system of claim 1, wherein the gastric residence system is used to treat a human.

19. A gastric residence system comprising:

a plurality of arms connected at a proximal end, the plurality of arms extending radially from the proximal end; and a filament circumferentially connecting a distal end of each arm of the plurality of arms.

20. A method of manufacturing a gastric residence system comprising:

preparing gastric residence system comprising a plurality of arms connected to a core at a proximal end through a plurality of linker components, one linker component of the plurality of linker components corresponding to each arm of the plurality of arms, and the plurality of arms extending radially;

notching each arm of the plurality of arms to form a notch in each arm;

wrapping a filament circumferentially around the gastric residence system such that the filament is positioned within each notch of each arm; and closing each notch to secure the filament within each notch.

* * * * *